US012665081B2

(12) United States Patent
Greene et al.

(10) Patent No.: US 12,665,081 B2
(45) Date of Patent: Jun. 23, 2026

(54) DYNAMIC REPORT BUILDING

(71) Applicant: Dexcom, Inc., San Diego, CA (US)

(72) Inventors: Adam R. Greene, Portland, OR (US); Justin E. Schumacher, Portland, OR (US); Daniel N. Root, Portland, OR (US)

(73) Assignee: Dexcom, Inc., San Diego, CA (US)

( * ) Notice: Subject to any disclaimer, the term of this patent is extended or adjusted under 35 U.S.C. 154(b) by 0 days.

(21) Appl. No.: 18/674,553

(22) Filed: May 24, 2024

(65) Prior Publication Data

US 2024/0312620 A1     Sep. 19, 2024

Related U.S. Application Data

(63) Continuation of application No. 17/470,364, filed on Sep. 9, 2021, now Pat. No. 12,080,414, which is a
(Continued)

(51) Int. Cl.
G16H 40/63          (2018.01)
G01N 33/48          (2006.01)
(Continued)

(52) U.S. Cl.
CPC ............. G16H 40/63 (2018.01); G01N 33/48 (2013.01); G06T 11/206 (2013.01); G16H 15/00 (2018.01); G06T 2210/41 (2013.01)

(58) Field of Classification Search
CPC ........ G16H 40/63; G16H 15/00; G01N 33/48; G06T 11/206; G06T 2210/41
(Continued)

(56) References Cited

U.S. PATENT DOCUMENTS

| 802,708 | A | 10/1905 | Powers et al. |
| 4,757,022 | A | 7/1988 | Shults et al. |

(Continued)

FOREIGN PATENT DOCUMENTS

| CN | 1747683 | A | 3/2006 |
| CN | 101278847 | A | 10/2008 |

(Continued)

OTHER PUBLICATIONS

International Preliminary Report on Patentability for Application No. PCT/US2013/043869 mailed Dec. 18, 2014, 6 pages.
(Continued)

*Primary Examiner* — Michael Tomaszewski
(74) *Attorney, Agent, or Firm* — PATTERSON + SHERIDAN, LLP

(57)          ABSTRACT

Methods and apparatus, including computer program products, are provided for processing analyte data. In some exemplary embodiments, there is provided a method. The method may include selecting at least one module from among a plurality of modules, the selection performed based on metadata including one or more of the following rules: whether the at least one module can be used with a type of device, whether the at least one module can be used with a glycemic state of a host, and whether the at least one module can be used with an expected volume of data generated by the type of device; and generating a report including the selected at least one module configured to present information representative of the glucose concentration level measured in the host. Related systems, methods, and articles of manufacture are also disclosed.

20 Claims, 41 Drawing Sheets

Related U.S. Application Data continuation of application No. 16/565,286, filed on Sep. 9, 2019, now Pat. No. 11,145,410, which is a continuation of application No. 13/789,339, filed on Mar. 7, 2013, now Pat. No. 10,453,573, which is a continuation of application No. 13/788,375, filed on Mar. 7, 2013, now abandoned.

(60) Provisional application No. 61/655,991, filed on Jun. 5, 2012.

(51) Int. Cl.
*G06T 11/20* (2006.01)
*G16H 15/00* (2018.01)

(58) Field of Classification Search
USPC ........................................................ 705/2–3
See application file for complete search history.

(56) References Cited

U.S. PATENT DOCUMENTS

| | | | |
|---|---|---|---|
| 4,994,167 A | 2/1991 | Shults et al. |
| 6,001,067 A | 12/1999 | Shults et al. |
| 6,477,424 B1 | 11/2002 | Thompson et al. |
| 6,558,321 B1 | 5/2003 | Burd et al. |
| 6,702,857 B2 | 3/2004 | Brauker et al. |
| 6,741,877 B1 | 5/2004 | Shults et al. |
| 6,862,465 B2 | 3/2005 | Shults et al. |
| 6,931,327 B2 | 8/2005 | Goode, Jr. et al. |
| 7,074,307 B2 | 7/2006 | Simpson et al. |
| 7,081,195 B2 | 7/2006 | Simpson et al. |
| 7,103,578 B2 | 9/2006 | Beck et al. |
| 7,108,778 B2 | 9/2006 | Simpson et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,192,450 B2 | 3/2007 | Brauker et al. |
| 7,226,978 B2 | 6/2007 | Tapsak et al. |
| 7,276,029 B2 | 10/2007 | Goode, Jr. et al. |
| 7,310,544 B2 | 12/2007 | Brister et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,368 B2 | 11/2009 | Brown |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,647,237 B2 | 1/2010 | Malave et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,685,005 B2 | 3/2010 | Riff et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,761,130 B2 | 7/2010 | Simpson et al. |
| 7,771,352 B2 | 8/2010 | Shults et al. |
| 7,774,145 B2 | 8/2010 | Brauker et al. |
| 7,775,975 B2 | 8/2010 | Brister et al. |
| 7,778,680 B2 | 8/2010 | Goode, Jr. et al. |
| 7,783,333 B2 | 8/2010 | Brister et al. |
| 7,792,562 B2 | 9/2010 | Shults et al. |
| 7,797,028 B2 | 9/2010 | Goode, Jr. et al. |
| 7,814,143 B2 | 10/2010 | Brown et al. |
| 7,826,981 B2 | 11/2010 | Goode, Jr. et al. |
| 7,828,728 B2 | 11/2010 | Boock et al. |
| 7,831,287 B2 | 11/2010 | Brister et al. |
| 7,835,777 B2 | 11/2010 | Shults et al. |
| 7,853,455 B2 | 12/2010 | Brown |
| 7,857,760 B2 | 12/2010 | Brister et al. |
| 7,860,545 B2 | 12/2010 | Shults et al. |
| 7,875,293 B2 | 1/2011 | Shults et al. |
| 7,881,763 B2 | 2/2011 | Brauker et al. |
| 7,885,697 B2 | 2/2011 | Brister et al. |
| 7,896,809 B2 | 3/2011 | Simpson et al. |
| 7,899,511 B2 | 3/2011 | Shults et al. |
| 7,901,354 B2 | 3/2011 | Shults et al. |
| 7,905,833 B2 | 3/2011 | Brister et al. |
| 7,914,450 B2 | 3/2011 | Goode, Jr. et al. |
| 7,917,186 B2 | 3/2011 | Kamath et al. |
| 7,920,906 B2 | 4/2011 | Goode, Jr. et al. |
| 7,925,321 B2 | 4/2011 | Goode et al. |
| 7,927,274 B2 | 4/2011 | Rasdal et al. |
| 7,933,639 B2 | 4/2011 | Goode et al. |
| 7,935,057 B2 | 5/2011 | Goode, Jr. et al. |
| 7,946,984 B2 | 5/2011 | Brister et al. |
| 7,949,381 B2 | 5/2011 | Brister et al. |
| 7,955,261 B2 | 6/2011 | Goode et al. |
| 7,959,569 B2 | 6/2011 | Goode et al. |
| 7,970,448 B2 | 6/2011 | Shults et al. |
| 7,974,672 B2 | 7/2011 | Shults et al. |
| 7,976,492 B2 | 7/2011 | Brauker et al. |
| 7,979,104 B2 | 7/2011 | Kamath et al. |
| 7,986,986 B2 | 7/2011 | Goode et al. |
| 7,998,071 B2 | 8/2011 | Goode, Jr. et al. |
| 8,000,901 B2 | 8/2011 | Brauker et al. |
| 8,005,524 B2 | 8/2011 | Brauker et al. |
| 8,005,525 B2 | 8/2011 | Goode, Jr. et al. |
| 8,010,174 B2 | 8/2011 | Goode, Jr. et al. |
| 8,050,731 B2 | 11/2011 | Tapsak et al. |
| 8,052,601 B2 | 11/2011 | Goode, Jr. et al. |
| 8,053,018 B2 | 11/2011 | Tapsak et al. |
| 8,060,173 B2 | 11/2011 | Goode, Jr. et al. |
| 8,060,174 B2 | 11/2011 | Simpson et al. |
| 8,064,977 B2 | 11/2011 | Boock et al. |
| 8,073,519 B2 | 12/2011 | Goode, Jr. et al. |
| 8,073,520 B2 | 12/2011 | Kamath et al. |
| 8,118,877 B2 | 2/2012 | Brauker et al. |
| 8,128,562 B2 | 3/2012 | Goode, Jr. et al. |
| 8,133,178 B2 | 3/2012 | Brauker et al. |
| 8,150,488 B2 | 4/2012 | Goode, Jr. et al. |
| 8,155,723 B2 | 4/2012 | Shults et al. |
| 8,160,669 B2 | 4/2012 | Brauker et al. |
| 8,160,671 B2 | 4/2012 | Kamath et al. |
| 8,167,801 B2 | 5/2012 | Goode, Jr. et al. |
| 8,170,803 B2 | 5/2012 | Kamath et al. |
| 8,195,265 B2 | 6/2012 | Goode, Jr. et al. |
| 8,206,297 B2 | 6/2012 | Kamath et al. |
| 8,216,139 B2 | 7/2012 | Brauker et al. |
| 8,229,534 B2 | 7/2012 | Brister et al. |
| 8,229,535 B2 | 7/2012 | Mensinger et al. |
| 8,229,536 B2 | 7/2012 | Goode, Jr. et al. |
| 8,231,531 B2 | 7/2012 | Brister et al. |
| 8,233,958 B2 | 7/2012 | Brauker et al. |
| 8,233,959 B2 | 7/2012 | Kamath et al. |
| 8,249,684 B2 | 8/2012 | Kamath et al. |
| 8,251,906 B2 | 8/2012 | Brauker et al. |
| 8,255,030 B2 | 8/2012 | Petisce et al. |
| 8,255,032 B2 | 8/2012 | Petisce et al. |
| 8,255,033 B2 | 8/2012 | Petisce et al. |
| 8,257,259 B2 | 9/2012 | Brauker et al. |
| 8,260,393 B2 | 9/2012 | Kamath et al. |
| 8,265,725 B2 | 9/2012 | Brauker et al. |
| 8,275,437 B2 | 9/2012 | Brauker et al. |
| 8,275,438 B2 | 9/2012 | Simpson et al. |
| 8,277,713 B2 | 10/2012 | Petisce et al. |
| 8,280,475 B2 | 10/2012 | Brister et al. |
| 8,282,549 B2 | 10/2012 | Brauker et al. |
| 8,282,550 B2 | 10/2012 | Rasdal et al. |
| 8,285,354 B2 | 10/2012 | Goode et al. |
| 8,287,453 B2 | 10/2012 | Li et al. |

(56) References Cited

U.S. PATENT DOCUMENTS

| | | | |
|---|---|---|---|
| 8,290,559 | B2 | 10/2012 | Shariati et al. |
| 8,290,560 | B2 | 10/2012 | Kamath et al. |
| 8,290,561 | B2 | 10/2012 | Brauker et al. |
| 8,290,562 | B2 | 10/2012 | Goode, Jr. et al. |
| 8,292,810 | B2 | 10/2012 | Goode, Jr. et al. |
| 8,298,142 | B2 | 10/2012 | Simpson et al. |
| 8,311,749 | B2 | 11/2012 | Brauker et al. |
| 8,313,433 | B2 | 11/2012 | Cohen et al. |
| 8,313,434 | B2 | 11/2012 | Brister et al. |
| 8,321,149 | B2 | 11/2012 | Brauker et al. |
| 8,332,008 | B2 | 12/2012 | Goode et al. |
| 8,346,338 | B2 | 1/2013 | Goode, Jr. et al. |
| 8,364,229 | B2 | 1/2013 | Simpson et al. |
| 8,369,919 | B2 | 2/2013 | Kamath et al. |
| 8,374,667 | B2 | 2/2013 | Brauker et al. |
| 8,386,004 | B2 | 2/2013 | Kamath et al. |
| 8,394,021 | B2 | 3/2013 | Goode et al. |
| 9,317,657 | B2 | 4/2016 | Breton et al. |
| 10,419,786 | B1* | 9/2019 | Choi ................. H04N 21/8456 |
| 10,453,573 | B2 | 10/2019 | Greene et al. |
| 11,145,410 | B2* | 10/2021 | Greene .................. G01N 33/48 |
| 2003/0032874 | A1 | 2/2003 | Rhodes et al. |
| 2003/0233257 | A1* | 12/2003 | Matian .................. G16H 15/00 |
| | | | 705/3 |
| 2003/0233366 | A1* | 12/2003 | Kesselman ......... G06F 16/2358 |
| 2005/0033132 | A1 | 2/2005 | Shults et al. |
| 2005/0038680 | A1 | 2/2005 | McMahon |
| 2005/0051427 | A1 | 3/2005 | Brauker et al. |
| 2005/0055243 | A1 | 3/2005 | Arndt et al. |
| 2005/0056552 | A1 | 3/2005 | Simpson et al. |
| 2005/0090607 | A1 | 4/2005 | Tapsak et al. |
| 2005/0176136 | A1 | 8/2005 | Burd et al. |
| 2005/0182451 | A1 | 8/2005 | Griffin et al. |
| 2005/0192557 | A1 | 9/2005 | Brauker et al. |
| 2005/0203360 | A1 | 9/2005 | Brauker et al. |
| 2005/0245799 | A1 | 11/2005 | Brauker et al. |
| 2006/0010098 | A1* | 1/2006 | Goodnow .......... G06F 13/4068 |
| 2006/0015020 | A1 | 1/2006 | Neale et al. |
| 2006/0016700 | A1 | 1/2006 | Brister et al. |
| 2006/0020188 | A1 | 1/2006 | Kamath et al. |
| 2006/0020190 | A1 | 1/2006 | Kamath et al. |
| 2006/0020191 | A1 | 1/2006 | Brister et al. |
| 2006/0020192 | A1 | 1/2006 | Brister et al. |
| 2006/0036140 | A1 | 2/2006 | Brister et al. |
| 2006/0036143 | A1 | 2/2006 | Brister et al. |
| 2006/0040402 | A1 | 2/2006 | Brauker et al. |
| 2006/0068208 | A1 | 3/2006 | Tapsak et al. |
| 2006/0142651 | A1 | 6/2006 | Brister et al. |
| 2006/0155180 | A1 | 7/2006 | Brister et al. |
| 2006/0198864 | A1 | 9/2006 | Shults et al. |
| 2006/0200020 | A1 | 9/2006 | Brister et al. |
| 2006/0200022 | A1 | 9/2006 | Brauker et al. |
| 2006/0200970 | A1 | 9/2006 | Brister et al. |
| 2006/0204536 | A1 | 9/2006 | Shults et al. |
| 2006/0224108 | A1 | 10/2006 | Brauker et al. |
| 2006/0235285 | A1 | 10/2006 | Brister et al. |
| 2006/0249381 | A1 | 11/2006 | Petisce et al. |
| 2006/0252027 | A1 | 11/2006 | Petisce et al. |
| 2006/0253012 | A1 | 11/2006 | Petisce et al. |
| 2006/0257995 | A1 | 11/2006 | Simpson et al. |
| 2006/0258761 | A1 | 11/2006 | Boock et al. |
| 2006/0263763 | A1 | 11/2006 | Simpson et al. |
| 2006/0270922 | A1 | 11/2006 | Brauker et al. |
| 2006/0270923 | A1 | 11/2006 | Brauker et al. |
| 2007/0016449 | A1 | 1/2007 | Cohen et al. |
| 2007/0027370 | A1 | 2/2007 | Brauker et al. |
| 2007/0032706 | A1 | 2/2007 | Kamath et al. |
| 2007/0032718 | A1 | 2/2007 | Shults et al. |
| 2007/0033074 | A1* | 2/2007 | Nitzan .................. G16H 20/17 |
| | | | 705/3 |
| 2007/0045902 | A1 | 3/2007 | Brauker et al. |
| 2007/0059196 | A1 | 3/2007 | Brister et al. |
| 2007/0066873 | A1 | 3/2007 | Kamath et al. |
| 2007/0173709 | A1 | 7/2007 | Petisce et al. |
| 2007/0173710 | A1 | 7/2007 | Petisce et al. |
| 2007/0179975 | A1 | 8/2007 | Teh et al. |
| 2007/0208245 | A1 | 9/2007 | Brauker et al. |
| 2007/0208246 | A1 | 9/2007 | Brauker et al. |
| 2007/0232876 | A1 | 10/2007 | Otto et al. |
| 2007/0232879 | A1 | 10/2007 | Brister et al. |
| 2007/0255116 | A1 | 11/2007 | Mehta et al. |
| 2008/0045824 | A1 | 2/2008 | Tapsak et al. |
| 2008/0071580 | A1 | 3/2008 | Marcus et al. |
| 2008/0083617 | A1 | 4/2008 | Simpson et al. |
| 2008/0086044 | A1 | 4/2008 | Brister et al. |
| 2008/0108942 | A1 | 5/2008 | Brister et al. |
| 2008/0119703 | A1 | 5/2008 | Brister et al. |
| 2008/0119704 | A1 | 5/2008 | Brister et al. |
| 2008/0119705 | A1 | 5/2008 | Patel et al. |
| 2008/0119706 | A1 | 5/2008 | Brister et al. |
| 2008/0126988 | A1 | 5/2008 | Mudaliar |
| 2008/0183061 | A1 | 7/2008 | Goode et al. |
| 2008/0183399 | A1 | 7/2008 | Goode et al. |
| 2008/0188731 | A1 | 8/2008 | Brister et al. |
| 2008/0189051 | A1 | 8/2008 | Goode et al. |
| 2008/0194938 | A1 | 8/2008 | Brister et al. |
| 2008/0197024 | A1 | 8/2008 | Simpson et al. |
| 2008/0200788 | A1 | 8/2008 | Brister et al. |
| 2008/0200789 | A1 | 8/2008 | Brister et al. |
| 2008/0200791 | A1 | 8/2008 | Simpson et al. |
| 2008/0214915 | A1 | 9/2008 | Brister et al. |
| 2008/0228054 | A1 | 9/2008 | Shults et al. |
| 2008/0242961 | A1 | 10/2008 | Brister et al. |
| 2008/0249470 | A1 | 10/2008 | Malave et al. |
| 2008/0262469 | A1 | 10/2008 | Brister et al. |
| 2008/0275313 | A1 | 11/2008 | Brister et al. |
| 2008/0287765 | A1 | 11/2008 | Rasdal et al. |
| 2008/0306368 | A1 | 12/2008 | Goode, Jr. et al. |
| 2008/0306434 | A1 | 12/2008 | Dobbles et al. |
| 2008/0306435 | A1 | 12/2008 | Kamath et al. |
| 2008/0306444 | A1 | 12/2008 | Brister et al. |
| 2009/0018424 | A1 | 1/2009 | Kamath et al. |
| 2009/0030294 | A1 | 1/2009 | Petisce et al. |
| 2009/0036758 | A1 | 2/2009 | Brauker et al. |
| 2009/0036763 | A1 | 2/2009 | Brauker et al. |
| 2009/0043181 | A1 | 2/2009 | Brauker et al. |
| 2009/0043182 | A1 | 2/2009 | Brauker et al. |
| 2009/0043525 | A1 | 2/2009 | Brauker et al. |
| 2009/0045055 | A1 | 2/2009 | Rhodes et al. |
| 2009/0062633 | A1 | 3/2009 | Brauker et al. |
| 2009/0062635 | A1 | 3/2009 | Brauker et al. |
| 2009/0076360 | A1 | 3/2009 | Brister et al. |
| 2009/0099436 | A1 | 4/2009 | Brister et al. |
| 2009/0099866 | A1 | 4/2009 | Newman |
| 2009/0099867 | A1* | 4/2009 | Newman ................ G16H 40/20 |
| | | | 705/2 |
| 2009/0124877 | A1 | 5/2009 | Goode, Jr. et al. |
| 2009/0124879 | A1 | 5/2009 | Brister et al. |
| 2009/0124964 | A1 | 5/2009 | Leach et al. |
| 2009/0131769 | A1 | 5/2009 | Leach et al. |
| 2009/0131777 | A1 | 5/2009 | Simpson et al. |
| 2009/0137886 | A1 | 5/2009 | Shariati et al. |
| 2009/0137887 | A1 | 5/2009 | Shariati et al. |
| 2009/0143659 | A1 | 6/2009 | Li et al. |
| 2009/0143660 | A1 | 6/2009 | Brister et al. |
| 2009/0156919 | A1 | 6/2009 | Brister et al. |
| 2009/0163790 | A1 | 6/2009 | Brister et al. |
| 2009/0177249 | A1 | 7/2009 | Roberts et al. |
| 2009/0178459 | A1 | 7/2009 | Li et al. |
| 2009/0192366 | A1 | 7/2009 | Mensinger et al. |
| 2009/0192380 | A1 | 7/2009 | Shariati et al. |
| 2009/0192722 | A1 | 7/2009 | Shariati et al. |
| 2009/0192724 | A1 | 7/2009 | Brauker et al. |
| 2009/0192751 | A1 | 7/2009 | Kamath et al. |
| 2009/0203981 | A1 | 8/2009 | Brauker et al. |
| 2009/0216103 | A1 | 8/2009 | Brister et al. |
| 2009/0240120 | A1 | 9/2009 | Mensinger et al. |
| 2009/0240193 | A1 | 9/2009 | Mensinger et al. |
| 2009/0242399 | A1 | 10/2009 | Kamath et al. |
| 2009/0242425 | A1 | 10/2009 | Kamath et al. |
| 2009/0247855 | A1 | 10/2009 | Boock et al. |
| 2009/0247856 | A1 | 10/2009 | Boock et al. |
| 2009/0259493 | A1 | 10/2009 | Venon et al. |
| 2009/0287074 | A1 | 11/2009 | Shults et al. |

(56)         References Cited

U.S. PATENT DOCUMENTS

| | | |
|---|---|---|
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0030484 A1 | 2/2010 | Brauker et al. |
| 2010/0036215 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0076283 A1 | 3/2010 | Simpson et al. |
| 2010/0076784 A1* | 3/2010 | Greenburg .............. G06Q 10/10 705/3 |
| 2010/0081908 A1 | 4/2010 | Dobbles et al. |
| 2010/0081910 A1 | 4/2010 | Brister et al. |
| 2010/0082364 A1 | 4/2010 | Taub et al. |
| 2010/0087724 A1 | 4/2010 | Brauker et al. |
| 2010/0095229 A1 | 4/2010 | Dixon et al. |
| 2010/0096259 A1 | 4/2010 | Zhang et al. |
| 2010/0121169 A1 | 5/2010 | Petisce et al. |
| 2010/0161269 A1 | 6/2010 | Kamath et al. |
| 2010/0161346 A1 | 6/2010 | Getschmann et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168657 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185075 A1 | 7/2010 | Brister et al. |
| 2010/0191082 A1 | 7/2010 | Brister et al. |
| 2010/0198035 A1 | 8/2010 | Kamath et al. |
| 2010/0198036 A1 | 8/2010 | Kamath et al. |
| 2010/0198314 A1 | 8/2010 | Wei |
| 2010/0212583 A1 | 8/2010 | Brister et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode, Jr. et al. |
| 2010/0240976 A1 | 9/2010 | Goode, Jr. et al. |
| 2010/0261987 A1 | 10/2010 | Kamath et al. |
| 2010/0268053 A1 | 10/2010 | Ghesquiere et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0312577 A1 | 12/2010 | Goodnow et al. |
| 2010/0324403 A1 | 12/2010 | Brister et al. |
| 2010/0331656 A1 | 12/2010 | Mensinger et al. |
| 2011/0004085 A1 | 1/2011 | Mensinger et al. |
| 2011/0009727 A1 | 1/2011 | Mensinger et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0046467 A1 | 2/2011 | Simpson et al. |
| 2011/0077490 A1 | 3/2011 | Simpson et al. |
| 2011/0077493 A1 | 3/2011 | Shadforth et al. |
| 2011/0118579 A1 | 5/2011 | Goode, Jr. et al. |
| 2011/0119080 A1 | 5/2011 | Hayter et al. |
| 2011/0124992 A1 | 5/2011 | Brauker et al. |
| 2011/0125410 A1 | 5/2011 | Goode, Jr. et al. |
| 2011/0126142 A1 | 5/2011 | Zhou et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0144465 A1 | 6/2011 | Shults et al. |
| 2011/0178378 A1 | 7/2011 | Brister et al. |
| 2011/0184752 A1 | 7/2011 | Ray et al. |
| 2011/0190614 A1 | 8/2011 | Brister et al. |
| 2011/0201910 A1 | 8/2011 | Rasdal et al. |
| 2011/0201911 A1 | 8/2011 | Johnson et al. |
| 2011/0218414 A1 | 9/2011 | Kamath et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0263958 A1 | 10/2011 | Brauker et al. |
| 2011/0264378 A1 | 10/2011 | Breton et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0290645 A1 | 12/2011 | Brister et al. |
| 2011/0313543 A1 | 12/2011 | Brauker et al. |
| 2011/0320130 A1 | 12/2011 | Valdes et al. |
| 2012/0016305 A1 | 1/2012 | Jollota et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0108934 A1 | 5/2012 | Valdes et al. |
| 2012/0130214 A1 | 5/2012 | Brister et al. |
| 2012/0172691 A1 | 7/2012 | Brauker et al. |
| 2012/0172694 A1 | 7/2012 | Desborough et al. |
| 2012/0179014 A1 | 7/2012 | Shults et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0203467 A1 | 8/2012 | Kamath et al. |
| 2012/0209098 A1 | 8/2012 | Goode, Jr. et al. |
| 2012/0215086 A1 | 8/2012 | Kamath et al. |
| 2012/0215087 A1 | 8/2012 | Cobelli et al. |
| 2012/0215201 A1 | 8/2012 | Brauker et al. |
| 2012/0215461 A1 | 8/2012 | Goode, Jr. et al. |
| 2012/0215462 A1 | 8/2012 | Goode, Jr. et al. |
| 2012/0215496 A1 | 8/2012 | Kamath et al. |
| 2012/0220979 A1 | 8/2012 | Brauker et al. |
| 2012/0226121 A1 | 9/2012 | Kamath et al. |
| 2012/0228134 A1 | 9/2012 | Simpson et al. |
| 2012/0238852 A1 | 9/2012 | Brauker et al. |
| 2012/0245447 A1 | 9/2012 | Karan et al. |
| 2012/0245448 A1 | 9/2012 | Shariati et al. |
| 2012/0245855 A1 | 9/2012 | Kamath et al. |
| 2012/0246106 A1 | 9/2012 | Atlas et al. |
| 2012/0255875 A1 | 10/2012 | Mcente et al. |
| 2012/0258748 A1 | 10/2012 | San Vicente et al. |
| 2012/0259191 A1 | 10/2012 | Shariati et al. |
| 2012/0260323 A1 | 10/2012 | San Vicente et al. |
| 2012/0262298 A1 | 10/2012 | Bohm et al. |
| 2012/0265035 A1 | 10/2012 | Bohm et al. |
| 2012/0265036 A1 | 10/2012 | Estes et al. |
| 2012/0265037 A1 | 10/2012 | Bohm et al. |
| 2012/0277562 A1 | 11/2012 | Brister et al. |
| 2012/0277566 A1 | 11/2012 | Kamath et al. |
| 2012/0283541 A1 | 11/2012 | Kamath et al. |
| 2012/0283543 A1 | 11/2012 | Brauker et al. |
| 2012/0296311 A1 | 11/2012 | Brauker et al. |
| 2012/0302854 A1 | 11/2012 | Kamath et al. |

(56)     References Cited

U.S. PATENT DOCUMENTS

| | | | |
|---|---|---|---|
| 2012/0302855 A1 | 11/2012 | Kamath et al. | |
| 2012/0323100 A1 | 12/2012 | Kamath et al. | |
| 2013/0012798 A1 | 1/2013 | Brister et al. | |
| 2013/0030273 A1 | 1/2013 | Tapsak et al. | |
| 2013/0035575 A1 | 2/2013 | Mayou et al. | |
| 2013/0035865 A1 | 2/2013 | Mayou et al. | |
| 2013/0035871 A1 | 2/2013 | Mayou et al. | |
| 2013/0321425 A1 | 12/2013 | Greene et al. | |
| 2013/0325352 A1 | 12/2013 | Greene et al. | |
| 2013/0325504 A1* | 12/2013 | Greene | G06T 11/206 |
| | | | 705/3 |
| 2014/0067421 A1 | 3/2014 | Bernstein et al. | |
| 2014/0088392 A1 | 3/2014 | Bernstein et al. | |
| 2014/0088393 A1 | 3/2014 | Bernstein et al. | |
| 2014/0148665 A1* | 5/2014 | Bernstein | A61B 5/1473 |
| | | | 600/365 |
| 2014/0250374 A1* | 9/2014 | Ohki | G06F 3/0488 |
| | | | 715/247 |
| 2014/0321425 A1 | 10/2014 | Mueck et al. | |
| 2016/0078190 A1 | 3/2016 | Greene et al. | |
| 2019/0295715 A1 | 9/2019 | Greene et al. | |
| 2020/0005937 A1 | 1/2020 | Greene et al. | |
| 2021/0407664 A1* | 12/2021 | Greene | G16H 15/00 |
| 2023/0341422 A1* | 10/2023 | Vajaria | G01N 33/70 |
| 2024/0282419 A1* | 8/2024 | Farri | G06F 16/345 |
| 2024/0312620 A1* | 9/2024 | Greene | G06T 11/206 |

FOREIGN PATENT DOCUMENTS

| | | | |
|---|---|---|---|
| CN | 101467878 A | 7/2009 | |
| CN | 102012390 A | 4/2011 | |
| CN | 102405011 A | 4/2012 | |
| EP | 2348433 A2 | 7/2011 | |
| EP | 2856367 B1 | 8/2021 | |
| JP | 2002085556 A | 3/2002 | |
| JP | 2003162580 A | 6/2003 | |
| JP | 2005025747 A | 1/2005 | |
| JP | 2005287837 A | 10/2005 | |
| JP | 2007304088 A | 11/2007 | |
| JP | 2010507138 A | 3/2010 | |
| JP | 2010082009 A | 4/2010 | |
| JP | 2011113564 A | 6/2011 | |
| JP | 2011147784 A | 8/2011 | |
| JP | 7416859 B2 | 1/2024 | |
| WO | 2009023634 A2 | 2/2009 | |
| WO | 2011026053 A1 | 3/2011 | |
| WO | 2011051922 A2 | 5/2011 | |
| WO | 2012067854 A2 | 5/2012 | |
| WO | 2012108935 A1 | 8/2012 | |
| WO | 2012108936 A1 | 8/2012 | |
| WO | 2012108938 A1 | 8/2012 | |
| WO | 2012108939 A1 | 8/2012 | |
| WO | 2012108940 A1 | 8/2012 | |
| WO | 2012145027 A1 | 10/2012 | |
| WO | 2013184566 A2 | 12/2013 | |

OTHER PUBLICATIONS

International Search Report and Written Opinion for Application No. PCT/US2013/043869 mailed on Aug. 7, 2013, 6 pages.

* cited by examiner

RECEIVE A REQUEST TO GENERATE A REPORT — 715

SELECT ONE OR MORE MODULES BASED ON METADATA — 720

GENERATE THE REQUESTED REPORT BASED ON THE SELECTED MODULES — 725

DEVICES USED                                    _733A_                                    device clock is ...

Continuous Glucose Monitor: Dexcom Seven                                                 off by 35 minutes DEVICES USED                                    _733B_                                    device clock is ...

Blood Glucose Meter: SMBG Device                                                         off by 13 days DEVICES USED                                    _733C_                                    device clock is ...

Continuous Glucose Monitor: Dexcom Seven                                                 off by 35 minutes Blood Glucose Meter: SMBG Device                                                         correct

FIG. 6A-10

DAILY SUMMARY *650*   *600*   *652A* — for about the past month

This summary is showing glucose data for about the past month, collapsed into a 24 hour period. The dark line is the median glucose, while the middle 50% of all glucose values is lightly shaded. The target range, shaded as a bar across the graph, is between 70 to 180mg/dL.

Glucose Median ± 25%

| | Night 11:00-5:00am | Morning 5:00-11:00am | Midday 11:00-1:30pm | Afternoon 1:30-5:30pm | Evening 5:30-11:00pm |
|---|---|---|---|---|---|
| | 04AM | 06AM | 12PM | 04 PM | 08 PM |
| Within Range | 58% | 62% | 50% | 60% | 62% |
| Median | 164 | 156 | 181 | 161 | 161 |
| Middle 50% | 131 to 205 | 118 to 202 | 132 to 233 | 112 to 208 | 127 to 198 |
| Variability | Moderate (cv: 36%) | Moderate (cv: 34%) | Moderate (cv: 37%) | Moderate (cv: 38%) | Moderate (cv: 30%) |

Glucose (dg/ml)

FIG. 6A-13

GLUCOSE VALUES    674A                    674B                    for the past 26 days This section highlights each individual blood glucose meter test. Some of the values that are outside of the target glucose range of the 70 to 80 mg/dL might be highlighted. Circles ● highlight the highest 10% of values that are already out of range, while square ■ highlight the lowest 10% of values that are already out of range.

|  | 12am | 1 | 2 | 3 | 4 | 5 | 6 | 7 | 8 | 9 | 10 | 11 | 12am | 1 | 2 | 3 | 4 | 5 | 6 | 7 | 8 | 9 | 10 | 11 | Average | Variability |
|---|---|---|---|---|---|---|---|---|---|---|---|---|---|---|---|---|---|---|---|---|---|---|---|---|---|---|
| Mon, Dec 03, '07 |  |  |  |  |  | 674D |  | 273● |  | 159 |  |  |  |  |  |  |  |  |  |  |  |  |  |  | 216 | - |
| Sun, Dec 02, '07 |  |  |  |  |  |  |  | 260 | 674C 261 |  |  |  |  |  |  |  |  |  |  |  |  |  |  |  | 261 | - |
| Sat, Dec 01, '07 |  |  |  |  |  |  |  |  | 108 48■ |  |  |  |  |  |  | 82 |  | 59 |  |  |  |  |  |  | 75 | 35% |
| Fri, Nov 30, '07 |  |  |  |  | 215 | 143 | 128 | 674Z | 294● | 58■ 65 |  | 127 |  | 109 |  |  |  |  |  |  |  |  |  |  | 142 | 55% |
| Thu, Nov 29, '07 |  |  |  |  |  | 267 |  |  |  |  |  |  | 255 |  | 163 | 242 |  |  |  |  |  |  |  |  | 232 | 20% |
| Wed, Nov 28, '07 |  |  | 244 |  | 238 |  |  |  |  |  |  | 101 | 72 |  | 57■ |  |  |  |  |  |  |  |  |  | 142 | 64% |
| Tue, Nov 27, '07 |  |  |  | 290● |  |  |  |  |  |  |  |  | 152 |  | 75 |  |  |  |  |  |  |  |  |  | 172 | 63% |
| Mon, Nov 26, '07 |  |  |  |  |  |  |  |  |  |  |  |  | 76 |  | 55■ | 83 |  |  |  |  |  |  |  |  | 71 | 20% |
| Sun, Nov 25, '07 |  |  |  |  |  |  |  |  |  |  |  |  |  |  |  |  |  |  |  |  |  |  |  |  |  |  |
| Sat, Nov 24, '07 | 333● |  |  |  | 51■ |  |  |  |  |  |  |  |  |  |  |  |  |  |  |  |  |  |  |  | 192 | - |
| Fri, Nov 23, '07 |  |  |  |  |  | 132 |  | 86 |  |  |  | 132 |  |  |  |  |  |  |  |  |  |  |  |  | 117 | 23% |
| Thu, Nov 22, '07 |  |  |  | 328● |  |  |  | 159 |  | 77 |  | 67 |  | 107 | 137 |  |  |  |  |  |  |  |  |  | 145 | 65% |
| Wed, Nov 21, '07 |  |  |  |  | 171 |  |  |  | 140 |  | 74 |  | 113 |  |  |  |  |  |  |  |  |  |  |  | 125 | 33% |
| Tue, Nov 20, '07 |  |  | 261 | 91 |  |  |  |  | 862● | 56■ | 63 |  |  |  |  |  |  |  |  |  |  |  |  |  | 167 | 83% |
| Mon, Nov 19, '07 |  | 56■ |  | 241 227 153 |  |  |  |  | 117 | 162 | 97 |  | 131 |  |  |  |  |  |  |  |  |  |  |  | 148 | 42% |
| Sun, Nov 18, '07 |  |  |  |  | 271 |  |  |  | 135 | 125 150 |  |  |  |  |  |  |  |  |  |  |  |  |  |  | 170 | 40% |
| Sat, Nov 17, '07 |  |  | 173 |  | 162 48■ |  | 59 |  | 154 |  | 86 |  |  |  |  |  |  |  |  |  |  |  |  |  | 114 | 49% |
| Fri, Nov 16, '07 |  |  | 589● | 137 | 125 | 86 | 160 219 193 141 |  | 61 |  |  |  |  |  |  |  |  |  |  |  |  |  |  |  | 162 | 51% |
| Thu, Nov 15, '07 |  |  | 201 154 |  |  |  | 226 | 143 |  | 91 | 96 |  |  |  |  |  |  |  |  |  |  |  |  |  | 152 | 36% |
| Wed, Nov 14, '07 | 63 |  |  | 215 |  |  |  |  | 72 |  | 104 |  |  |  |  |  |  |  |  |  |  |  |  |  | 114 | 62% |
| Tue, Nov 13, '07 |  |  | 302● | 124 |  |  | 152 | 248 224 |  | 164 |  |  |  |  |  |  |  |  |  |  |  |  |  |  | 202 | 33% |
| Mon, Nov 12, '07 | 44■ |  | 169 149 |  |  |  |  |  | 279● |  | 52■ |  |  |  |  |  |  |  |  |  |  |  |  |  | 139 | 70% |

FIG. 6A-26

GLUCOSE METER VALUES     *674AA*                                    for the past 26 days This section highlights each individual blood glucose meter test. The values that are outside of the target glucose range of 70 to 180 mg/dL and are outliers will be highlighted.

```
              12am 1  2  3  4  5  6  7  8  9  10 11 12am 1  2  3  4  5  6  7  8  9  10 11
Mon, Dec 03                          674AB — ▲273        159

12am 1  2  3  4  5  6  7  8  9  10 11 12am 1  2  3  4  5  6  7  8  9  10 11
Sun, Dec 02                                    260                 261
```

Sat                                          106  ▼49 — 674AC              82         59

Fri                              215  143  128        ▲294    ▼58            127          109
                                                              65

Thu                                   267                            255            163 242

Wed                       244        236                              101   72   ▼57

Tue                            ▲290                                  152          75

Mon                                                          76        ▼55       83

```
              12am 1  2  3  4  5  6  7  8  9  10 11 12am 1  2  3  4  5  6  7  8  9  10 11
Sun, Nov 25
```

Sat     ▲633              ▼51

Fri                                  132        86                    132

Thu                       ▲328              159            77         67         107 137

Wed                                  171                   140              74            113

Tue                            261   91                    ▲362  ▼56        63

Mon        ▼56                  241  153                        117  162    97          131
                               227

```
              12am 1  2  3  4  5  6  7  8  9  10 11 12am 1  2  3  4  5  6  7  8  9  10 11
Sun, Nov 25                             271                       135   125 150
```

Sat                            173        162  ▼43        59         154        86

Fri                            ▲339  137        125  86      160    219 141      61
                                                            193

Thu                       201                             226   143         91   96
                          154

Wed     63                     215                              72          104

Tue                       ▲302        124              152  248  224        164

Mon           ▼44                169                            ▲279       ▼52
                                149

```
              12am 1  2  3  4  5  6  7  8  9  10 11 12am 1  2  3  4  5  6  7  8  9  10 11
Sun, Nov 25                          170                             177 171   ▲397
```

Sat        ▼55                  ▲317  134  132              121 270      59   83

Fri                            209   ▼57       119   80              168      111
                                     225

Mon           ▲329       ▼49        104  211              190       254 259       106

FIG. 6A-27

REPORT LEGEND                    6874

• The report was generated from glucose values collected between Mar 6 and Apr 6, 2012

• In the visualizations with multiple shades, the lighter shades are more ideal, and the darker shades are less ideal

DAYS OF INTEREST

Most within range:

Saturdays
Mean: 119, cv: 18%

Highest:

Sundays
Mean: 155, cv: 8%

Most variable:

Tuesdays
Mean: 152, cv: 45%

Lowest:

Thursdays
Mean: 116, cv: 24%

FIG. 10

DYNAMIC REPORT BUILDING

CROSS-REFERENCE TO RELATED APPLICATIONS

This application is a continuation of U.S. application Ser. No. 17/470,364 (filed on Sep. 9, 2021), which is a continuation of U.S. application Ser. No. 16/565,286 (filed on Sep. 9, 2019; now U.S. Pat. No. 11,145,410), which is a continuation of U.S. application Ser. No. 13/789,339 (filed on Mar. 7, 2013; now U.S. Pat. No. 10,453,573), which is a continuation of U.S. application Ser. No. 13/788,375 (filed on Mar. 7, 2013), which claims the benefit of U.S. Application No. 61/655,991 (filed on Jun. 5, 2012), the disclosures of which are incorporated herein by reference in their entirety.

BACKGROUND

The present disclosure generally relates to data processing of glucose data of a host.

Diabetes mellitus is a disorder in which the pancreas cannot create sufficient insulin, such as in the case of Type I diabetes and/or in which insulin is not effective, such as Type 2 diabetes. In a diabetic state, a victim suffers from high blood sugar, which causes an array of physiological derangements, such as kidney failure, skin ulcers, or bleeding into the vitreous of the eye, associated with the deterioration of small blood vessels. A hypoglycemic reaction, such as low blood sugar, may be induced by an inadvertent overdose of insulin, or after a normal dose of insulin or glucose-lowering agent accompanied by extraordinary exercise or insufficient food intake.

A diabetic person may carry a self-monitoring blood glucose (SMBG) monitor, which typically requires uncomfortable finger pricking methods. Due to the lack of comfort and convenience, a diabetic typically measures his or her glucose level only two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is higher or lower based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display, to allow presentation of information to a user hosting the sensor.

SUMMARY

Methods and apparatus, including computer program products, are provided for processing analyte data. In some exemplary implementations, there is provided an apparatus for dynamic report generation. The apparatus may include at least one processor and at least one memory including computer program code configured to provide at least selecting at least one module from among a plurality of modules, the selection performed based on metadata including one or more of the following rules: whether the at least one module can be used with a type of device, whether the at least one module can be used with a glycemic state of a host, and whether the at least one module can be used with an expected volume of data generated by the type of device; and generating a report including the selected at least one module configured to present information representative of the glucose concentration level measured in the host.

In some exemplary implementations, there is provided a method for dynamic report generation. The method may include receiving a request to generate a report; selecting, in response to the request, at least one module from among a plurality of modules, the selection performed based on metadata including information representative of at least one of the host and a type of device being used to measure the glucose concentration level; generating the report including the selected at least one module configured to present within a single view information representative of the glucose concentration level measured in the host; and providing the generated report to a user interface for presentation, wherein the receiving, the selecting, the generated, and the providing are implemented by at least one processor.

In some exemplary implementations, there is provided a computer-readable storage medium including code which when executed by the at least one processor provides at least receiving a request to generate a report; selecting at least one module from among a plurality of modules stored in a repository, the selection performed based on metadata including information representative of at least one of a host, a type of device being used to measure a glucose concentration level of the host, and at least one rule; generating the report including the selected at least one module configured to present information representative of the glucose concentration level measured in the host; and providing the generated report to a user interface for presentation.

In some implementations, the above-noted aspects may further include additional features described herein including one or more of the following. The information representative of the host may further include at least one of a user preference for the at least one module and host identification information. The metadata may further include one or more rules. The user preference may include a preference provided by the host, a health care provider, and a processor programmatically based on the metadata. The type of device may include at least one of a continuous blood glucose monitor or a self-monitoring blood glucose monitor. The one or more rules may include one or more of the following rules: whether the at least one module can be used with the type of device, whether the at least one module can be used with a glycemic state of the host, and whether the at least one module can be used with an expected volume of data provided by the type of device. The generating may further include accessing, from a repository, the metadata including a template defining a placement of the selected at least one module. The single view may graphically highlight when the glucose concentration level measured in the host is at least one of above, below, or within a predetermined target range of the glucose concentration level of the host. The selecting may further include selecting the at least one module from among a plurality of modules stored in a repository coupled to the at least one processor, when the metadata indicates the at least one module is configured for use with a continuous blood glucose monitor. The selecting may further include selecting another module from among a plurality of modules, when the metadata indicates the at least one module is not configured for use with the continuous blood glucose monitor and the other module is configured for use with the continuous blood glucose monitor. The selecting may further include selecting the at least one module from among a plurality of modules, when the metadata indicates the at least one module is configured for use with a certain size display for presenting the report. The selecting may further include selecting the at least one module from among a plurality of modules, when the metadata indicates the at least one module is configured for use with the expected volume of data generated by a continuous blood glucose monitor. The selecting may further include selecting the at least one module from among a plurality of modules, when the metadata indicates the at least one module is configured for use with the glycemic state of the host comprising a high glycemic state, the selected at least one module providing a view indicative of the high glycemic state. The selecting may further include selecting the at least one module from among a plurality of modules, when the metadata indicates a user preference for the selected at least one module. The selecting may be dynamically selected based an evaluation of the metadata stored in a repository coupled to the at least one processor, when the request is received.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

DESCRIPTION OF THE DRAWINGS

In the drawings,

FIG. 6A-1 depict an example of a report template generated in accordance with some exemplary implementations;

FIG. 6A-2 depicts an example process of dynamically selecting report modules in accordance with some exemplary implementations;

FIGS. 6A-3 through 6A-28 depict examples of report modules in accordance with some exemplary implementations;

FIGS. 7-10 depict additional examples of report modules in accordance with some exemplary implementations; and FIG. 11 depicts an example of a process for processing analyte data in accordance with some exemplary implementations.

Figure 1:
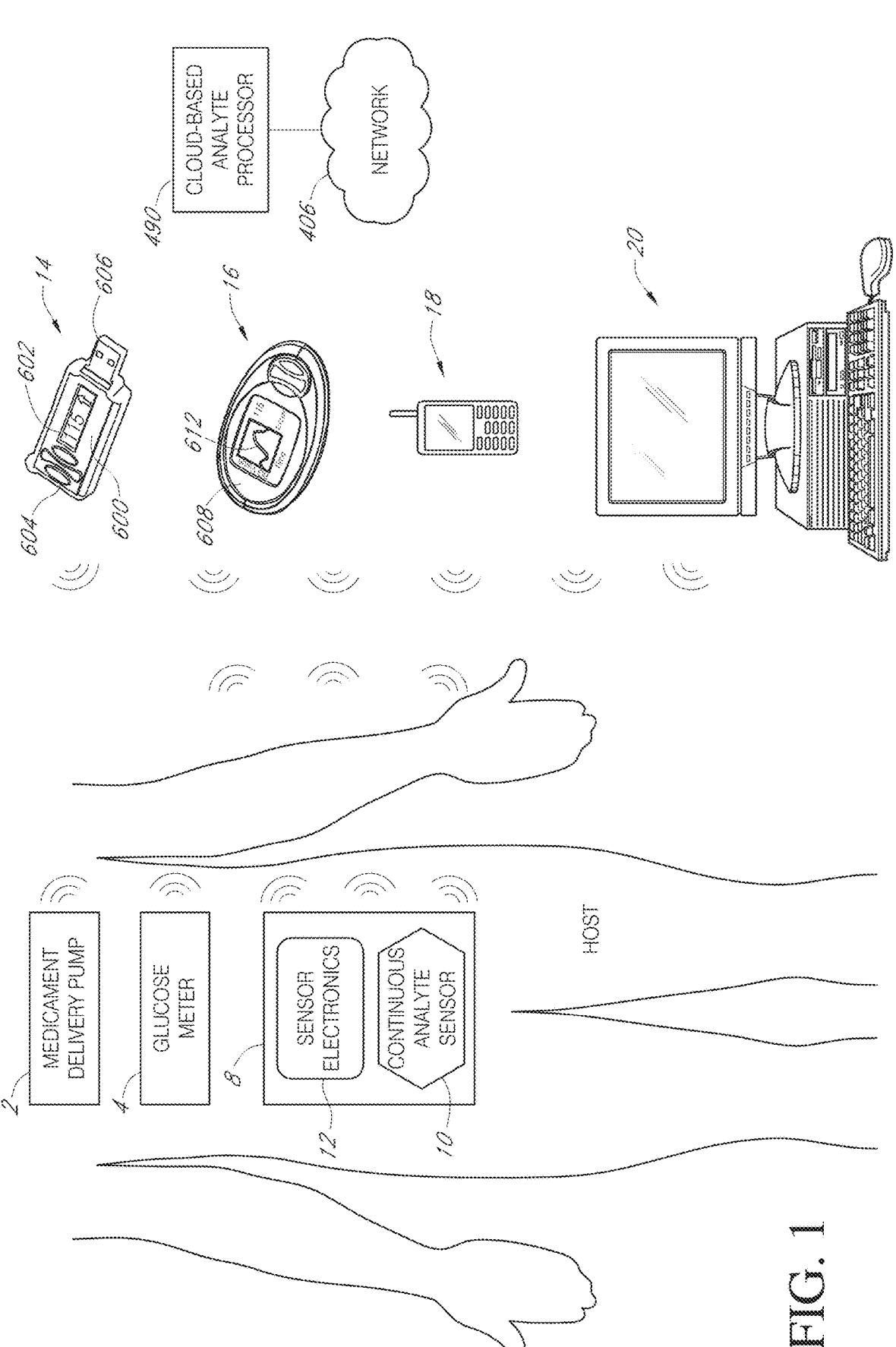
FIG. 1 depicts a diagram illustrating a continuous analyte sensor system including a sensor electronics module in accordance with some exemplary implementations.

Like labels are used to refer to same or similar items in the drawings.

DETAILED DESCRIPTION

FIG. 1 depicts an example system 100, in accordance with some exemplary implementations. The system 100 includes a continuous analyte sensor system 8 including a sensor electronics module 12 and a continuous analyte sensor 10. The system 100 may include other devices and/or sensors, such as medicament delivery pump 2 and glucose meter 4. The continuous analyte sensor 10 may be physically connected to sensor electronics module 12 and may be integral with (e.g., non-releasably attached to) or releasably attachable to the continuous analyte sensor 10. The sensor electronics module 12, medicament delivery pump 2, and/or glucose meter 4 may couple with one or more devices, such as display devices 14, 16, 18, and/or 20.

In some exemplary implementations, the system 100 may include a cloud-based analyte processor 490 configured to analyze analyte data (and/or other patient related data) provided via network 406 (e.g., via wired, wireless, or a combination thereof) from sensor system 8 and other devices, such as display devices 14-20 and the like, associated with the host (also referred to as a patient) and generate reports providing high-level information, such as statistics, regarding the measured analyte over a certain time frame.

In some exemplary implementations, system 100 may generate reports dynamically. For example, the analyte processor 490 may receive a request to generate a report. In response to the request, the analyte processor 490 may then select at least one module from among a plurality of modules. This selection may be performed based on metadata. The metadata may include information representative of the host, the type of device being used to measure the glucose concentration level, rules, and the like. The selection may be considered dynamic in the sense that module selection varies for each request based on metadata. The report may then be generated to include the at least one selected module and then provided to a user interface for presentation.

Before providing additional details regarding the cloud-based analyte processing system disclosed herein, the following provides a detailed description of the sensors and systems that may provide data to the cloud-based processing system disclosed herein.

In some exemplary implementations, the sensor electronics module 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor. An example implementation of the sensor electronics module 12 is described further below with respect to FIG. 2.

The sensor electronics module 12 may, as noted, couple (e.g., wirelessly and the like) with one or more devices, such as display devices 14, 16, 18, and/or 20. The display devices 14, 16, 18, and/or 20 may be configured for presenting (and/or alarming) information, such as sensor information transmitted by the sensor electronics module 12 for display at the display devices 14, 16, 18, and/or 20.

The display devices may include a relatively small, key fob-like display device 14, a relatively large, hand-held display device 16, a cellular phone (e.g., a smart phone, a tablet, and the like), a computer 20, and/or any other user equipment configured to at least present information (e.g., a medicament delivery information, discrete self-monitoring glucose readings, heart rate monitor, caloric intake monitor, and the like).

In some exemplary implementations, the relatively small, key fob-like display device 14 may comprise a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device) and may be configured to display certain types of displayable sensor information, such as a numerical value and an arrow.

In some exemplary implementations, the relatively large, hand-held display device 16 may comprise a hand-held receiver device, a palm-top computer, and/or the like. This large display device may include a relatively larger display (e.g., larger than the small display device) and may be configured to display information, such as a graphical representation of the continuous sensor data including current and historic sensor data output by sensor system 8.

In some exemplary implementations, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some exemplary implementations, the continuous analyte sensor 10 may analyze a plurality of intermittent blood samples, although other analytes may be used as well.

In some exemplary implementations, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a host. The data stream may be raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

Although the description herein refers to some implementations that include a continuous analyte sensor 10 comprising a glucose sensor, the continuous analyte sensor 10 may comprises other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, Acetyl Co A, triglycerides, fatty acids, intermediaries in the citric acid cycle, choline, insulin, cortisol, testosterone, and the like.

Figure 2:
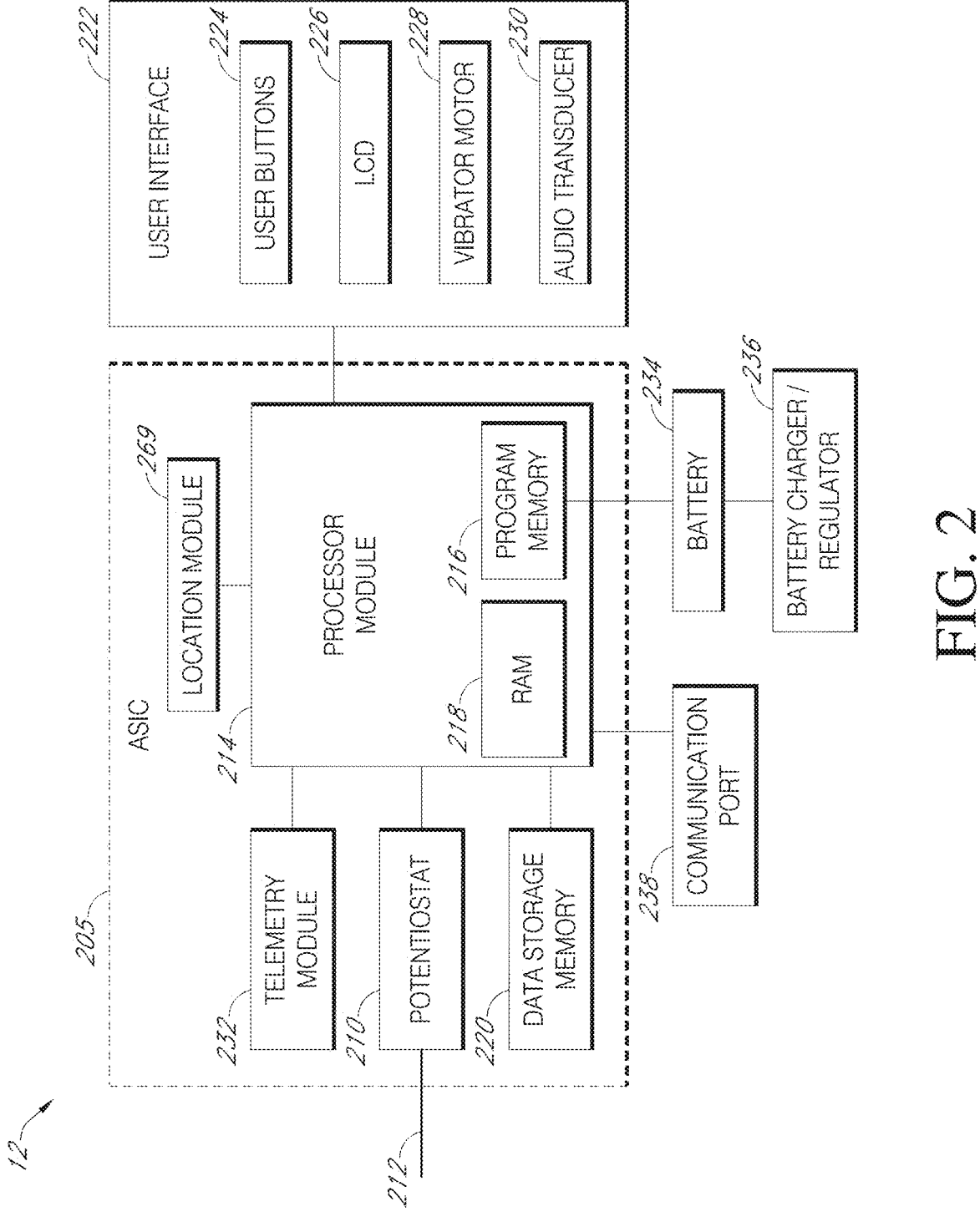
FIG. 2 depicts a block diagram illustrating the sensor electronics module in accordance with some exemplary implementations.

FIG. 2 depicts an example of a sensor electronics module 12, in accordance with some exemplary implementations. The sensor electronics module 12 may include sensor electronics that are configured to process sensor information, such as sensor data, and generate transformed sensor data and displayable sensor information. For example, the sensor electronics module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration information, sensor diagnostic information, location information (which may be provided by a location module 269 providing location information, such as global positioning system information), alarm/alert information, calibration information, smoothing and/or filtering algorithms of sensor data, and/or the like.

In some exemplary implementations, the sensor electronics module 12 may be configured to calibrate the sensor data, and the data storage memory 220 may store the calibrated sensor data points as transformed sensor data. Moreover, the sensor electronics module 12 may be configured, in some exemplary implementations, to wirelessly receive calibration information from a display device, such as devices 14, 16, 18, and/or 20, to enable calibration of the sensor data from sensor 12 and data line 212. Furthermore, the sensor electronics module 12 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms.

In some exemplary implementations, the sensor electronics module 12 may comprise an application-specific integrated circuit (ASIC) 205 coupled to a user interface 122. The ASIC 205 may further include a potentiostat 210, a telemetry module 232 for transmitting data from the sensor electronics module 12 to one or more devices, such devices 14, 16, 18, and/or 20, and/or other components for signal processing and data storage (e.g., processor module 214 and data store 220). Although FIG. 2 depicts ASIC 205, other types of circuitry may be used as well, including field programmable gate arrays (FPGA), one or more microprocessors configured to provide some (if not all) of the processing performed by the sensor electronics module 12, analog circuitry, digital circuitry, or a combination thereof.

In the example depicted at FIG. 2, the potentiostat 210 is coupled to a continuous analyte sensor 10, such as a glucose sensor, via data line 212 to receive sensor data from the analyte. The potentiostat 210 may also provide via data line 212 a voltage to the continuous analyte sensor 10 to bias the sensor for measurement of a value (e.g., a current and the like) indicative of the analyte concentration in a host (also referred to as the analog portion of the sensor). The potentiostat 210 may have one or more channels (and corresponding one or more data lines 212), depending on the number of working electrodes at the continuous analyte sensor 10.

In some exemplary implementations, the potentiostat 210 may include a resistor that translates a current value from the sensor 10 into a voltage value, while in some exemplary implementations, a current-to-frequency converter may also be configured to integrate continuously a measured current value from the sensor 10 using, for example, a charge-counting device. In some exemplary implementations, an analog-to-digital converter may digitize the analog signal from the sensor 10 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics module 12 and one or more other devices, such as display devices, processors, network access devices, and the like. A variety of wireless radio technologies that can be implemented in the telemetry module 232 include Bluetooth, Bluetooth Low-Energy, ANT, ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some exemplary implementations, the telemetry module 232 comprises a Bluetooth chip, although the Bluetooth technology may also be implemented in a combination of the telemetry module 232 and the processor module 214.

The processor module 214 may control the processing performed by the sensor electronics module 12. For example, the processor module 214 may be configured to process data (e.g., counts), from the sensor, filter the data, calibrate the data, perform fail-safe checking, and/or the like.

In some exemplary implementations, the processor module 214 may comprise a digital filter, such as for example an infinite impulse response (IIR) or a finite impulse response (FIR) filter. This digital filter may smooth a raw data stream received from sensor 10, data line 212 and potentiostat 210 (e.g., after the analog-to-digital conversion of the sensor data). Generally, digital filters are programmed to filter data sampled at a predetermined time interval (also referred to as a sample rate). In some exemplary implementations, such as when the potentiostat 210 is configured to measure the analyte (e.g., glucose and the like) at discrete time intervals, these time intervals determine the sampling rate of the digital filter. In some exemplary implementations, the potentiostat 210 is configured to measure continuously the analyte, for example, using a current-to-frequency converter. In these current-to-frequency converter implementations, the processor module 214 may be programmed to request, at predetermined time intervals (acquisition time), digital values from the integrator of the current-to-frequency converter. These digital values obtained by the processor module 214 from the integrator may be averaged over the acquisition time due to the continuity of the current measurement. As such, the acquisition time may be determined by the sampling rate of the digital filter.

The processor module 214 may further include a data generator configured to generate data packages for transmission to devices, such as the display devices 14, 16, 18, and/or 20. Furthermore, the processor module 215 may generate data packets for transmission to these outside sources via telemetry module 232. In some exemplary implementations, the data packages may, as noted, be customizable for each display device, and/or may include any available data, such as a time stamp, displayable sensor information, transformed sensor data, an identifier code for the sensor and/or sensor electronics module, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics module 12 and/or charge the batteries 234.

The program memory 216 may be implemented as a semi-static memory for storing data, such as an identifier for a coupled sensor 10 (e.g., a sensor identifier (ID)) and for storing code (also referred to as program code) to configure the ASIC 205 to perform one or more of the operations/functions described herein. For example, the program code may configure processor module 214 to process data streams or counts, filter, calibrate, perform fail-safe checking, and the like.

The memory 218 may also be used to store information. For example, the processor module 214 including memory 218 may be used as the system's cache memory, where temporary storage is provided for recent sensor data received from data line 212 and potentiostat 210. In some exemplary implementations, the memory may comprise memory storage components, such as read-only memory (ROM), random-access memory (RAM), dynamic-RAM, static-RAM, non-static RAM, easily erasable programmable read only memory (EEPROM), rewritable ROMs, flash memory, and the like.

The data storage memory 220 may be coupled to the processor module 214 and may be configured to store a variety of sensor information. In some exemplary implementations, the data storage memory 220 stores one or more days of continuous analyte sensor data. For example, the data storage memory may store 1, 3, 4, 5, 6, 7, 8, 9, 10, 11, 12, 13, 14, 15, 20, and/or 30 (or more days) of continuous analyte sensor data received from sensor 10 via data line 212. The stored sensor information may include one or more of the following: a time stamp, raw sensor data (one or more raw analyte concentration values), calibrated data, filtered data, transformed sensor data, and/or any other displayable sensor information.

The user interface 222 may include a variety of interfaces, such as one or more buttons 224, a liquid crystal display (LCD) 226, a vibrator 228, an audio transducer (e.g., speaker) 230, a backlight, and/or the like. The components that comprise the user interface 222 may provide controls to interact with the user (e.g., the host). One or more buttons 224 may allow, for example, toggle, menu selection, option selection, status selection, yes/no response to on-screen questions, a "turn off" function (e.g., for an alarm), a "snooze" function (e.g., for an alarm), a reset, and/or the like. The LCD 226 may provide the user with, for example, visual data output. The audio transducer 230 (e.g., speaker) may provide audible signals in response to triggering of certain alerts, such as present and/or predicted hyperglycemic and hypoglycemic conditions. In some exemplary implementations, audible signals may be differentiated by tone, volume, duty cycle, pattern, duration, and/or the like. In some exemplary implementations, the audible signal may be configured to be silenced (e.g., snoozed or turned off) by pressing one or more buttons 224 on the sensor electronics module and/or by signaling the sensor electronics module using a button or selection on a display device (e.g., key fob, cell phone, and/or the like).

Although audio and vibratory alarms are described with respect to FIG. 2, other alarming mechanisms may be used as well. For example, in some exemplary implementations, a tactile alarm is provided including a poking mechanism configured to "poke" the patient in response to one or more alarm conditions.

The battery 234 may be operatively connected to the processor module 214 (and possibly other components of the sensor electronics module 12) and provide the necessary power for the sensor electronics module 12. In some exemplary implementations, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some exemplary implementations, the battery is rechargeable. In some exemplary implementations, a plurality of batteries can be used to power the system. In yet other implementations, the receiver can be transcutaneously powered via an inductive coupling, for example.

A battery charger and/or regulator 236 may be configured to receive energy from an internal and/or external charger. In some exemplary implementations, a battery regulator (or balancer) 236 regulates the recharging process by bleeding off excess charge current to allow all cells or batteries in the sensor electronics module to be fully charged without overcharging other cells or batteries. In some exemplary implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a PC communication (com) port can be provided to enable communication with systems that are separate from, or integral with, the sensor electronics module. The communication port, for example, may comprise a serial (e.g., universal serial bus or "USB") communication port, allows for communicating with another computer system (e.g., PC, personal digital assistant or "PDA," server, or the like). In some exemplary implementations, the sensor electronics module 12 is able to transmit historical data to a PC or other computing device (e.g., an analyte processor as disclosed herein) for retrospective analysis by a patient and/or physician.

In some continuous analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics module 12 may be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Although separate data storage and program memories are shown in FIG. 2, a variety of configurations may be used as well. For example, one or more memories may be used to provide storage space to support data processing and storage requirements at sensor electronic module 12.

Figure 3A:
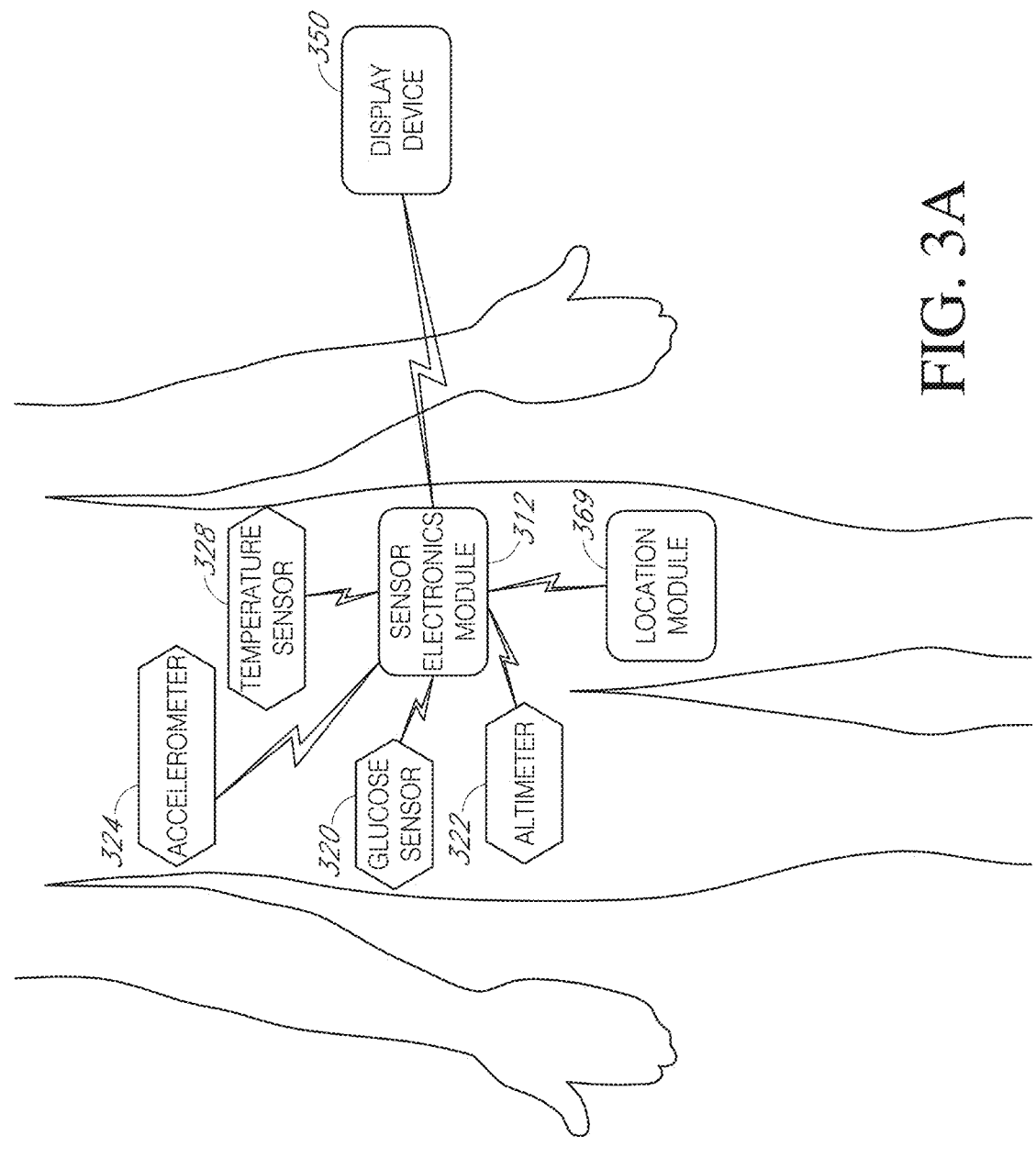
FIG. 3A depicts a block diagram illustrating the sensor electronics module communicating with multiple sensors, including a glucose sensor in accordance with some exemplary implementations.

FIG. 3A depicts an example a diagram illustrating sensor electronics module 312 in communication with multiple sensors, including a glucose sensor 320, an altimeter 322, an accelerometer 324, a temperature sensor 328, and a location module 369 (e.g., a global positioning system processor or other source of location information) in accordance with some exemplary implementations. Although FIG. 3A depicts sensor electronics module 312 in communication with specific sensors, other sensors and devices may be used as well including, for example, heart rate monitors, blood pressure monitors, pulse oximeters, caloric intake, medicament delivery devices, and the like. Moreover, one or more of these sensors may provide data to the analyte processing system 400 and/or analyte processor 490 described further below. In some implementations, a user may manually provide some of the data to analyte processing system 400 and/or analyte processor 490. For example, a user may provide calories consumed information via a user interface to analyte processing system 400 and/or analyte processor 490.

In the example depicted at FIG. 3A, each of the sensors 320-328 communicates sensor data wirelessly to the sensor electronics module 312. In some exemplary implementations, the sensor electronics module 312 includes one or more of the sensors 320-328. In some exemplary implementations, the sensors are combined in any other configuration, such as a combined glucose/temperature sensor that transmits sensor data to the sensor electronics module 312 using common communication circuitry. Depending on the embodiment, fewer or additional sensors may communicate with the sensor electronics module 312. In some exemplary implementations, one or more of the sensors 320-328 is directly coupled to the sensor electronics module 312, such as via one or more electrical communication wires.

The sensor electronics module 312 may generate and transmit a data package to a device, such as display device 350, which may be any electronic device that is configured to receive, store, retransmit, and/or display displayable sensor data. The sensor electronics module 312 may analyze the sensor data from the multiple sensors and determine which displayable sensor data is to be transmitted based on one or more of many characteristics of the host, the display device 350, a user of the display device 350, and/or characteristics of the sensor data. Thus, the customized displayable sensor information that is transmitted to the display device 350 may be displayed on the display device with minimal processing by the display device 350.

Figure 3B:
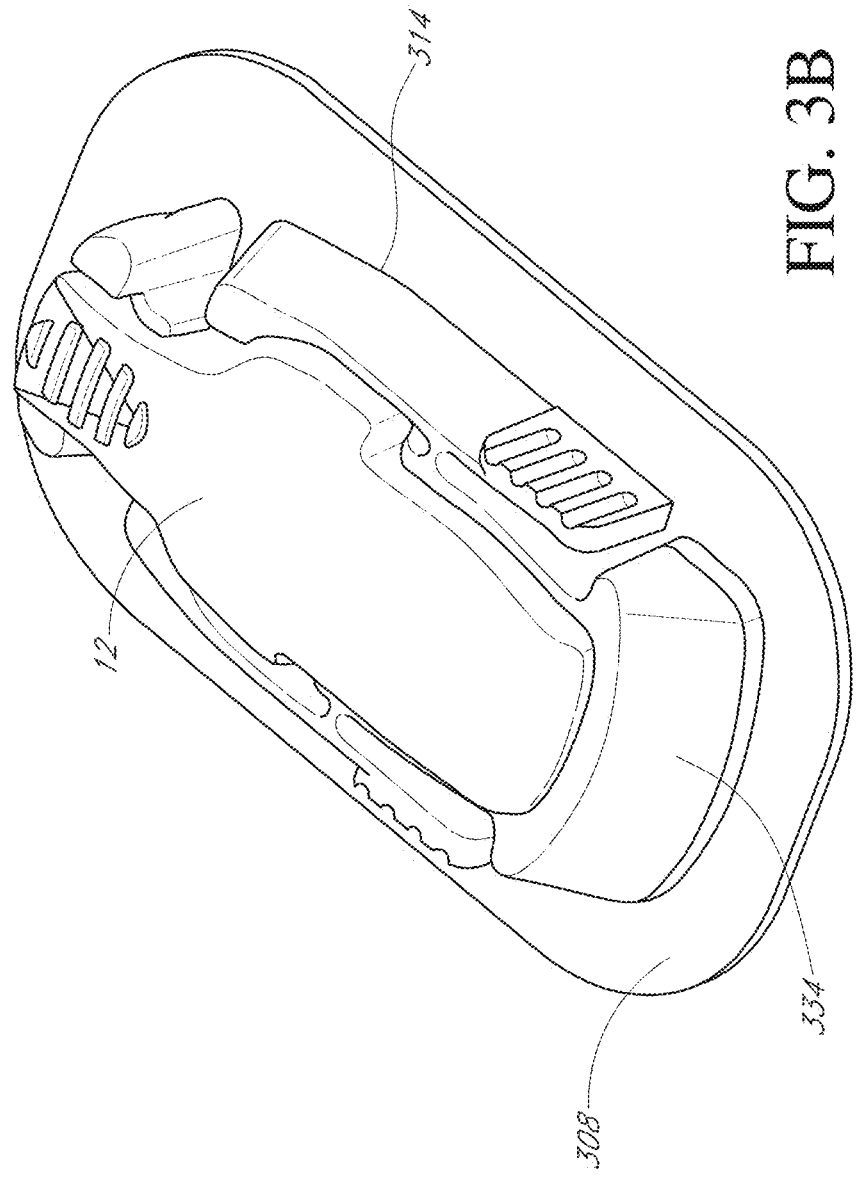
FIG. 3B depicts a perspective view of a sensor system including a mounting unit and sensor electronics module attached thereto in accordance with some exemplary implementations.
Figure 3C:
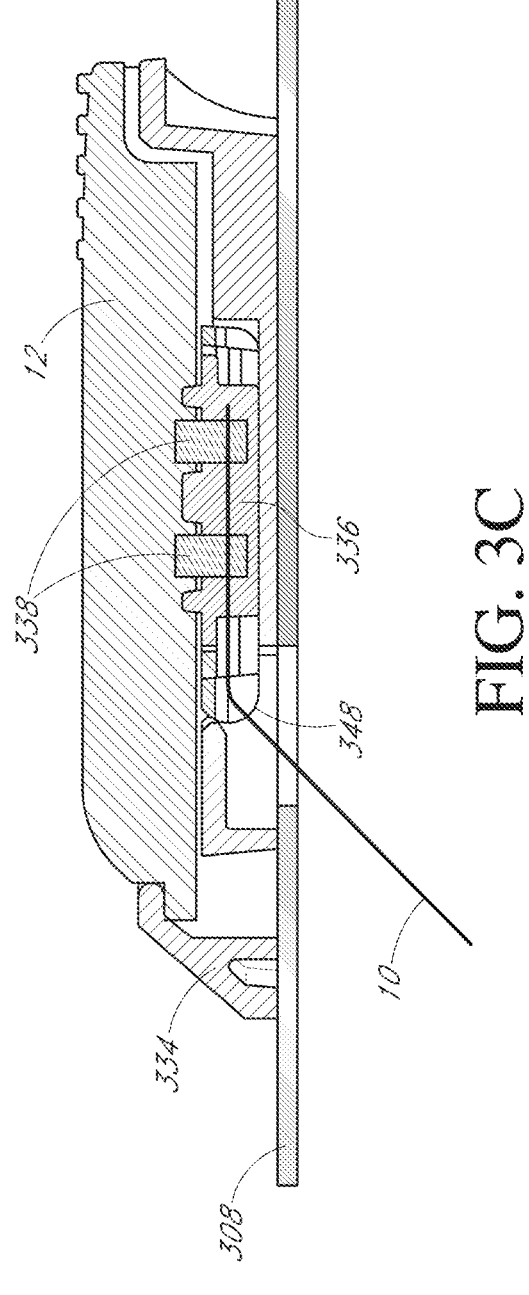
FIG. 3C depicts a side view of the sensor system of FIG. 3B.

FIGS. 3B and 3C are perspective and side views of a sensor system including a mounting unit 314 and sensor electronics module 12 attached thereto in an embodiment, shown in its functional position, including a mounting unit and a sensor electronics module matingly engaged therein. In some exemplary implementations, the mounting unit 314, also referred to as a housing or sensor pod, comprises a base 334 adapted for fastening to a host's skin. The base can be formed from a variety of hard or soft materials, and can comprise a low profile for minimizing protrusion of the device from the host during use. The base 334 may be formed at least partially from a flexible material, which is believed to provide, in some implementations, numerous advantages over other transcutaneous sensors, which, unfortunately, can suffer from motion-related artifacts associated with the host's movement when the host is using the device. The mounting unit 314 and/or sensor electronics module 12 may be located over the sensor insertion site to protect the site and/or provide a minimal footprint (utilization of surface area of the host's skin).

In some exemplary implementations, a detachable connection between the mounting unit 314 and sensor electronics module 12 is provided, which may enable improved manufacturability, namely, the relatively inexpensive mounting unit 314 can be disposed of when replacing the sensor system after its usable life, while the relatively more expensive sensor electronics module 12 can be reusable with multiple sensor systems. In some exemplary implementations, the sensor electronics module 12 is configured with signal processing, for example, configured to filter, calibrate and/or other algorithms useful for calibration and/or display of sensor information.

In some exemplary implementations, the contacts 338 are mounted on or in a subassembly (hereinafter referred to as a contact subassembly 336) configured to fit within the base 334 of the mounting unit 314 and a hinge 348 that allows the contact subassembly 336 to pivot between a first position (for insertion) and a second position (for use) relative to the mounting unit 314. The hinge may provide pivoting, articulating, and/or hinging mechanisms, such as an adhesive hinge, a sliding joint, and the like, and the action of the hinge may be implemented, in some implementations, without a fulcrum or a fixed point about which the articulation occurs. In some exemplary implementations, the contacts 338 are formed from a conductive elastomeric material, such as a carbon black elastomer, through which the sensor 10 extends, although the contacts may be formed in other ways as well.

In some exemplary implementations, the mounting unit 314 is provided with an adhesive pad 308, disposed on the mounting unit's back surface and including a releasable backing layer. Thus, removing the backing layer and pressing the base portion 334 of the mounting unit onto the host's skin adheres the mounting unit 314 to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site). Appropriate adhesive pads can be chosen and designed to stretch, elongate, conform to, and/or aerate the region (e.g., host's skin). The configurations and arrangements that provide water resistant, waterproof, and/or hermetically sealed properties may be provided with some of the mounting unit/sensor electronics module implementations described herein.

Figure 4A:
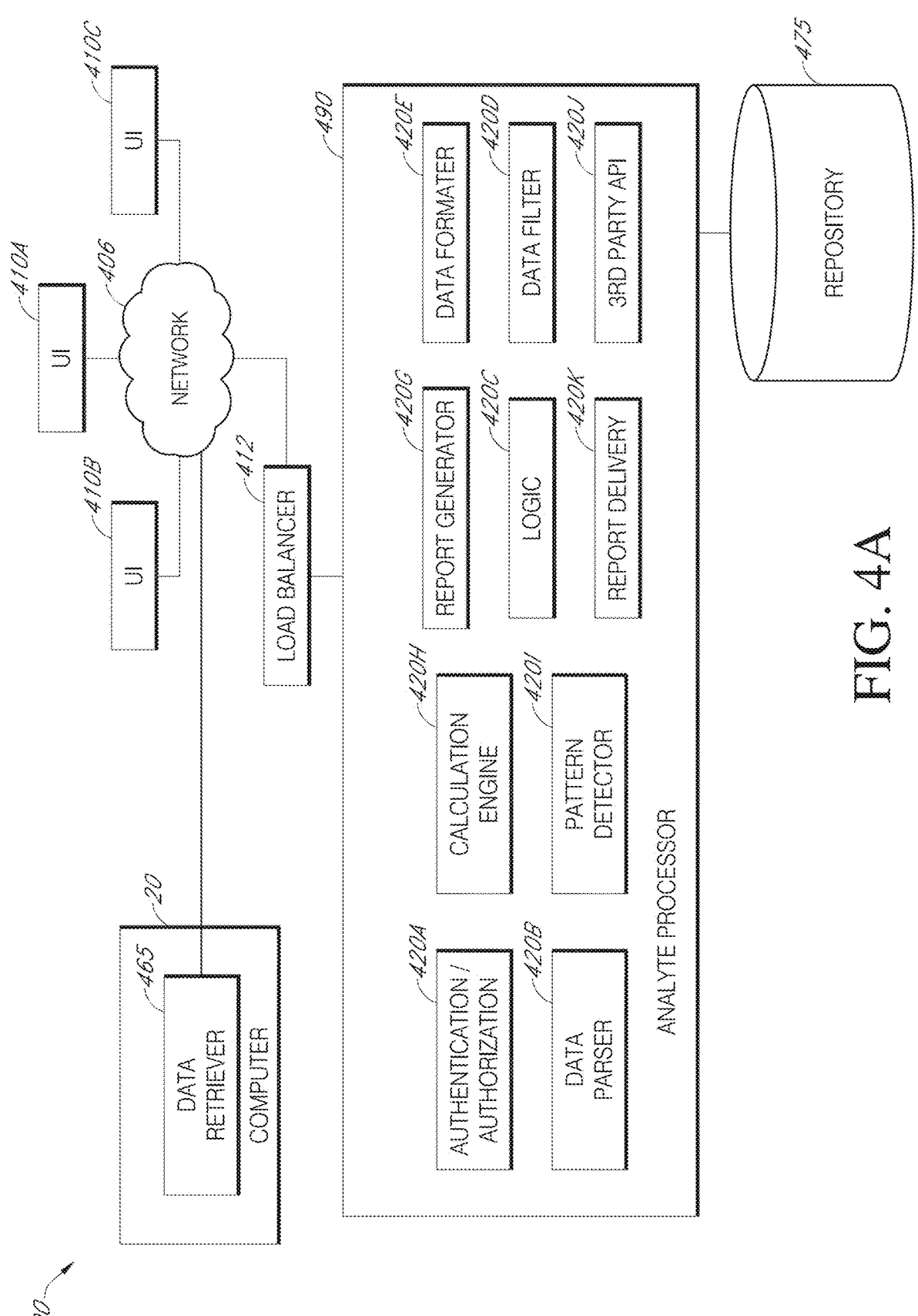
FIG. 4A depicts a block diagram of an analyte processing system in accordance with some exemplary implementations.

FIG. 4A depicts an example of an analyte data processing system 400, in accordance with some exemplary implementations. The description of FIG. 4A also refers to FIGS. 1 and 4B.

The analyte data processing system 400 may include one or more user interfaces 410A-C, such as a browser, an application, and/or any other type of user interface configured to allow accessing and/or interacting with analyte processor 490 via, for example, network 406 and a load balancer 412. The analyte processor 490 may further be coupled to a repository, such as repository 475.

Analyte data processing system 400 may also receive data from source systems, such as health care management systems, patient management systems, prescription management systems, electronic medical record systems, personal health record systems, and the like. This source system information may provide metadata for dynamic report generation.

Analyte data processing system 400 may be implemented in a variety of configurations including stand-alone, distributed, and/or cloud-based frameworks. However, the following description relates to an implementation of system 400 in a cloud-based framework, such as a software-as-a-service (SaaS) arrangement in which the analyte processor 490 is hosted on computing hardware, such as servers and data repositories maintained remotely from an entity's location (e.g., remote from a host, a health service provider, and like end-user) and accessed over network 406 by authorized users via a user interface, such as user interface 410A, B, and/or C, and/or a data retriever 465.

Figure 4B:
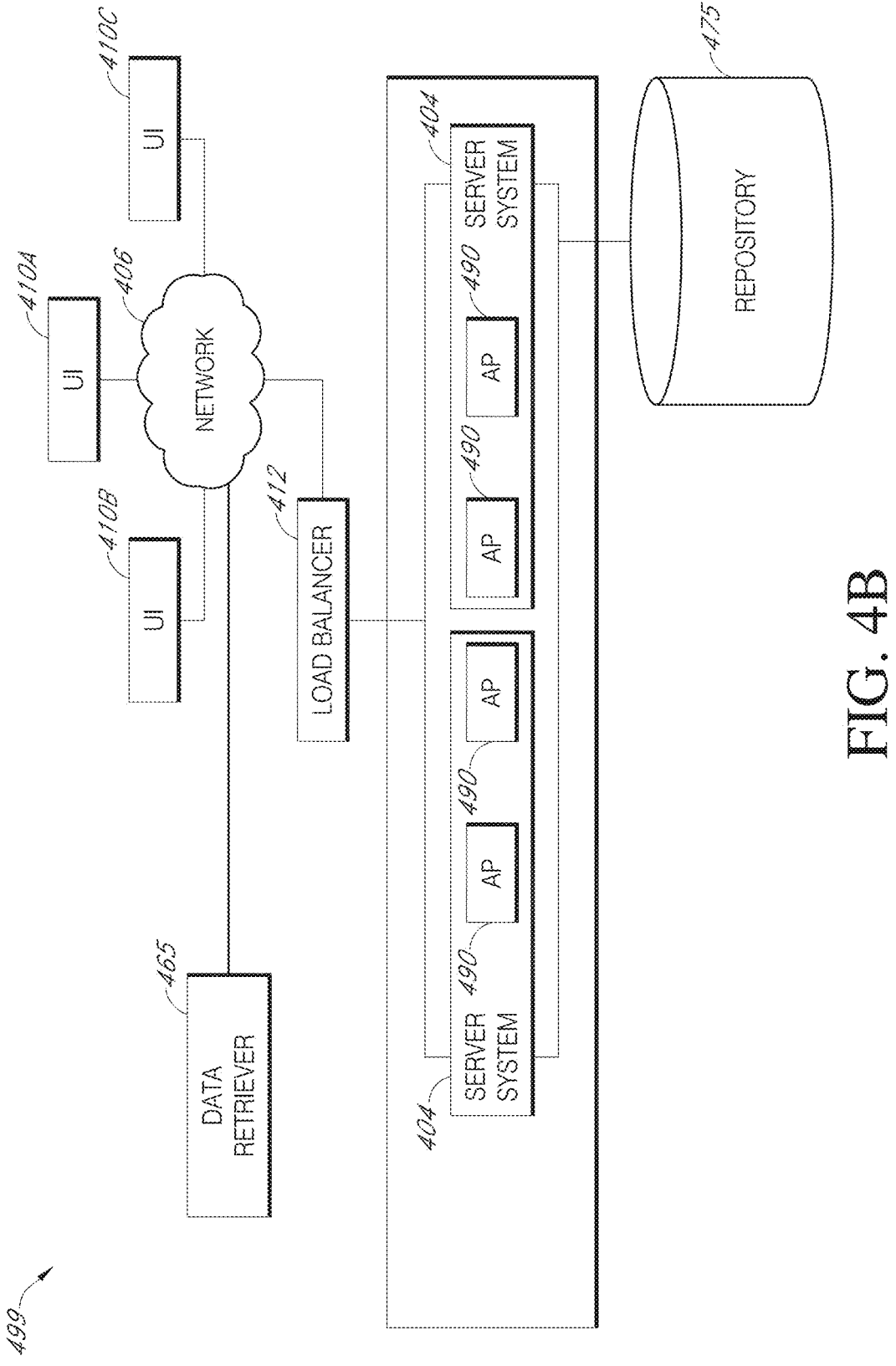
FIG. 4B depicts another block diagram of an analyte processing system in accordance with some exemplary implementations.

FIG. 4B depicts a system 499 which is similar to system 400, but system 499 is implemented as a SaaS-based system including a plurality of servers 404, each of which may be virtualized to provide one or more analyte processors 490. Moreover, each of the virtualized analyte processors 490 may serve a different tenant, such as an end-user, a clinic, a host wearing a sensor, and the like. To make more efficient use of computing resources of a software-as-a-service (SaaS) provider and to provide important performance redundancies and/or reliability, it may, in some implementations consistent with FIG. 4B, be advantageous to host multiple tenants (e.g., hosts, users, clinics, etc. at user interfaces 410A-C and/or data retriever 465) on a single system 400 and/or 499 that includes multiple servers and that maintains data for all of the multiple tenants in a secure manner at repository 475 while also providing customized solutions that are tailored to each tenant.

Referring again to FIG. 4A, in some exemplary implementations, analyte data processing system 400 may provide a cloud-based diabetes data management framework that receives patient-related data from various devices, such as a medical device, a glucose meter, a continuous glucose monitor, sensor system 8, display devices 14-20, source systems, and/or other devices (e.g., a device providing food consumption, such as carbohydrates, consumed by a host or patient, medicament delivery data, time of day, temperature sensors, exercise/activity sensors, and the like). In some exemplary implementations, the cloud-based diabetes data management receives the data programmatically with little (or no) intervention on the part of a user. The data received from devices, source systems, and the like may be in a variety of formats and may be structured or unstructured. For example, in some exemplary implementations, the system 400 receives raw sensor data, which has been minimally processed or analyzed, and the received data is then formatted, processed (e.g., analyzed), and/or stored in order to enable report generation. For example, a data retriever 465 may be implemented at one or more devices, such as computer 20 coupled to sensor system 8. In this example, data retriever 465 formats sensor data into one or more common formats compatible with analyte processor 490 and provides the formatted data to analyte processor 490, so that analyte processor 490 can analyze the formatted data. Although FIG. 4A depicts a single data retriever 465, in some exemplary implementations, a plurality of data retrievers 465 may be used to format data from a plurality of devices and/or systems, some of which have different data formats, into a single, common format compatible with analyte processor 490.

In some implementations, the data retriever 465 may be accessed through a kiosk including a processor, such as a dedicated computer, configured with a user interface, or may be accessed via a secure web-based interface residing on a non-dedicated computer.

In some implementations, the first time a processor (e.g., a computer, a smart phone, and any other device) accesses system 400, the data retriever may be programatically installed on the processor by downloading software for the data retriever to the processor's memory. The downloaded software is then programmatically installed on the processor, and then data retriever may generate a view (or page) which can be presented on a user interface to allow a user to fetch data (e.g., download data to system 400, analyte processor 490, and the like). In some implementations, this user interface may allow a user to select an icon, such as a fetch icon, to programmatically start a data transfer to analyte processor 490. For example, a user selects the fetch icon at the user interface on a processor, such as computer 20, which initiates a data transfer from a sensor system 8 coupled to data retriever 465 and analyte processor 490. In some implementations, the fetch icon may be implemented as a software widget. Moreover, the software widget may be placed on a webpage, so that when selected a fetch process begins for a registered user.

Moreover, the software associated with the data retriever may include a self-updating mechanism, so that when a fetch is selected at the user interface, the data retriever programmatically checks for an update (e.g., software, drivers, data, and the like) at analyte processor 490 (or another designated computer) and installs the update. The update may be performed programmatically with little (or no) intervention by a user. Data downloads from a device or system to the data retriever may be performed using a wired connection, such as a device-specific download cable, or wirelessly, when the device and the processor are equipped for wireless data transfer.

The analyte processor 490 may check data downloaded by the data retriever 465 for transmission-related errors, data formatting, device-related error codes, validity of the data, duplicate data points, and/or other aspects of the data. Moreover, if out-of-range data points or device errors are found, analyte processor may identify those data points by, for example, flagging those data points, subsequently correcting the identified data points programmatically or by a system administrator, and storing the corrected data points. Moreover, the analyte processor may be configured by a user, such as a clinician, doctor, and the like, to perform additional data processing steps, such as correcting time of day, correcting the date, and analyzing data by specific cohorts, groups, and relationships (e.g., demographics, such as age, city, state, gender, ethnicity, Type I diabetes, Type II diabetes, age of diabetes diagnosis, lab results, prescription drugs being used, self-reported conditions of the patient, diagnosed conditions of the patient, responses to questions posed to patient, and any other metadata representative of the host/patient). Once analyte processor performs initial data processing (e.g., checks, cleaning, and analysis), the processed data and/or the raw data provided by the data retriever may be stored at repository 475.

The processing at analyte processor 490 may also include associating metadata with the data received from the devices and/or sensors. Examples of metadata include patient information, keys used to encrypt the data, patient accelerometer, location data (e.g., location of patient or location of patient's clinic), time of day, date, type of device used to generate associated sensor data and the like. The patient information can include the patient's age, weight, sex, home address and/or any past health-related information, such as whether the patient has been diagnosed as a type 1 or type 2 diabetic, high-blood pressure, or as having any other health condition. The processing may also include analysis, such as determining one or more descriptive measurements and/or generating reports based on received information and descriptive measurements. These descriptive measurements may include statistics (e.g., median, inner and outer quartile ranges, mean, sum, n, standard deviation, and coefficients of variation). Examples of reports are depicted at FIGS. 6A-1, 6A-3 through 6A-28, and 7-10.

In the example of FIG. 4A, user interfaces 410A-C may be used by one or more entities, such as end-users, hosts, health care providers, clinics, patients, research groups, health systems, medical device manufacturers and the like. These entities may remotely access analyte processing system 400 via user interface 410A-C to request an action, such as retrieve analyte data, provide analyte data, request analysis of analyte data, request generation of reports including modules having views presenting descriptive measurements of the analyte data, present analyte data and reports, and the like. For example, user interface 410A may send a request (e.g., a message and the like) to initiate an action at an analyte processor 490, which is remote (e.g., separate from the user interfaces and coupled by a network). The action may request a report for the sensor data provided by data retriever 465 (e.g., a single processor, such as computer 20, may host data retriever 465 and user interface 410A). Other examples of actions include providing sensor data, such as glucose data, carbohydrate data, insulin pump data, and the like, to the analyte processor 490, initiating processing of the sensor data, initiating analysis of the sensor data, and storing data at repository 475. In some exemplary implementations, the computing resources provided by analyte processor 490 may comprise one or more physical servers virtualized to provide the analyte processing services disclosed herein.

The data retriever 465 may obtain (e.g., receive, retrieve, and the like) data from one or more sources and provide any obtained data in a format compatible for use within analyte processor 490. In some implementations, data retriever 465 may be implemented in one or more of the source systems and/or devices providing data to analyte processor 490. For example, data retriever 465 may be implemented in one or more devices, such as sensor system 8, sensor 10, display devices 14, 16, 18, and/or 20, medicament pump 2, glucose meter 4, computers/processors coupled to those devices, and any other device capable of providing data to system 400. In these implementations, data retriever 465 receives data from a host device and formats the sensor data in a format compatible with analyte processor 490. The data retriever 465 may also be implemented on source systems, such as disease management systems, weight management systems, prescription management systems, electronic medical records systems, personal health record systems, and the like. In these implementations, data retriever 465 obtains data from the source system and formats the data in a format compatible with analyte processor 490.

In some exemplary implementations, data retriever 465 may, as noted, be downloaded and/or provided automatically to a device, a computer, a system, and the like. For example, when a user on a computer first accesses system 400, system 400 may automatically install and configure the data retriever 465 on the user's computer. Once the install is complete, the data retriever 465 may begin fetching data for system 400 and format, if needed, the data to allow processing of the fetched data by analyte processor 490. To further illustrate by way of an example, the data retriever 465 may be downloaded onto a device, such as computer 20. In this example, when computer 20 receives sensor data from sensor electronics module 12, a data retriever 465 may provide sensor data and/or metadata in a format compatible with analyte processor 490.

In some exemplary implementations, the analyte processor 490 may process the received data by performing one or more of the following: associating metadata with the data received from the devices, sensors, source system, and/or data retriever; determining one or more descriptive measurements, such as statistics (e.g., median, inner and outer quartile ranges, mean, sum, n, and standard deviation); generating reports including modules having views presenting descriptive measurements of the analyte data; validating and verifying the integrity of the received data from the devices, sensors, source system, and/or data retriever; processing received data based on metadata (e.g., to select certain patients, devices, conditions, diabetic type, and the like), and/or correlating received data from the devices, sensors, source system, and/or data retriever, so that the data can be compared and combined for processing including analysis.

Moreover, the results of any processing performed by analyte processor 490 may be used to generate one or more reports including selected modules having views presenting descriptive measurements presented as graphs, bar graphs, static charts, charts, and the like. Furthermore, the reports and other outputs generated by system 400 may be provided via one or more delivery mechanisms, such as report delivery module 420K (e.g., as email, secure email, print, text, presentations for display at a user interface, such as at user interface 410A-C hosted at a tablet or other processor), machine-to-machine communications (e.g., via third party interface 420J), and any other communication mechanism.

In some exemplary implementations, the reports may be customized dynamically for use by an entity, such as a host, an end-user, a clinician, a healthcare provider, device manufacturer and the like. Furthermore, the reports may be customized based on the types and/or quantity of sensors and systems providing data to system 400 and the types of metadata available to system 400. This customization may be performed by a user, by system 400 programmatically, or a combination of both.

In some exemplary implementations, one or more of the user interfaces 410A-C may be implemented on a processor, such as computer 20 or other processor, serving a kiosk at a health care provider, clinic, and the like. For example, a user, such as a host (also referred to as a patient), may enter a health care facility and access the kiosk in order to couple and to provide sensor data and/or metadata to system 400. In this example, the user may provide sensor data and/or metadata to system 400 and then view at one or more of user interfaces 410A-C one or more reports including information representative of the sensor data and/or metadata provided to system 400 including statistical measures of the data. Although the previous example using the kiosk, the kiosk may also be used by a health care provider or administrative staff as well.

Although the previous example refers to computer 20 including a user interface and a data retriever to provide a kiosk, the user interface may be located in other devices, such as smart phones, tablet computers, display devices, and other like processors. Moreover, the computer 20 may be located at locations other than a kiosk. For example, computer 20 may be located at a host's home and include a data retriever 465 to retrieve data from a sensor associated with the host, so that the data retriever 465 can format and provide the sensor data to analyte processor 490. The user interface and data retriever may also be configured at a workstation of a health care provider or clinician.

Analyte processor 490 may include, in some exemplary implementations, an authenticator/authorizer 420A for authorizing access to analyte processor 490, a data parser 420B for parsing requests sent to analyte processor 490, a calculation engine 420H for receiving data from sensors and processing the received data into counts for use with histograms, logic 420C, a data filter 420D, a data formatter 420E, a report generator 420G, a pattern detector 420I, a report delivery module 420K for delivering reports in a format for the destination, and a third party access application programming interface to allow other systems and device to access and interact with analyte processor 490.

Analyte processor 490 may receive a request from a user interface, such as user interface 410A-C, to perform an action (e.g., provide data, store data, analyze/process data, request a report, and the like). Before analyte processor 490 services the request, the analyte processor 490 may process the request to determine whether the request is authorized and authenticated. For example, authenticator and authorizer 420A may determine whether the sender of the request is authorized by requiring a user to provide a security credential (e.g., a user identifier, a password, a stored security token, and/or a verification identifier provided by text message, phone, or email) at a user interface presented on a computer. If authorized, authenticator and authorizer 420A may authenticate the sender of the request to check whether a security credential associated with sender of the request indicates that the sender (e.g., a user at user interface 410A) is indeed permitted to access a specific resource at system 400 in order to perform the action, such as store (or upload) data at repository 475, perform analyze/process data, request report generation, and the like.

To further illustrate, the data retriever 465 associated with a sensor system 8 and a computer 20 may be authorized and authenticated by authenticator and authorizer 420A to access analyte processor 490 in order to write data to a buffer or other storage mechanism, such as repository 475. On the other hand, an entity, such as a user, at user interface 410A may be authorized and then authenticated by authenticator and authorizer 420A to access analyte processor 490, but only permitted to access certain information. In this second example, the user at user interface 410A may be authorized and authenticated to access repository 475 to view certain information corresponding to the user's own glucose data and access reports generated for the glucose data, but the user will not be authorized and authenticated to access another user's data and/or reports. Another example may be the case when a user associated with a clinic, a hospital, and/or a research group requests access to all data associated with their patients. In this example, the user may be granted access to their patients but not other patients. Yet another example may be the case when a user associated with a clinic, a hospital, and/or a research group requests access to all data associated with patients using a certain device, such as a specific type analyte sensor. In this example, the user may be granted access to data specific to the type of analyte sensor but not other sensors (and PII may be removed or made anonymous).

Once authorized and/or authenticated, the request received at analyte processor 490 may then be parsed by data parser 420B to separate any data, such as sensor data, metadata, and the like, from the request. In some implementations, data parser 420B may perform check data formatting, device-related error codes, validity of the data, duplicate data points, and/or other aspects of the data. Moreover, the data parser 420B may associate additional metadata with the separated data. The metadata may include any of the metadata described herein, including an owner of the data, a key to track the data, an encryption key unique to each user, time of day, date information, one or more locations where the data is (or will be stored), and the like. In some exemplary implementations, the data parsing 420 may provide data to the calculation engine 420H for formatting the data into counts and histograms as described further below.

In some exemplary implementations, the request (or the parsed data therein) may be processed by calculation engine 420H. The calculation engine 420H preprocesses the data received from devices, sensors, and the like to form "counts." The counts represent a measured value, such as an analyte value measured by a sensor, a glucose value measured by a sensor, a continuous glucose value measured by a sensor, and/or other diabetes related information, such as carbohydrates consumed, temperature, physical activity level, and the like, and how often that measured value occurred.

Figure 5:
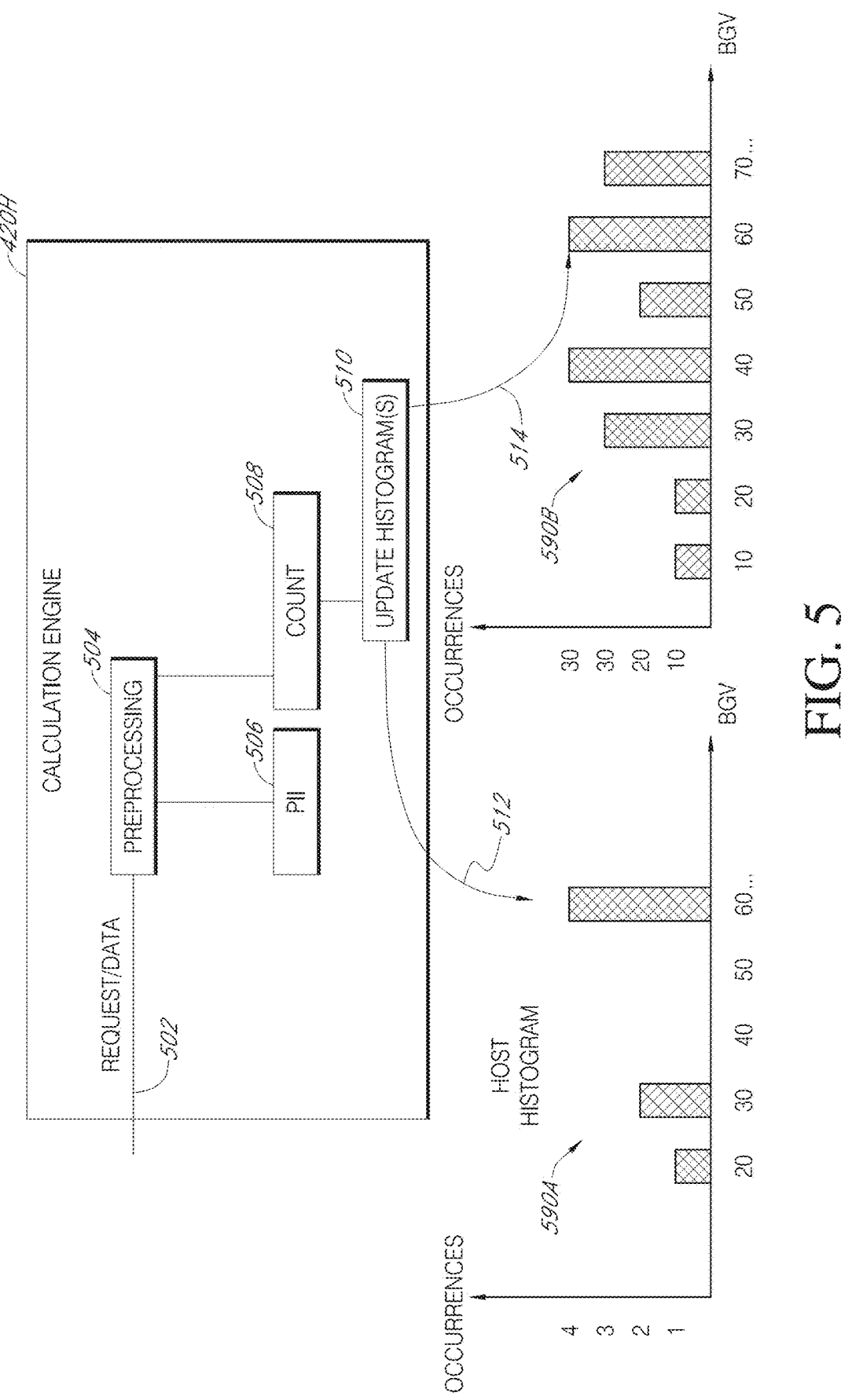
FIG. 5 depicts a block diagram of a calculation engine configured to generate counts representative of analyte levels in a host in accordance with some exemplary implementations.

FIG. 5 depicts an example implementation of the calculation engine 420H. When a request 502 is received at the calculation engine 420H, the calculation engine 420H may preprocess 504 the request to extract data, such as sensor data, and thus form a count. The count may represent a numerical value representative of sensor data provided by, for example, data retriever 465, computer 20, sensor system 8, and/or any other source of data and how often it occurred. For example, the count may represent a glucose value measured by a continuous glucose sensor, such as continuous analyte sensor 10, and how often it occurred over a certain period of time.

The calculation engine 420H may also preprocess 504 the request 502 to provide and/or determine other metadata, such as to determine personal identifiable information (PII) 506 associated with the request 502, time of day/date, and the like, although in some implementations the calculation engine may receive the request without PII information. The PII may include a serial number of the sensor system 8 and any other information that may identify the host associated with sensor system 8. In some exemplary implementations, the PII may be stored in repository 475 in an encrypted form to enhance the privacy of the PII. Furthermore, the PII may be encrypted with an encryption technique and/or key that is different from other information stored at repository 475. For example, analyte processor 490 may store at repository 475 data from a plurality of users, such as hosts, patients, and the like. To maintain privacy, each user's data may be encrypted with a separate key. Moreover, PII information may be encrypted with yet another key to further enhance the privacy of the user.

The calculation engine 420H may then use the count 508 to perform additional processing. The additional processing may include storing the count in repository 475, which may include one or more databases to store the counts. Moreover, the count may be stored with metadata, such as time of day/date information, the original request 502, and the like. Furthermore, the count may be encrypted, as noted, before storage in repository 475, and, in some exemplary implementations, the count and/or metadata may be encrypted with an encryption technique and/or key that is different from the PII.

Although some of the examples described herein refer to databases, the databases may also be implemented as any type of data store, such as relational databases, non-relational databases, file systems, and the like.

The calculation engine 420H may also use the count to update one or more histograms 510. For example, rather than keep track of and process a host's glucose levels over a certain period of time using raw sensor data values, the calculation engine 420H may convert the data values into counts. The counts may be added to a histogram 590A for a given host. In the example of FIG. 5, the histogram 590A includes an x-axis of glucose concentration values and a y-axis of the number of occurrences for each glucose concentration value. In this example, if the count 508 for a host is 60, the calculation engine 420H updates 512 the bin associated with the value 60. The histogram 590A may be associated with a given patient/host to represent the glucose levels of the host. Because the possible glucose concentration levels typically fall into a certain range, the values of the bins can be predetermined in some exemplary implementations.

In some exemplary implementations, the histogram 590A may also be associated with a given time during the day (also referred to as an epoch). For example, histogram 590A may represent a time, such as 1 PM to 1:30 PM, and, in this example, calculation engine 420H may generate other histograms for other times.

In some exemplary implementations, the calculation engine 420H may generate a plurality of histograms for a given host for given time periods. For example, 48 histograms corresponding to 30-minute epochs over a 24 hour period may be generated, so that each time a count is received, the count is added to one of the 48 histograms based on a time associated with the count and a corresponding histogram. In this example, a count representative of a blood glucose measurement made at 12:30 AM would update a histogram designated to cover measurements made during that epoch, while another count with a time of day at 1:30 AM would update another histogram assigned to represent the 1:30 AM epoch. Moreover, these 48 histograms may be stored in a database in a data structure to facilitate access. For example, each of the 48 histograms may be stored as rows in a database. Moreover, calculation engine may determine, based on the one or more histograms, statistics using set theory as described further below.

Although the previous example utilizes a 30-minute interval as an epoch, other intervals of time, such as 15 minutes, and the like, may be used as well.

In some exemplary implementations, the calculation engine 420H may also update other histograms representative of aggregate count information. For example, the count 508 may be used to update histograms 510 representative of so-called "cohorts" of the host used to generate histogram 590A. The term "cohorts" refers to hosts that can be grouped, and this grouping may be based on one or more factors, such as a demographic, a health condition, an age, a geographic location (e.g., country, state or zip code), and the like. In the example of FIG. 5, the histogram 590B is updated 514 with the same count value as histogram 590A, but the histogram 590B represents cohorts associated with, for example, all of the other patients in a clinic where the host is being treated. As such, histogram 590B may provide insight into the host and the host's cohorts at the clinic.

Moreover, the calculation engine 420H may also update other histograms used to pre-calculate statistics associated with the host or cohorts. For example, the calculation engine may update histograms (which are associated with a certain patient) and update other histograms (which may be for other patients, such as cohorts selected based on metadata, such as a zip code, an age, a gender, and the like). In addition, the calculation engine 420H may also form other histograms based on statistics, such as a union, an intersection, a set difference, and the like. For example, calculation engine 420H may use set theory to determine the union of histograms. The union represents the set of all objects that are in a first histogram A, a second histogram B, or a combination of both (denoted A∩B). The calculation engine 420H may also determine intersections (e.g., the set of all objects that are only in first histogram A and the second histogram B, denoted A U B), and may determine the set difference (e.g., the set of all members of the first histogram A that are not in second histogram B, denoted A\B).

In some implementations, the calculation engine uses the histograms and set theory operations to determine aggregate statistical information and to form a so-called aggregate histogram. For example, a report may be generated to include an aggregate histogram for all patients in a geographic region, such as the United States. In this example, the calculation engine may identify existing histogram groups that provide the smallest number of histograms to cover the geographic region of interest. Specifically, the histograms of all patients (or clients) that are in the United States may be merged using set theory to form a virtual histogram of the United States for a given time frame, such as the past 30 days. In addition, this operation may, in some implementations, be performed very rapidly, when compared to performing such operations on raw sensor data. In some implementations, the repository may store a plurality of histograms (e.g., histograms may be organized based on patient, clinic, zip code, etc.) which can be readily processed using set theory to form the aggregate histogram or determine statistics for the aggregate histogram. Moreover, in some implementations, an aggregate histogram may be configured for storage at the repository, in which case the calculation would update the aggregate histogram with counts rather than generate it using set theory. Although the previous example refers to the aggregate histogram generated based on geographic location, the aggregate histogram may be generated on other metadata described herein as well (e.g., demographics, age, zip code, type of diabetes, age of diagnosis, and the like).

In some implementations, the calculation engine 420H may have to update, as noted, a plurality of histograms. When this is the case, the calculation engine 420H may update the histograms in a distributed manner based on eventual consistency.

Although the description with respect to the calculation engine 420H refers to a histogram, the histogram, as used herein, refers to a data structure that includes one or more values (e.g., values) associated with one or more time intervals. For example, the histogram may represent one or more values, such as frequency of occurrence, associated with bins corresponding to one or more time intervals. Moreover, this data structure may be stored at a database, so that it is readily accessed with a read, such as in a row of a database (or, for example, in a column if a column database is used).

In some exemplary implementations, repository 475 stores the histograms including counts in a database. For example, repository 475 may store data for a patient that covers a time frame, such as 1 day, 2 days 7 days, 30 days, or more. In this example, the days may be subdivided into epochs, each of which has a corresponding histogram stored in repository 475. Moreover, each histogram may be stored as a row (or column) in a database at repository 475 to facilitate fast data access.

Referring again to FIG. 4A, logic 420C may also process requests to perform an action (e.g., store, retrieve, process, analyze, report data, and the like) at analyte processor 490. For example, logic 420C may control the actions of the analyte processor 490 when processing a request to store data at repository 475. In this example, the request may, under control of logic 420C, be parsed at data parser 420B, converted into a count at calculation engine 420H, added to histogram 590A-590B, and then forwarded to repository 475 for storage. Moreover, this process may occur serially and/or asynchronously (e.g., the data parser may extract data and provide data for asynchronous updating of counters associated with histograms, and the subsequent data store at the repository may occur asynchronously or substantially simultaneously).

Logic 420C may also determine one or more descriptive measurements, such as statistics (e.g., a median, inner and outer quartile ranges, a mean, a sum, a standard deviation, and the like) based on counts, histograms, and/or received sensor data. The logic 420C may provide these descriptive measurements to the report generator 420G to enable report generation (e.g., for presentation at a user interfaces 410A-C). For example, the mean may be determined by summing the product of the count and the bin value and then dividing that sum by the sum of the counts. Referring again to FIG. 5 at histogram 590A, the mean is 46 (20*1+30*2+60*4)/(1+2+6).

The pattern detector 420I may perform pattern detection on data, such as sensor data representative of blood glucose data, analytes, and other data as well (e.g., insulin pump data, carbohydrate consumption data, and the like) processed by analyte processor 490 and stored at repository 475. Moreover, the pattern detector 420I may detect patterns retrospectively for a predetermined time period defined by system 400 and/or a user.

In some exemplary implementations, the pattern detector 420I may receive input data from the repository 475, and the input data may include sensor data representative of glucose concentration data, analytes, and other data as well (e.g., insulin pump data, carbohydrate consumption data, histograms and/or counts, data from a continuous glucose monitor (CGM data), time of day, amount of carbohydrates, other food related information, exercise, awake/sleep timer intervals, medications ingested, and the like). Moreover, the input data may comprise historical data obtained over a time frame, such as 8 hours, 1 day, 2 days, 7 days, 30 days, and/or any other time period. For example, the input data may comprise counts representative of monitored analyte detection levels (e.g., glucose concentration levels) received and stored at system 400 over a period covering a four-week time frame.

The pattern detector 420I may analyze the input data for patterns. For example, patterns can be recognized based on one or more predefined rules (also referred to as criteria or triggers). Furthermore, the one or more predefined rules may be variable and adjustable based user input. For example, some types of patterns and rules defining patterns can be selected, turned off and on, and/or modified by a user, a user's physician, or a user's guardian, although system 400 may select, adjust, and/or otherwise modify rules programmatically as well.

Some examples of the types of relationships in the input data that can be considered a pattern are one or more of the following: a glucose level that exceeds a target glucose range (which may be defined by a user, a health care provider, system 400, or a combination thereof); a glucose level that is below a target glucose range; a rapid change in glucose level from a low to a high (or vice versa); times of day when a low, a high, an at range, or rapid glucose level event occurs; and/or days when a low, a high, an at range, or a rapid glucose level event occurs.

Additional examples of the types of relationships in the input data that can be considered a pattern include hypoglycemic events by time of day. As an example, a pattern may be identified in situations where the user has low glucose concentrations around the same time in the day. Another type of pattern, which may be identified, is a "rebound high" situation. For example, a rebound high may be defined as a situation where a user overcorrects a hypoglycemic event by overly increasing glucose intake, thereby going into a hyperglycemic event. These events may be detected based on one or more predefined rules. Patterns that may be detected include a hyperglycemic pattern, a hypoglycemic pattern, patterns associated with a time of day or week, a weighted scoring for different patterns based on frequency, a sequence, and a severity. Patterns may also be based on a custom sensitivity of a user, a transition from a hypoglycemic to hyperglycemic pattern, an amount of time spent in a severe event, and a combination of glucose change and time information. Detected patterns may also be patterns of high variability of glucose data. Further, a pattern may be based on a combination of previous pattern data and a currently detected situation, whereby the combined information generates a predictive alert.

The pattern detector 420I may detect the pattern and generate an output, which may be provided to report generator 420G for reporting. Moreover, the report may include a retrospective analysis of the input data and any patterns determined by pattern detector 420I. Although the previous example describes an approach for detecting patterns in data, other approaches may be used as well.

The data filter 420D may be used to check whether an output generated by analyte processor 490, such as a response for certain types of data, a report, and the like, does not violate a data rule. For example, the data filter 420D may include a data rule to check whether a response includes data, such as Pll, to a destination which is not authorized or allowed to receive the response (e.g., based upon authorization and authentication and the corresponding role of the user making the request).

The data formatter 420E may format data for delivery based on the type of destination. For example, the data formatter 420E may format a report based on whether it is being sent to a printer, a user interface, a secure email, another processor, and the like.

The report generator 420G may generate one or more reports. The reports may provide descriptive information, such as statistical information, representative of the sensor data received at analyte processor 490. Moreover, the report may provide a retrospective analysis of the sensor data stored at repository 475. For example, the report may provide statistical information based on sensor data (and/or corresponding histograms including counts) over a time frame, such as 8 hours, 1 day, 2 days, 7 days, 30 days, and any other time frame. Moreover, the report may allow a user, such as a patient, a host, or a clinician, to view the report and identify trends and other health related issues.

In some exemplary implementations, report generator 420G generates reports based on data received and/or stored at system 400 (e.g., using sensor data, metadata, counts, histograms, and the like). Examples of reports and/or the modules that may be used in a report are depicted at FIGS. 6A-1, 6A-3 through 6A-28, and FIGS. 7-11.

Moreover, the report generator 420G may configure reports based on the metadata representative of the types of sensors providing sensor data to system 400, the quantity of sensors providing sensor data to system 400, a user preference, such as a selection by a host and/or a clinician, a size of the display of a user interface, a state of the host, and/or the length of the report.

In some exemplary implementations, the report represents retrospective data (also referred to as historical data) received and stored at system 400 over a certain time frame, such as 8 hours, 1 day, 2 days, 7, days, 30 days, since the last upload of data to system 400, since the last visit to doctor/clinic, and any other time frame. For example, a user and/or a clinician may access user interface 410A and select a time frame over which the data should be retrieved from repository 475 for analysis (e.g., retrieve glucose data, carbohydrate consumption data, and insulin pump data measured for a host in the past 30-days and/or histograms including counts representative of such measured data). Although the previous example describes user selection of the time frame, the time frame may be programmatically selected by system 400 as well. In any case, the report generator 420G may compile a report using one or more modules described further below.

Figures 1, 6A:
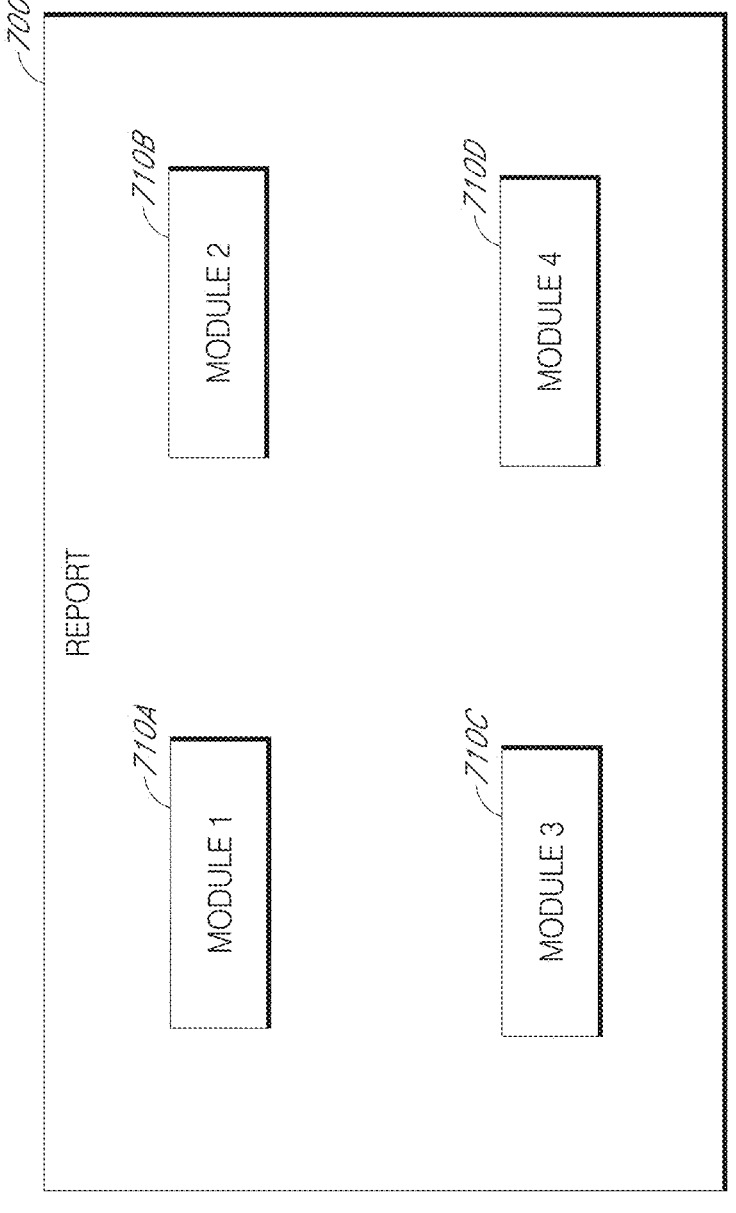
Figures 2, 6A:
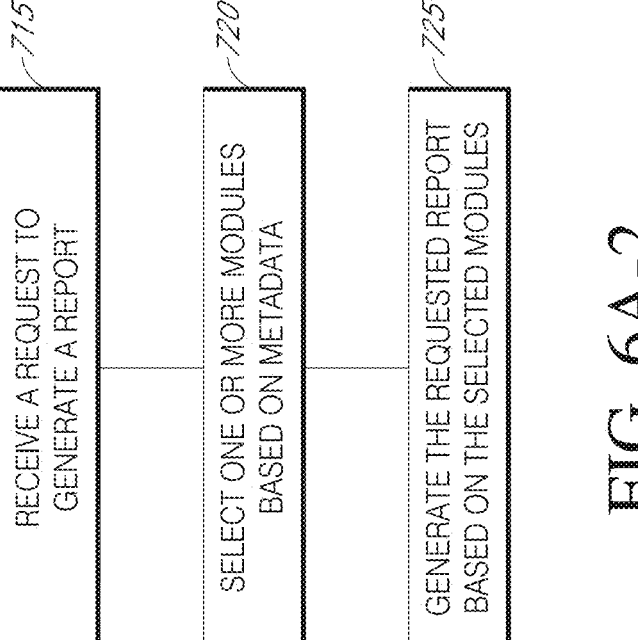

FIG. 6A-1 depicts an example of a report 700, which may be generated by report generator 420G. The description of FIG. 6A-1 also refers to FIG. 4a.

The report 700 may include one or more modules, 710A-D. The modules 710A-D may be self-contained, in the sense that they can be used independently of each other. For example, the report 700 can include one or more modules 710A-D, and the modules 710A-D may be placed in a variety of positions within the report. Moreover, the modules 710A-D in the report 700 may be dynamic in the sense the specific types of modules selected for a report may vary based on metadata. The metadata may include one or more factors, such as types of data available during the reported timeframe (e.g., sensor data and metadata), amount of data available during a timeframe, devices being used (e.g., insulin pump, glucagon pump, single-point glucose meter, continuous glucose meter and the like), user preferences (e.g., preference of a patient, a doctor, a clinician, and the like), size of the user interface available to present report 700, patient demographics, pre-selected/configured preferences provided by a user and/or system 400, other modules being used in the report (e.g., a certain module may not be allowed to be used with another module, while it may be required to use another module with the certain module), a quantity of information to be displayed (e.g., a continuous glucose monitor generating relatively more data than a self-monitoring blood glucose device may require certain modules), and/or any other factor.

In some exemplary implementations, a request may be received at, for example, report generator 420G. When the request is received, the report generator 420G may generate report 700 based on metadata as noted above. For example, metadata may be accessed by the report generator 402G to obtain information related to one or more factors. For example, the metadata may include patient information including report preferences, types and quantity of devices used, and display size being used to present the report, and other data related to the user, devices, and the like as noted above. The metadata may also include rules, such as whether a module can be used with certain devices (for example, certain reports may only be suitable for continuous blood glucose, rather than discrete measurements), whether a module can be used with certain patient conditions (for example, a caregiver may establish a rule requiring a certain report based on a patient's demographic, history, a general condition, and/or a condition or state at any instant of time), whether a module may be used on certain display sizes, whether a module may be used given a certain volume of data or device type, and/or any other rules defining which modules can be used in a given report.

In some example embodiments, report generator 420G may access metadata including templates. For example, a template may define the placement of one or more modules in a report.

The framework defining the placement of each module 710A-D may be a template (also referred to as a model). Moreover, templates may be defined for certain devices or displays, so that when the request is made and/or metadata obtained, the report generator 420G can dynamically select, based on metadata, one or more modules into the predefined template. For example, a certain display device may be of a size which allows four modules to be displayed as depicted at FIG. 6A-1, while another display device may be of a size which allows two modules, and so forth. Although FIG. 6A-1 depicts an example implementation including four modules, other quantities (as well as placement of those modules) may be used as well.

In some exemplary implementations, the metadata may include a plurality of predefined templates configured for a specific patient, a specific caregiver, a specific medical professional, a group of patients (e.g., cohorts), a business-person, and/or the like. As such, modules may be dynamically selected based on an evaluation of the metadata. Moreover, the use of the templates may, in some implementations, allow the dynamic generation of modules to be performed more rapidly, when compared to not using the templates. In any case, when the report generator 420G selects which modules 710A-D are to be included in report 700, the report generator 420G may then obtain the underlying data (for example, sensor data, demographics, and the like) to be used in the selected modules.

FIG. 6A-2 depicts an example process for generating dynamic reports in accordance with some exemplary implementations. The description of FIG. 6A-2 also refers to FIG. 4A.

At 715, a request may be received to generate a report. For example, the report generator 420G may receive from a processor 20, a device 18, 16, or 14, and/or any other user interface, a request to generate a report R00 including one or more modules 710A-D. This request may include information, such as the identity of the patient, identity of the requesting device, a type of report being requested, and/or the like. The request may also specify a time frame for the report and/or as any other information required to authenticate the device requesting device or user.

At 720, one or more modules, such as the report modules disclosed herein, may be selected based on metadata including rules, templates, and/or the like. This metadata may describe one or more of the following: types of data available; amount of data; types of devices being used; user preferences; size of the user interface available to present report; patient demographics; patient information including report preferences, types and quantity of devices used, and display size being used to present the report, and other data related to the user, devices, and the like; rules, such as whether a module can be used with certain devices (for example, certain reports may only be suitable for continuous blood glucose, rather than discrete measurements), whether a module can be used with certain patient conditions (for example, a caregiver may establish a rule requiring a certain report based on a patient's demographic, history, or condition), whether a module may be used on certain display sizes, whether a module may be used given a certain volume of data or device type; and/or one or more templates. For example, the selection of modules may be performed based on metadata including user preferences for certain modules, a type of device being used, a display area of the device, and a rule defining which modules can be used given the type of device, a patient state/condition, and the display area of the device. Furthermore, the metadata may be stored at a repository, such as repository 475, although some of the metadata or may be provided as part of the request received at 710.

At 725, the report may be generated based on the modules selected at 720. For example, if the metadata indicates that the user prefers two specific modules (e.g., a first module for a continuous glucose monitor and a second module for a self-monitoring glucose monitor) and the metadata indicates that current device being used is a continuous glucose monitor, the report generator 420G may dynamically select the first module. However, if a second request is received but the metadata indicates that a self-monitoring glucose monitor is being used, the report generator 420G may dynamically select the second module. Moreover, the module(s) may be positioned in the report based on the predefined templates noted herein.

In some implementations, the analyte processor 490 may include one or more defaults for the report 700 including the modules therein. Moreover, the defaults may be dynamic, in the sense that the defaults vary based on the patient. For example, if a host has Type 1 diabetes, the default target glucose range may be defined as 70-180 mg/dL, and for Type 2 diabetes, the default target range may be defined as 90-130 mg/dL, although these defaults may be changed by a user, such as a clinician, a doctor, a patient, and the like. Moreover, the analyte processor 490 may base the report and/or certain modules on a default time frame of data, such as the most recent 30 days of data, although other default time frames may be used as well. Furthermore, if there is a gap in the data provided to the analyte processor that prevents 30 continuous days of analysis, the report may start at the most recent data and go back as far back as possible without exceeding the 30-day limit.

Figures 3, 6A:

FIG. 6A-3 depicts an example of a patient information module 605A. The patient information module 605A may provide information to identify a patient, such as a patient's name 605B, a date of a medical appointment 605C, an email address 605D, a condition 605E, and any other information that may be used to identify a user, such as a patient, a host, medical record number, and the like. In some exemplary implementations, patient information module 605A may be configured at a top portion of report 600 to enable quick identification of the patient. Although patient information module 605A depicts personally identifiable information (PII), such as name 605B and email address 605B, patient information module 605A may be configured anonymously to avoid disclosure of the PII information.

Figures 4, 6A:
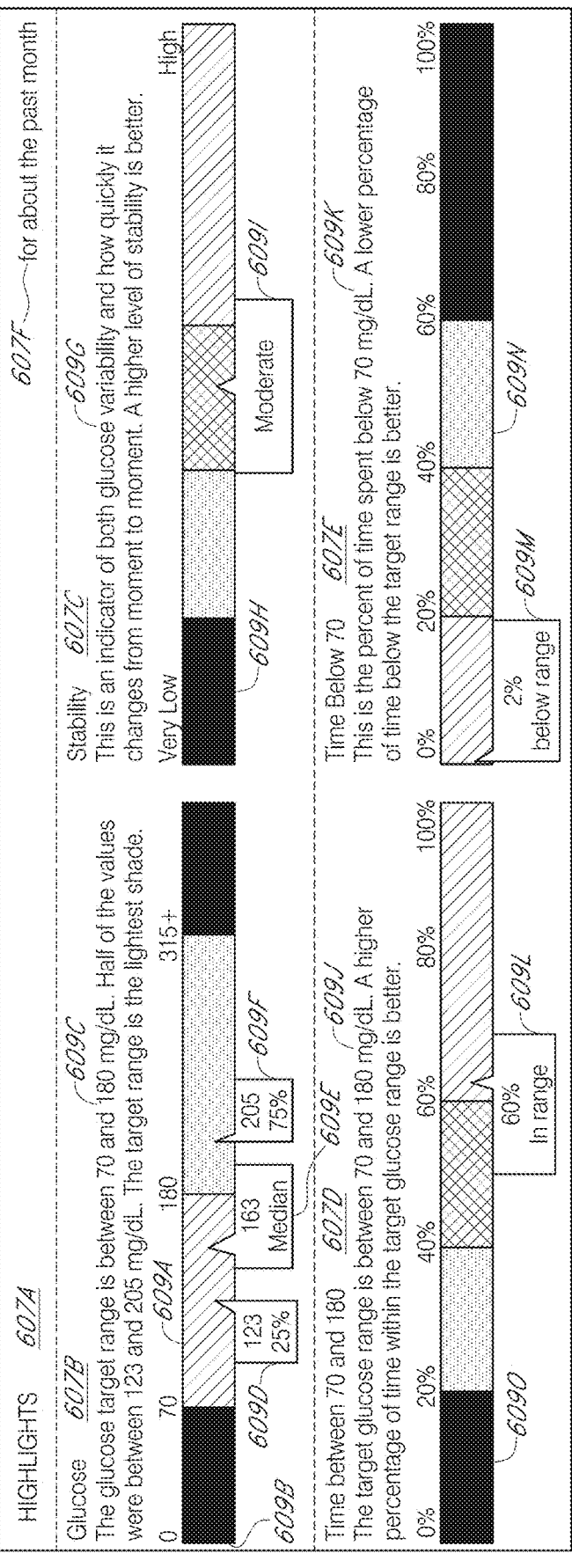
Figures 5, 6A:
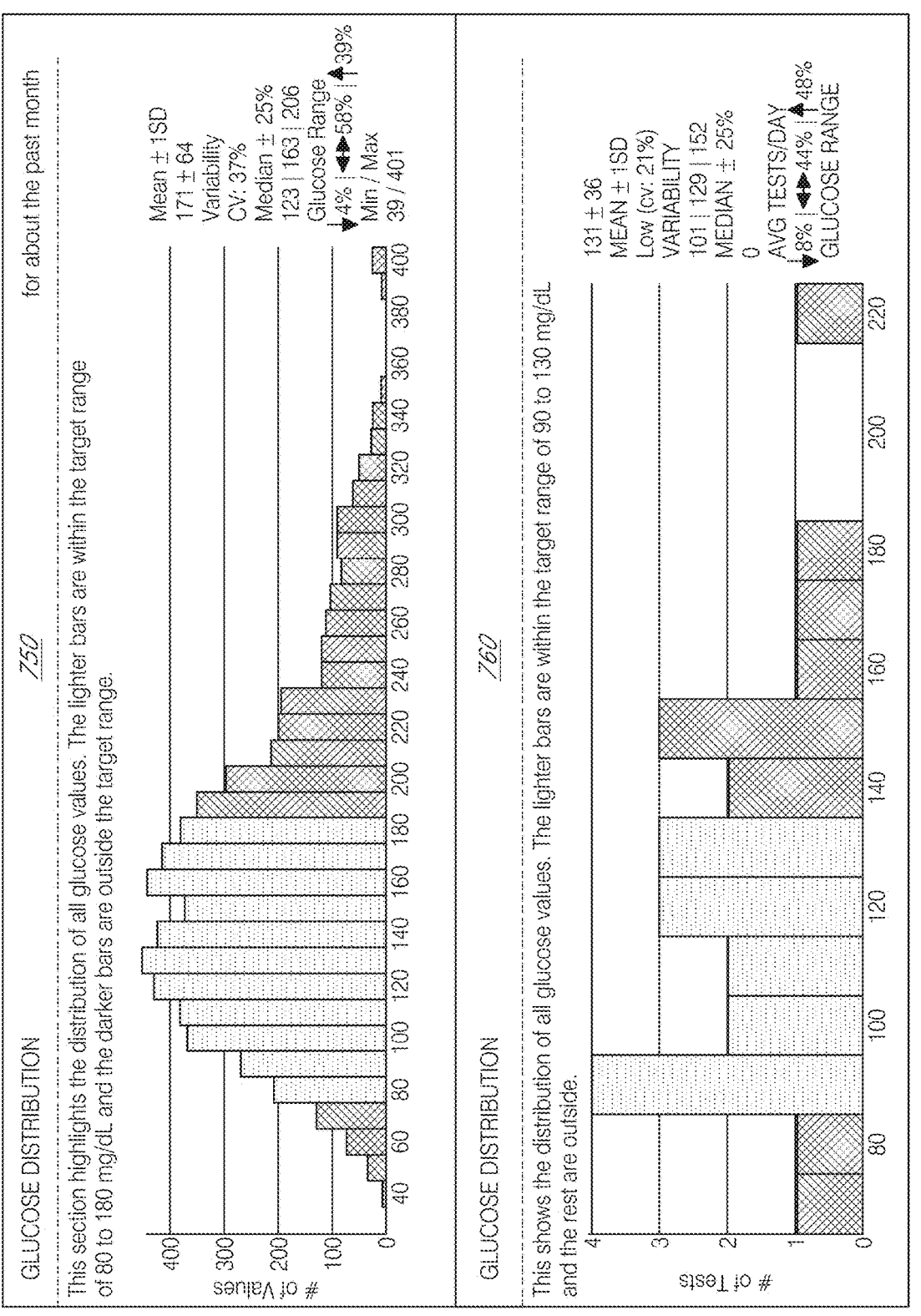

FIG. 6A-4 depicts an example of a highlights module 607A. The highlights module 607A may include one or more sub-modules 607B-E providing an abstraction of the data received and processed at analyte processor 490. In some exemplary implementations, the highlights module 607A provides an abstraction by distilling the details of data obtained over a time frame, such as 8 hours, 1 day, 2 days, 7 days, 30 days, and/or any other time period, into a graphical representation with some textual information. In the example of FIG. 6A, the time frame of the data is depicted at 607F (which in this example is about a month although other time frames may be used as well). The glucose module 607B may abstract 30 days of data provided by a continuous blood glucose sensor (which may represent large volumes of data likely to inundate a patient or clinician). This data may be abstracted into, for example, a graphical element, such as graphical bar 609A, and textual information, such as callouts 609D-F, to represent the percentage of time over the past 30-days that the patient was below, above, or at a target range.

In some exemplary implementations, the abstraction may convey complex statistical information in a graphical bar format. Furthermore, the graphical bar may represent different values, states, or conditions using different shading, and may include callouts including textual information to provide summary information, value help, and the like. The different shading may also be used to convey different states of a host or patient determined based on received data (e.g., counts, etc.). For example, the glucose module 607B may convey a target glucose range using the lightest shading 609A on the graphical bar 609B, while other shades may be used to represent other portions of the glucose range of a host. Although some of the examples described herein refer to using shading, other distinctive graphical elements may be used as well, such as colors, icons, or other elements.

In some implementations, each sub-module of the highlights module 607A uses a horizontal bar with different shading to denote ideal and less than ideal values. For example, the lighter the shade the more ideal the value. Moreover, the sub-modules may be different based on whether self-monitoring glucose concentration data values or continuous glucose monitor data values are being presented. For example, the title and descriptive text may indicate whether the module is continuous data or not, and in some instances, a sub-module may not be relevant if there is only non-continuous glucose data values (e.g., obtained from a finger stick meter) or only continuous glucose monitor data values. The glucose module 607B may include a textual legend 609C describing a target range for glucose measurements, the graphical bar 609B spanning a range of glucose measurement values and including one or more different shades (at least one shade 609A distinguishable from the other shades to enable representation of a target range), and callouts 609D-F.

In the example depicted at glucose module 607B, the shading corresponding to 180-315 denotes the range from the maximum target glucose range times a certain factor (e.g., 1.75), and the labels 25% and 75% denote the inner and outer quartiles which are distinctively shaded, although other shading schemes, ranges, and factors may be used as well.

The glucose module 607B may present statistical information determined for a host, such as a patient identified at 605B, over a time frame defined at report generator 420G by, for example, a user (e.g., a patient, a clinician, and/or programmatically selected by system 400). In the example of FIG. 6A, the time frame of the statistics is over a previous 30 days, although other time frames, such as an 8 hour period, daily, weekly, monthly, yearly, and the like, may be used as well. Moreover, the statistical information may be determined from data received at analyte process 490 for one or more devices, source systems, and the like. For example, the data may represent sensor data (e.g., continuous blood glucose data, insulin pump data, self-monitoring blood glucose data, carbohydrate consumption data, and the like) and/or metadata provided to analyte processor 490 and, in some exemplary implementations, be formatted in accordance with counts, although other data formats may be used as well.

In some exemplary implementations, the statistical information presented at glucose module 607A may be determined using 30 days of data stored at repository 475 in one or more histograms including counts, although other data formats may be used as well, including any other data format discussed herein. Although the previous example describes 30 days of stored data, other time frames may be used as well and the time frames may be selected by a user as well. Moreover, the graphical bar 609B may include a callout 609D including textual information indicating that over about the last thirty days 607F 25% of the glucose measurements received at analyte processor 490 from one or more devices were in the target range, and the callout 609D includes textual information showing that the inner quartile was 123. The callout 609E shows that the median over about the past 30 days was 163, and the callout 609E shows the outer quartile was 205.

FIG. 6A-5 depicts examples of glucose modules and, in particular, glucose distribution modules 750 and 760. The glucose distribution modules 750 and 760 each provide a graphical abstraction of the sensor data provided to analyte processor 490, which in the depicted examples represent glucose values. Glucose values within a target range are depicted with a graphically distinct indication, such as first, light shading, while values outside the glucose range are depicted with another graphically distinct indication, such as second darker shading. Textual information may be presented adjacent to the graphical abstraction. This textual information may include statistical information determined from the sensor data. For example, module 750 depicts a mean value of 171 for the given time frame, with a standard deviation of plus or minus 64, a median (e.g., 123) including quartile values (e.g., 163 and 206), an indication of the variation of the glucose values, such as a coefficient of variation (CV), which in this example is 37%, a glucose range including percentages and graphical indicators, a minimum glucose value (e.g., 39), and a maximum glucose value (e.g., 401). In the example of FIG. 6A-5, the arrows associated with the glucose range indicate above, at, or below the glucose range. Specifically, a host/patient may have a range of glucose values, and some of the measured glucose values may be below (e.g., 4%, which is represented by a down arrow), some may be within range (e.g., 58%, which is represented by a horizontal arrow), and some may be above the range (e.g., 39%, (which is depicted with a vertical up arrow). Module 760 depicts the textual information as well but in a different format. In any case, modules 750 and 760 provide a single view compressing over a month's worth of data into a graphical abstraction highlighting the frequency of occurrence of within range measurements and out of range measurements.

Referring again to FIG. 6A-4, the stability module 607C may include a textual legend 609G describing that stability measures glucose variability and its rate of change and that higher values of stability may be considered better for a patient. The stability module 607C may also include a graphical element, such as graphical bar 609H, presenting a range of glucose variability values using different shades and a callout 609I including textual information describing whether glucose variability over a certain time frame (which in this example is about 30 days 607F) is very low, low, moderate, or high.

In some exemplary implementations, the stability module 607C may present a metric that combines glucose variability (which may be determined as a coefficient of variation) and a quantity of instances and time spent within a state of rapid glucose change (acceleration). For example, analyte processor 490 may receive sensor data from data retriever 465, which obtains the data from a sensor, such as a sensor system 8. In this example, the glucose variability and the acceleration may be assigned a score with a range, such as 0 to 50, and a lower score may be considered better than a higher score. The variability score may be determined by normalizing the coefficient of variation for a certain time frame (e.g., 30 days and the like) to the score range of 0 to 50, where a coefficient of variation of 0.7 or higher receives a maximum score of 50. The acceleration score may be determined by sampling the rate of change of the sensor data stored in repository 475 as histograms and counts over a window (e.g., over a 15-minute window/interval) by evaluating the rate of change over the sampling window, measured as an estimated mg/dL/min (milligrams/deciliter/minute) based on the rate of change of the current and previous sampling windows. The combined variability and acceleration score, which is a weighted mg/dL/min, may be calculated over some, if not all of, the sampling windows for the time frame of the report or module 607C, and then normalized to a scale from 0 to 50, for example. In this example, a weighted equivalent of 6 mg/dl/min or higher may receive a score of 50. The variability and acceleration scores may then be combined (e.g., added) to determine the location of the callout 609I on the graphical bar 609H.

In some exemplary implementations, the stability module 607C may only be included in report 600 when sensor data from a continuous glucose monitor is available for processing.

Moreover, although the previous example describes that the stability module 607C present a metric that combines coefficient of variation and acceleration, stability module 607C may be configured to provide a metric representative of one of the coefficient of variation or the acceleration as well.

Although the previous example describes specific numerical values, units of measure, and the like, these values and units of measure are only exemplary as other values may be used as well.

The time between module 607D may include a textual legend 609J indicating that a target range for glucose measurements is between two values (e.g., 70 and 180 mg/dL) and that a higher percentage of time spent within the target range is typically better for a patient. The time between module 607D may also include a graphical element, such as a graphical bar 609O, presenting a percentage range visually using different shades, and a callout 609L including textual information representing the percentage of time that the glucose measurements are within the target range. In some implementations, the time between module 607D is generated when continuous glucose sensor data is available from a continuous glucose monitor. But when only non-continuous glucose data is available (e.g., only data available from a self-monitoring blood glucose monitor), the time between module 607D may instead be configured to represent time between tests performed using the self-monitoring blood glucose monitor or the percentage of self-monitoring blood glucose tests between the range.

The time below module 607E may include a textual legend 609K describing that the percentage of time spent below a certain value, such as 70 mg/dL, is typically better for a patient. The time below module 607E may also include a graphical element, such as graphical bar 609N, presenting a percentage range using one or more different shades, and a callout 609M including textual information representing the percentage of time that the glucose measurements are less than the certain value, which in this example is 70 mg/dL. In some exemplary implementations, the time below module 607E is generated for continuous glucose monitor data, but when only self-monitoring blood glucose monitor data is processed, the time below module 607E may instead be configured to represent time between tests performed at the self-monitoring blood glucose monitor. Although module 607E is depicted as a time (or tests) below presenting a percentage, the module 607E may be configured as a time (or tests) above module presenting a percentage of time (or tests) that glucose values are above a certain value.

Figures 6, 6A:
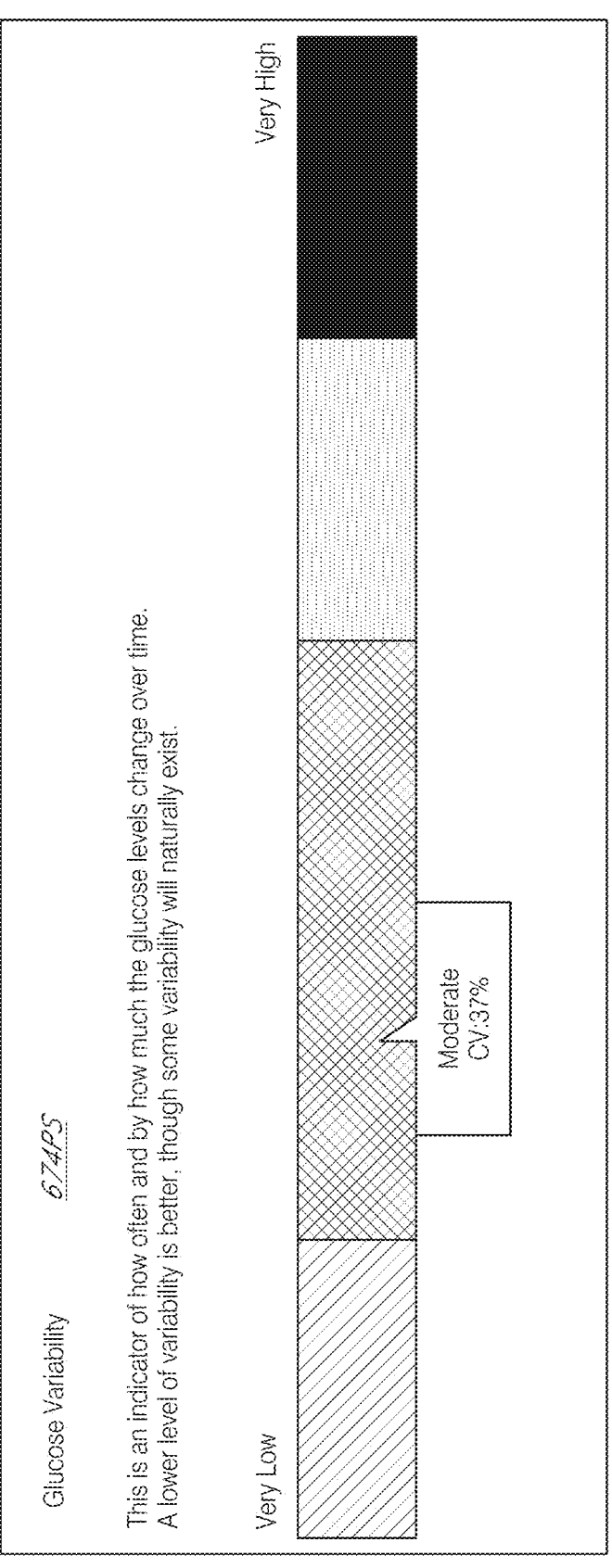

FIG. 6A-6 depicts an example of a percentage tests above module 674PS, which is similar to the time below module 607E but shows the percentage of time above the target range.

Figures 6, 6A, 7:
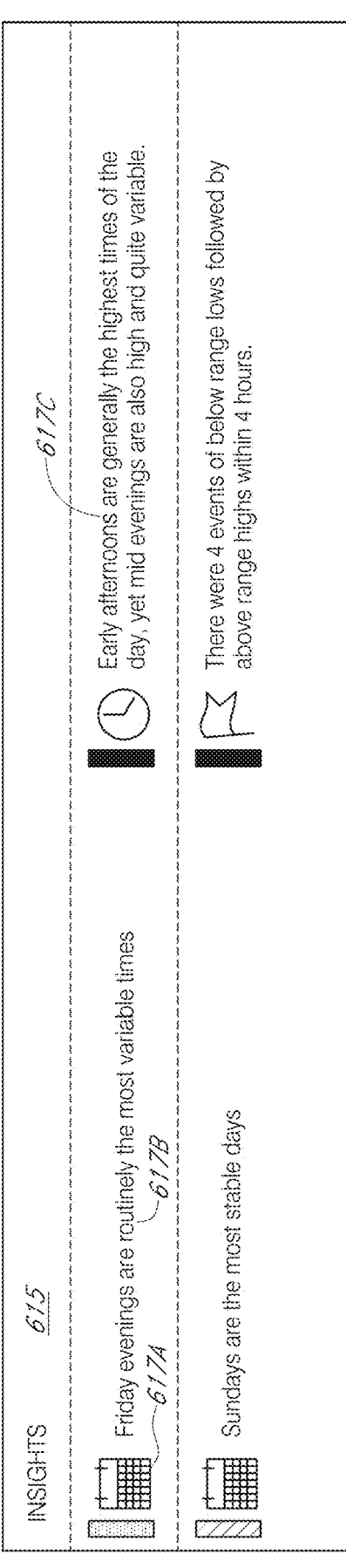

FIG. 6A-7 depicts an example of an insights module 615 configured to provide an abstraction of one or more patterns detected based on a patient's data processed by analyte processor 490. In some exemplary implementations, an insight includes a graphical element 617A, such as an icon, and textual information 617B. For example, insight 617C may represent one or more patterns detected by analyte processor 490 (and in some exemplary implementations pattern detector 420I) over a certain time frame, such as over an 8 hour period, 1 day, 2 days, 7, days, 30 day period, and the like. Furthermore, the patterns may be so-called "hard coded" to trigger once an event is detected in the data. For example, a pattern may detect high glucose concentration levels above a target glucose range and then correlate those with days of a week and times of day to determine whether a patient experiences high blood glucose during a specific day or time. In this example, a detected pattern may correspond to detecting that a patient has a high glucose concentration level every evening after 8 PM or has a high glucose concentration level on Sunday evenings for the past 30-days. Furthermore, pattern detector 420I may, in some exemplary implementations, detect the pattern based on the histograms and counts covering the past 30-day period. Other patterns may be detected, based on data from the sensors and/or metadata, and presented as well by insights module 615. For example, metadata may indicate the patient has Type II diabetes and using certain devices, such as a self-monitoring blood glucose monitor and an insulin pump. In this example, the metadata may be used to determine what patterns to use for detection and what insights (and how many) to present at the insights module 615.

In some exemplary implementations, the insights presented at insights module 615 may be weighted to emphasize certain insights or events and then ranked to enable presentation of some, rather than all, of the insights, which may be detected by analyte processor 490 and/or pattern detector 420I. For example, the insights module 615 may be configured to include more (or fewer) insights based on user preferences, quantity of devices providing data to analyte processor 490, and/or type of devices providing data to analyte processor 490. The insights may also be processed to determine a strong correlation for a given patient, so that insights presented at report 600 are those in which there is a high degree of confidence that the insight represents the patient's actual state. Furthermore, similar patterns may be merged, and weighting may be used to emphasize a positive insight over a negative insight (and vice versa).

In some exemplary implementations, the insights presented at insights module 615 may be associated with one or more patterns being detected by pattern detector 420I. Examples of patterns include a pattern for glucose values within a target glucose range, a pattern for glucose values above a target glucose range, a pattern for glucose values below a target glucose range, a pattern for detecting rapid changes from high to low glucose values (and vice versa), a pattern for high coefficient of variance, and the like. In some exemplary implementations, each pattern at pattern detector 420I may have a single dimension, so that a separate pattern is used to search specifically for a below range pattern, another pattern looking for low coefficient of variance, and the like. In some exemplary implementations, each pattern at pattern detector 420I may be statistically based and use standard descriptive statistics. In some exemplary implementations, each pattern at pattern detector 420I may be assigned a score or a weight to indicate its relative importance with respect to other patterns. In some exemplary implementations, each pattern at pattern detector 420I may be assigned an applicable time frame over which it performs its pattern detection.

To further illustrate examples of the patterns, basic patterns may be configured to allow a search for certain patterns in the data, such as values within range, high coefficient of variance, and the like. Each pattern may have one dimension, such as within range, with a separate pattern looking specifically for below range, another looking for low coefficient of variance, and the like. Each pattern may be statistically based and use standard descriptive statistics in the application of pattern matching. Each pattern may be assigned scores for various rules encoded with each pattern, such as is it positive, negative, how important an insight is, and the like. Each pattern may also be assigned a possible set of date ranges for which the pattern is applicable. For example, counting the number of times a high glucose value is followed by a low below range is a pattern that just applies to the full range. However, looking at high levels of variance can apply to a month, a week, a day, an intraday, every other hour, hourly, and combinations thereof. Every pattern may be assigned a minimally acceptable score before it can be considered for display. Each pattern (and any associated rules) may be processed for a set of data for a certain time frame, and if the pattern is applied and meets certain minimal requirements, then the patterns are ranked according to significance. As such, the ranked patterns may each correspond to an insight, resulting in a ranking of the insights. For example, insights module may only present a portion, such as the top five insights, although other quantities of insights may be configured for presentation as well.

The insights module 615 may present statistical patterns over a time frame of the report. Moreover, the specific insights representative of statistical patterns may be presented with the highest correlation for that patient. For example, before a certain insight is presented, analyte processor 490 may perform post-processing, such as merging similar statistical patterns together, giving a slight weighting to a positive insight over a negative one (or vice versa), and the like. The insights selected may be considered deterministic in the sense that insights are generated the same each time when the time range, patient information, and health data are exactly the same.

FIG. 6A-8 depicts an example of a high and low period module 620A. The high and low period module 620A highlights patterns of high and low periods for data measured over a predefined period of time, such as 1 day, 2 days, 7 days, 30-days, and other time frames as well. In this example, the high and low period module 620A depicts that over the last 30-day period 622A, the patient providing sensor data to analyte processing engine 490 has had patterns of high instances of glucose (e.g., above a defined target range) detected at 622B-I. These highpoints, such as high point 622E, may show a pattern of high glucose during the evening hours. The high and low period module 620A also shows that no low points occurred. Should analyte processor patterns of low glucose be detected, then the low glucose patterns may be displayed in a similar fashion as to the high glucose patterns, although inversed. In some exemplary implementations, analyte processor 490 including pattern detector 420I may detect the high and low events depicted at the high and low module 620A. Moreover, the detection may be based on patterns (e.g., a pattern may define a feature to identify or detect in data received and/or stored at system 400 and/or repository 475. Furthermore, the area under the graphed portions may be shaded to convey whether the high or low period exceeded a threshold. For example, the area under high portion 622I may be shaded to show that the high was of particular interest (e.g., exceeded a magnitude threshold, which can be the upper target range threshold, for a time period exceeding a threshold value). Moreover, a plurality of thresholds (and shadings) may be used to convey other areas of interest with respect to the graph, such as patterns of relatively higher highs (or longer time periods being high) or lower lows (or longer time periods being low) being detected using different thresholds and presented using different shadings.

FIG. 6A-9 depicts an example of a devices used module 630. The devices used module 630 may include a textual legend 632A describing each device providing data for analysis and reporting by analyte processor 490, a graphical element, such a graphical bar 632B including different shades to present a range of time the device is actually in use, and a callout 632C providing textual information regarding the percentage of time the device was in use over a certain time frame, such as 1 day, 2 days, 7 days, 30-days, and the like. In the example of FIG. 6A-9, only a single device is depicted, but if a given patient provides data to analyte processor 490 using additional devices, those additional devices would also be depicted with textual legends, graphical bars, and callouts providing the percentage of time the device was in use over a time frame.

In some exemplary implementations, the devices used module 630 may also include whether a clock at the device is incorrect and whether any corrections were made by analyte processor 490. For example, data retriever 465 may determine that a device clock is off (or in error) by a certain amount, and report that amount to analyte processor 490. When this is the case, the devices used module 630 may show this error amount. In some exemplary implementations, the analyte processor 490 shifts the data from the device to compensate for the error and provide coherency with other data, in which case the devices used module 630 may show the amount of time shift.

FIG. 6A-10 shows additional examples of devices used including a devices used module 733A for a continuous glucose monitor, devices used module 733B for a self-monitoring blood glucose monitor, and devices used module 733C for an implementation including a plurality of devices, such as a continuous glucose monitor and a self-monitoring blood glucose monitor. FIG. 6A-10 also illustrates the dynamic nature of the report and module generation as 733C is configured dynamically based on the devices being used by the patient. FIG. 6A-10 also shows the time shifting feature to show the differences (or errors) in the clocks of the devices.

FIG. 6A-11 depicts an example of a compared with module 640. The compared with module 640 may present a statistical comparison between a patient, such as a patient identified at 605B, and a group, such as cohorts. The compared with module 640 may include a textual legend 642A describing what the other group is (e.g., other patients at a clinic), a graphical element, such as a graphical bar 642B including one or more different shades to present a range of values, and callouts 642C-D. In the example of compared with module 640, the callout 642B provides a textual indication of the percentage of time the device was in use over a certain period, such as 1 day, 2 days, 7 days, 30-days 605E, and the like. In the example of FIG. 6A-11, the graphical bar 642B and the callouts 642C-D compare a patient 605B and other clinical patients 642A, and this comparison is based on data obtained from the patient and other clinical patients over a given time frame, such as 1 day, 2 days, 7 days, 30 days 607F, and the like. And, the comparison relates to the time a patient is below a target glucose range (2% as show by callout 642D) and the time the other patients at the clinic are below the target glucose range (7% as shown by callout 642C) based on data collected over a 30-day time frame, although other statistical comparisons, time frames, and groups may be used as well. In some exemplary implementations, the statistical comparisons shown with respect to the compare with module may be determined based on histograms and counts disclosed herein. Moreover, the analyte processor 490 may programmatically chose the group 642A used as a cohort, although a user may choose the group as well. The group 642A may be selected based on metadata representative of one or more of the following: diabetes type, age, sex, age of diagnosis, location, treatment facility, type of sensor device used and any other factor or demographic, such as any type of metadata discussed herein. In some exemplary implementations, the analyte processor 490 may programmatically select a group most similar to the patient 605B, although other selection schemes may be implemented as well.

FIG. 6A-12 depicts another example of a compared with module 674XY. The compared with module may be generated by the report generator to compare the host with another user or groups of users (e.g., cohorts). In the example at FIG. 6A-12, the patient is being compared with all the patients within a clinic for a certain range, such as percentage of glucose concentration levels below and above a target glucose concentration range. In this example, the patient is below the range 16% of the time and above the range 29% of the time, while the group is below the range 27% of the time and above the range 56% of the time. Although the previous comparison compared the patient with cohorts associated with the same clinic as the patient, other groups or comparisons may be made as well. For example, analyte processor 490 may include metadata to allow comparisons based on one or more of the following: diabetes type, age, gender, age of diagnosis, and the like.

In some implementations, the analyte processor 490 may programmatically select a group to compare with the patient in a compare with module, and this selection may be made in order to identify a group that is most similar to the patient. Moreover, this selection may, in some implementations, be weighted to favor a group in which the patient compares slightly better than those in the group. And, this selection may be programmatically determined. For example, analyte processor 490 may determine all potential cohorts that a user belongs to, and choose the group that has a slight positive association. Analyte processor 490 may also determine a difference value between all the cohorts and the patient (e.g., by comparing the same statistic) and choose the cohort that has the smallest difference (which may be the one that is most similar to the patient). Moreover, the difference that is positive may be selected over a difference that is negative. For example, given a patient that has a glucose concentration that is out of range 16% of the time, a clinic having patients which are out of range 18% of the time may be selected over other cohorts or statistics, having a negative difference (e.g., when compared to another group having a negative difference, such as a group of cohorts which are out of range 15% of the time). In addition, if there is no positive difference, analyte processor 490 may search for slightly negative differences, so a slightly negative correlation may trump one that is significantly positive. Returning to the previous example of glucose concentrations out of range, if the 18% group did not exist, the analyte processor 490 may select the slightly negative group at 16%.

Referring to FIG. 6A-13, the daily summary module 650 may provide a modal day view of the glucose data collected over a given time frame, such as about the past month 652A, for one or more devices providing data for a given patent, such as patient 605B. In some implementations, the data presented to the patient may be selected to encourage the patient (e.g., by showing the patient is doing well). The daily summary module 650 provides an indication of a patient's daily fluctuations over a given time frame.

In the example of daily summary module 650, the x-axis 652B represents a first time period, such as 24 hours, and the y-axis 652C represents a measured value, such as glucose value. Analyte processor 490 may determine statistics, such as percentage of time within a target glucose range (labeled within range), a median glucose value, a middle 50% range of glucose value measurements, and a variability of the glucose measurements, based on 30-days' worth of sensor data, although other time frames may be used as well. In the example of daily summary module 650, median and quartile range are depicted, although other determined statistics may be presented as well. Moreover, the determined statistics may be categorized based on times of day, such as specific times or periods (e.g., within epochs or more generally, such as morning, afternoon, etc.). Once categorized, the determined statistics may be presented in a module, such as daily summary module 650.

In some exemplary implementations, the daily summary module 650 may plot over a first time frame, such as a 24-hour period, median glucose values with a distinctive element 652D, such as a bold line or object, and the middle 50th percentile of glucose values are plotted with another distinctive element 652E, such as light shading, and a target glucose range is depicted by two distinctive elements 652G-H, shown as lines at 70 and 180 mg/DL, for example.

When the daily summary module 650 shows self-monitoring blood glucose data, each individual test (or a lower density form of the data) may be displayed as an element, such as a dot. FIG. 6A-14 depicts an example of a daily summary module 769A configured to show self-monitoring blood glucose data.

Referring again to FIG. 6A-13, when the daily summary module 650 contains continuous blood glucose monitor data, each of the individual measurements may not be plotted, but instead the median ±25% may be plotted, with slight shading indicating the interquartile range. In some exemplary implementations, the median and interquartile range values are computed at 30-minute resolutions. In some exemplary implementations, when only self-monitoring blood glucose data is plotted, the shading is lighter and faint dashed lines are used, and when continuous blood glucose monitor data is included, the shading is darker and solid lines are used to provide a distinction between the types of data sets. In some exemplary implementations, the analyte processor 490 computes the median and interquartile range to allow presentation at daily summary module 650 using a c-spline smoothing algorithm, such as the Fritsch-Carlson Monotone cubic Hermite interpolation, although other approaches may be used as well.

In some exemplary implementations, the daily summary module 650 may include a textual summarization 652F. For example, the textual summary 652F may include standard descriptive statistics (e.g., median, middle 50% (the IQR), variability (the CV), and percent within range), grouped by intraday time ranges, such as night, morning, midday, after-noon, and evening. Each statistic may be computed in full using all the values in the report range, broken down by their time group, without using sampling or weighted merges.

FIG. 6A-15 depicts another example of a daily summary module 690A. In this example, the daily summary module 690 depicts a daily view of data from a plurality of sources, which in this example corresponds to glucose data 690B, carbohydrate consumption data 690C, and insulin pump data 690D. The daily summary module 690A plots the glucose data 690B in a manner similar to 650. However, the carbo-hydrates 690B are presented using a plurality of shades representing a range of different carbohydrate consumption values (e.g., a given shade represent a given carbohydrate consumption), and the insulin pump data 690D is present as a bar graph.

FIG. 6A-16 depicts another example of a module provid-ing a day-to-day view of the host/patient's analyte levels, such as glucose, and other values. The day-to-day details module provides a summary including glucose levels 7100 and carbohydrate levels 7200, where the measured intensi-ties are presented using different graphical indicators, such as darker shading, to show the different values of glucose or carbohydrates. The module at FIG. 6A-16 also depicts insulin dosage 7300 including amounts and times taken, with callouts, such as "1", "2", and so forth with a corre-sponding textual description of the dosage events. For example, callout "1" 7400 corresponds to textual description 7420. The module may also include a summary 7500 including statistical data, such as average glucose, total carbohydrates, total insulin, basil insulin, and bolus insulin. The day-to-day details module provides a single view (which can be present as a single page at a user interface) compressing a days' worth of data into a graphical abstrac-tion correlating measurements among dosage, carbohy-drates, and measured glucose to enable a host/patient to readily perform a visual correlation among carbohydrates, glucose, and dosage events.

FIG. 6A-17 depicts another example of a daily summary module. In this example, the daily summary module depicts a daily view of data from a plurality of sources, which in this example corresponds to glucose data, carbohydrate con-sumption data, and insulin pump data. The daily summary module at FIG. 6A-17 presents discrete data, such as SMBG data, as indicated by the data points 769A, 769B, and so forth. Moreover, the insulin dosage depicts the actual dosage functions/profile 769C. The daily summary module provides a single view (which can be presented as a single page at a user interface) compressing an extended timeframe, such as 29 days and/or any other time period, into a graphical representation correlating measurements among dosage/ pump data, carbohydrates, and measured glucose to enable a host/patient to readily perform a visual correlation among carbohydrates, glucose, and dosage events.

FIG. 6A-18 depicts an example of weekly summary module 660. Module 660 may be implemented in a manner similar to the daily summary module 650, but present data over a 7-day period as shown by the x-axis 662A, rather than a 24-hour period. In some exemplary implementations, the resolution of the data presented at the weekly summary module 660 may be calculated over 2-hour period, although other resolutions may be used as well.

FIG. 6A-19 depicts another example of a weekly sum-mary module 692A. Weekly summary module 692A may be implemented in a manner similar to the daily summary module 650, but present data over a 7-day period, rather than a 24-hour period. In this example, the weekly summary module 692A depicts a daily view of data from a plurality of sources, which in this example corresponds to glucose data, carbohydrate consumption data, and insulin pump data. FIG. 6A-20 depicts an example of a weekly summary module 769B configured to show self-monitoring blood glucose data.

FIG. 6A-21 depicts an example of an over time summary module 694A. The over time summary 694A may be similar to the daily and weekly summary modules disclosed herein, but the over time summary 694A plots the glucose values over time, using the median value at 12 to 18 hour intervals depending on whether or not continuous glucose monitoring data is included.

FIG. 6A-22 depicts an example of a continuous glucose levels module 670A. Module 670A presents in a graphical form the times when a patient was within, above, or below a target glucose range based on retrospective data obtained over a time frame, such as 8 hours, 1 day, 2 days, 7 days, 30 days, and the like. The continuous glucose levels module 670A may include a legend 670B, an indication of the time period 670C over which the information is plotted, and one or more graphical elements 670D-J and so forth, such as bars, icons, and the like, for one or more intervals within the time frame 670C.

In some exemplary implementations, the y-axis represents days of the week during the time frame 670C and the x-axis represents times (or epochs) during the time frame. For example, graphical element 670D depicts a glucose value over range condition on Friday April 6th, at about 12 AM and followed by another graphical element 670E represent-ing that the glucose value is within range, and graphical element 670K represents glucose values being under the target range on Wednesday at about 4 AM.

In some exemplary implementations, the graphical ele-ments for above a target range, below a target range, and at the target range are distinctive. For example, the above the target range 670D is depicted as a bar above the at the target range 670E, which is depicted as a line. The below the target range 670K is depicted below the at the target range line 670L. Moreover, the graphical elements may include value help and other information. For example, selecting a graphi-cal element presented on a computer may provide additional information regarding the glucose values, such as providing actual values for the glucose values above the range as depicted at 670G (e.g., "352") and K (e.g., "57"), or glucose values below the range.

In some exemplary implementations, the target range for glucose values may be select by a host, although other entities, such as clinicians, health care providers, and system 400 may select the target range as well. Moreover, the at the target range and below the target range may be detected, in some exemplary implementations, by pattern detector 420I based on one or more patterns. For example, pattern detector 420I may include a pattern that processes sensor data (or histograms and counts) stored in repository 475, identifies glucose values that are above the target range, and correlates dates and times of the above the range glucose values to enable presentation at glucose values module 676A. The pattern detector 420I may include a pattern that processes sensor data (or histograms and counts) stored in repository 475 to identify below the target range glucose values. In some exemplary implementations, the pattern detector may perform the weighting and/or thresholding of glucose values. For example, the pattern detector 420I may weigh the glucose values using a function (e.g., equalize, normalize, or map to some other function). The weights may ensure accurate detection of high and/or low glucose events for reporting via a report module, such as daily summary module 650. Moreover, the pattern detector 420I may use one or more thresholds to ensure that the high and/or low glucose events are indeed events that should be reported as high and/or low glucose events.

In some exemplary implementations, the pattern detector 420I may also detect rapid changes of glucose and correlate dates and times of the rapid change to enable presentation at glucose values module 676A. Moreover, the rapid shifts may be presented in a report, such as continuous glucose levels module 670A.

In some exemplary implementations, the continuous glucose levels module 670A may label or highlight so-called "outliers" representative of a peak high glucose value within an epoch or a peak low glucose value within an epoch. Referring to continuous glucose levels module 670A, an outlier is labeled as having a value of 352 mg/dL at 620G. The continuous glucose levels module 670A may also label or highlight rapid changes in glucose value from low to high (or vice versa).

In some exemplary implementations, the pattern detector 420I may attempt to limit the quantitative data presented at continuous glucose levels module 670A. For example, presenting hundreds of outliers and rapid shifts in glucose values at continuous glucose levels module 670A may inhibit the ability of a user to understand the data presented at continuous glucose levels module 670A. As such, pattern detector 420I may process the glucose values corresponding to outliers and rapid shifts until only a subset of the outliers and rapid shifts are detected. For example, pattern detector 420I may process the glucose values corresponding to outliers and rapid shifts until only about 30 outliers and rapid shifts are detected, and those may be presented at continuous glucose levels module 670A (see, e.g., "352" at 620G, "57" at 620K, and so forth.

To process sensor data (or representative counts and the like) until only a subset of the outliers and rapid shifts are detected, the pattern detector 420I may processes, in some exemplary implementations, all of the data for the time frame of the report or module, e.g., 30 days, and identify the above the target glucose range outliers, the below the target glucose range outliers, and the rapid shifts. Next, pattern detector 420I may then filter some of those values based on a threshold and a window. For example, a threshold may be applied to identify the top 8% of the above the target glucose range outliers and the bottom 8% of the below the target glucose range outliers. The pattern detector 420I may also apply a window to shift through a portion of the data to detect the rapid shifts. For example, all of the data may be processed with a 4-hour window to identify rapid glucose shifts from low to high (and high to low). After applying the threshold and window, the pattern detector 420I may determine how many high outliers, low outliers, and rapid shifts remain. If the remaining quantity of high outliers, low outliers, and rapid shifts is at or below a presentation threshold (e.g., 30 outliers and rapid shifts events presented for a 30-day presentation of continuous glucose levels), the pattern detector 420I may provide the remaining high outliers, low outliers, and rapid shifts to report generator 420G for presentation at continuous glucose levels module 670A. If the remaining high outliers, low outliers, and rapid shifts are above the presentation threshold, the pattern detector 420I may vary the threshold and the window size to reduce the quantity of high outliers, low outliers, and rapid shifts. For example, the thresholds may be reduced from 8% to 7%, and the 4-hour may be reduced to 3.6 hours. This process may be iterative until the quantity of outliers and/or rapid shifts is at or below the presentation threshold.

FIG. 6A-23 depicts another example of a continuous glucose levels module 670Z. In the example of FIG. 6A-23, glucose values above a target range are depicted with a shading 670Y that can be distinguished from a shading 670W used for glucose values below a target range and shading 670X used for glucose values at a target range, although continuous glucose levels module 670Z may use positional distinctiveness among graphical elements as well as in the case of continuous glucose levels module 670A. For example, the above the target range is depicted as an element 670Y above the bar 670X at the target range 670X, while the below the target range element 670W is depicted below a corresponding at the target range bar 670V. Although FIG. 6A-23 depicts using both shading distinctiveness and positional distinctiveness to distinguish the high, at, and low glucose values, each may be employed without the other.

FIG. 6A-24 depicts another example of a continuous glucose levels module 770. The module 770 may be similar in some respects to the other continuous glucose levels modules disclosed herein, but continuous glucose levels module 770 uses shading and size to convey intensity. Specifically, at 774, the glucose level is extremely far from a target glucose range as depicted by the darker shading at 772 and the vertical size of the block. By contrast, at 776, the excursion from the target glucose range is somewhat less than at 778, when the darker intensity shading drops to a lower intensity level as well as a lower vertical size. Module 770 may also use thin bare 780 to depict periods where the host patient is in range, and periods where there is no data may be presented as no shading (or color) is shown, such as at 782. Although module 770 depicts the first four days of a period, module 770 may depicts other timeframes as well. Module 770 thus abstracts the time above or below a range into an easy to view graphic depicting how much a patient/host is out of range with a visual indicator, such as intensity.

FIG. 6A-25 depicts another example of a continuous glucose levels module 676A. The continuous glucose levels module 676A may be similar in some respects to the continuous glucose levels module 670A and the like, but the continuous glucose levels module 676A includes graphical elements that are distinctive only with respect to shading (e.g., coloring, intensity, contrast, and the like), so that glucose values above a target range are depicted with a shading 676B that can be distinguished from a shading 676C representative of glucose values below a target range and a shading 676D representative of glucose values at a target range.

FIG. 6A-26 depicts an example of a glucose meter value levels module 674A. The glucose meter value levels module 674A may be similar in some respects to the continuous glucose levels module 670A and the like, but glucose meter value levels module 674A shows discrete values associated with the glucose measurements (e.g., made by a self-monitoring blood glucose meter) and may also include graphical elements, such as a substantially circular icons 674B-C to depict a certain percentage of the highest glucose values above a target range and substantially polygonal icons 674D-E to depict a certain percentage of glucose values below a target range. The average and variability for each day may also be listed to the right, with a variability's displayed for a given day only if there are more than two glucose values provided for that day. In some implementations, when a patient is using a self-monitoring blood glucose device and a continuous glucose monitor and providing their data to analyte processor 490, the report generator generates two types of reports, such as a continuous glucose level module 670Z and a discrete glucose meter values 674A. Moreover, processing by analyte processor 490 is transparent in the sense that analyte processor 490 can processor both types of data and generate reports regardless of the source or type of data.

FIG. 6A-27 depicts another example of a glucose meter value levels module 674AA. Glucose meter value levels module 674AA is similar to glucose meter value levels module 674A in many respects but includes arrows to depict above or below the range. For example, 674AB depicts an up arrow, and 674AC depicts a down arrow. Other indicators may be used as well to depict intraday highs or lows in glucose data. Moreover, markers may be used to segment the time shown into periods, such as morning, afternoon, evening, and night, to assist the user in interpreting the data presented.

FIG. 6A-28 depicts a report legend 687A, which may be placed as a module in report 700. In some implementations, the report legend module 687A may be placed as the last module or section of the report, and may include a description and explanation for various sections of the report.

FIG. 7 depicts an example of a testing frequency of a self-monitoring blood glucose testing frequency module 700. The self-monitoring blood glucose testing frequency module 700 includes epochs, such as weekdays 702 and weekend 704, and corresponding time intervals 706 during those time periods. The circles represent that a host has taken a measurement. For example, circle 708A represents that the host made one or more measurements of blood glucose at 1 AM during the week 702, and circle 708B represents that the host made one or more measurements of blood glucose at 1 AM during the weekend 704. The larger the circle the greater the number of measurements made at the corresponding time period and interval. For example, circle 710B is larger than circle 708B, and, as such, circle 710B represents that the host made more blood glucose measurements at 8 AM, when compared to 1 AM. The report generator 420G may generate self-monitoring blood glucose testing frequency module 700 based on counts and corresponding histograms generated by calculation engine 420H.

Figures 6, 6A, 7, 8:
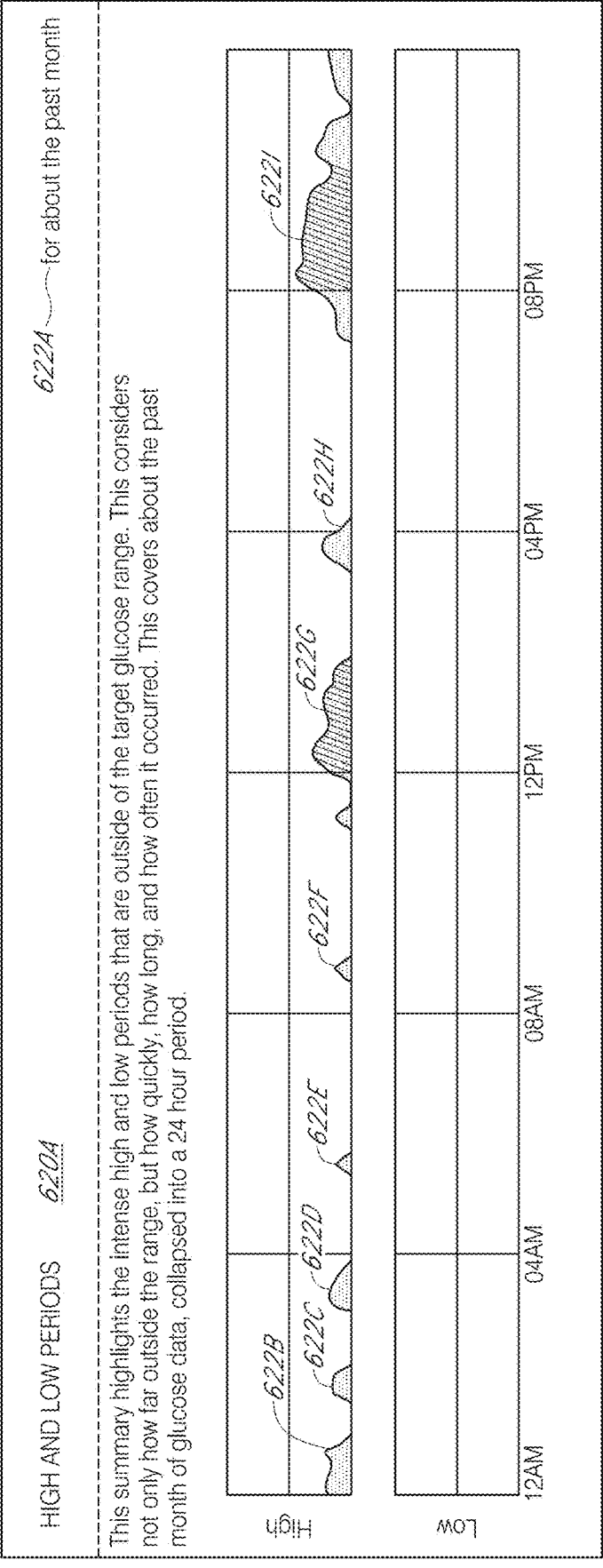

FIG. 8 depicts an example of a patient questions module 899. The patient questions module 899 may be configured to allow a user, such as a clinician, doctor, and the like to pose questions to a patient via a report including patients questions module 899 presented at a user interface. If questions are asked, the patient's answers may be captured and included in the report. The patients questions module 899 may include a standard set of default questions (e.g., obtained from the American Diabetes Association Standards of Care manual), which are selected by the user or programmatically by analyte processor 490.

Figures 6, 6A, 7, 8, 9:
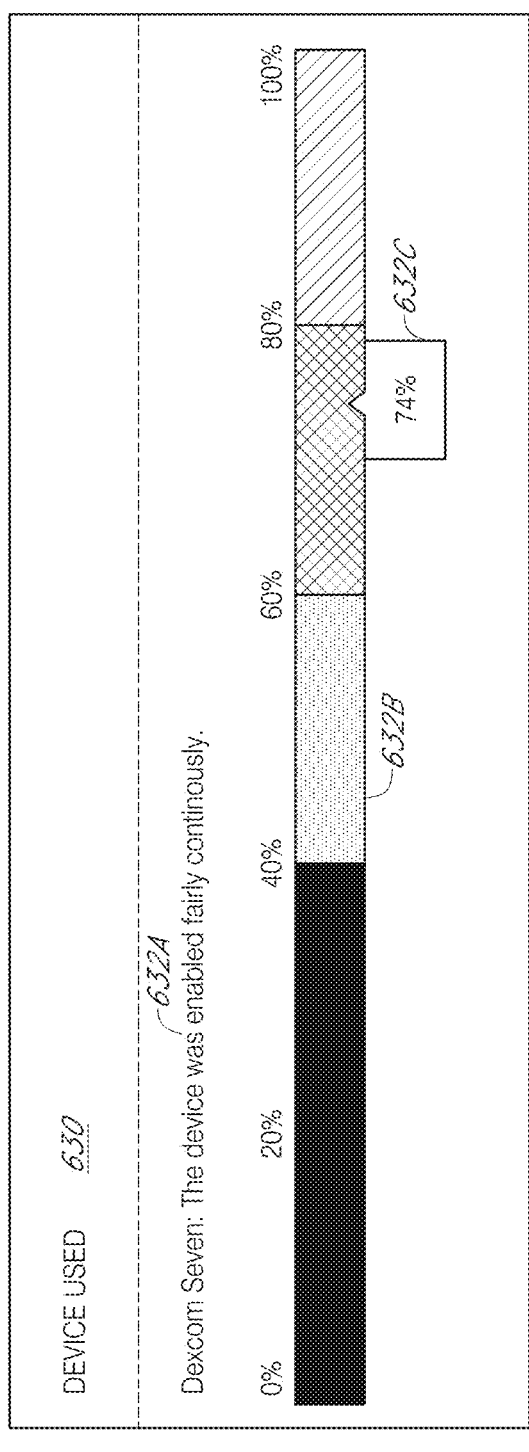

FIG. 9 depicts another example of an insights module that includes a patient question within the same module (e.g., "a high number of glucose checks are within range").

Figures 6, 6A, 7, 8, 9, 10, 11:
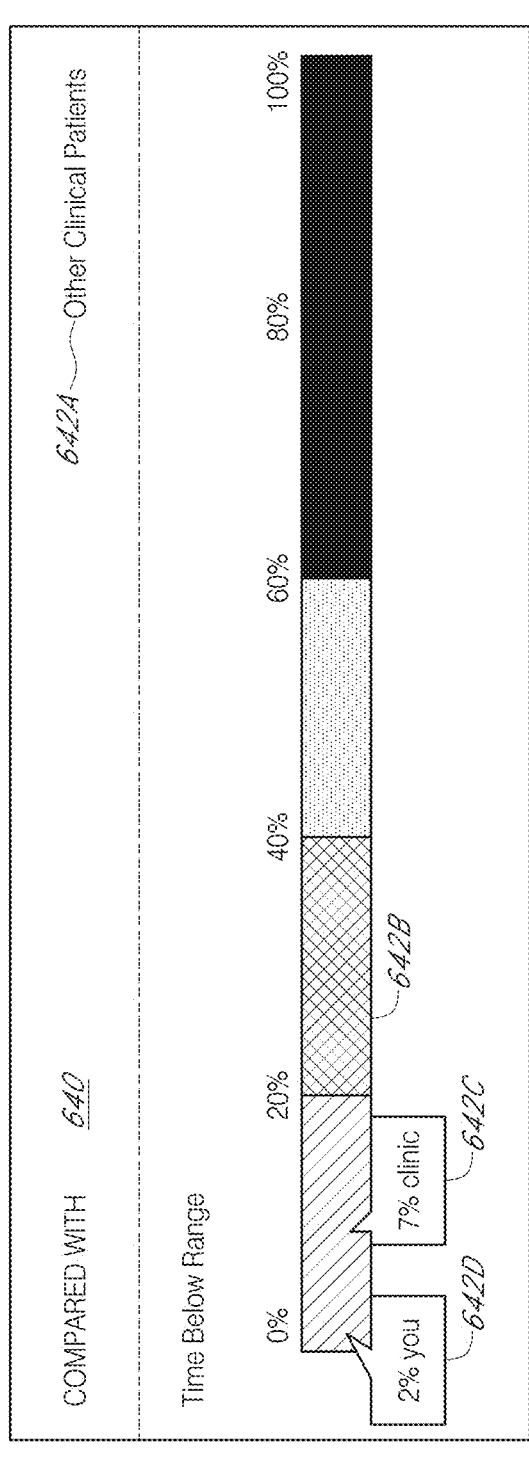
Figures 6, 6A, 7, 8, 9, 10, 11, 12:
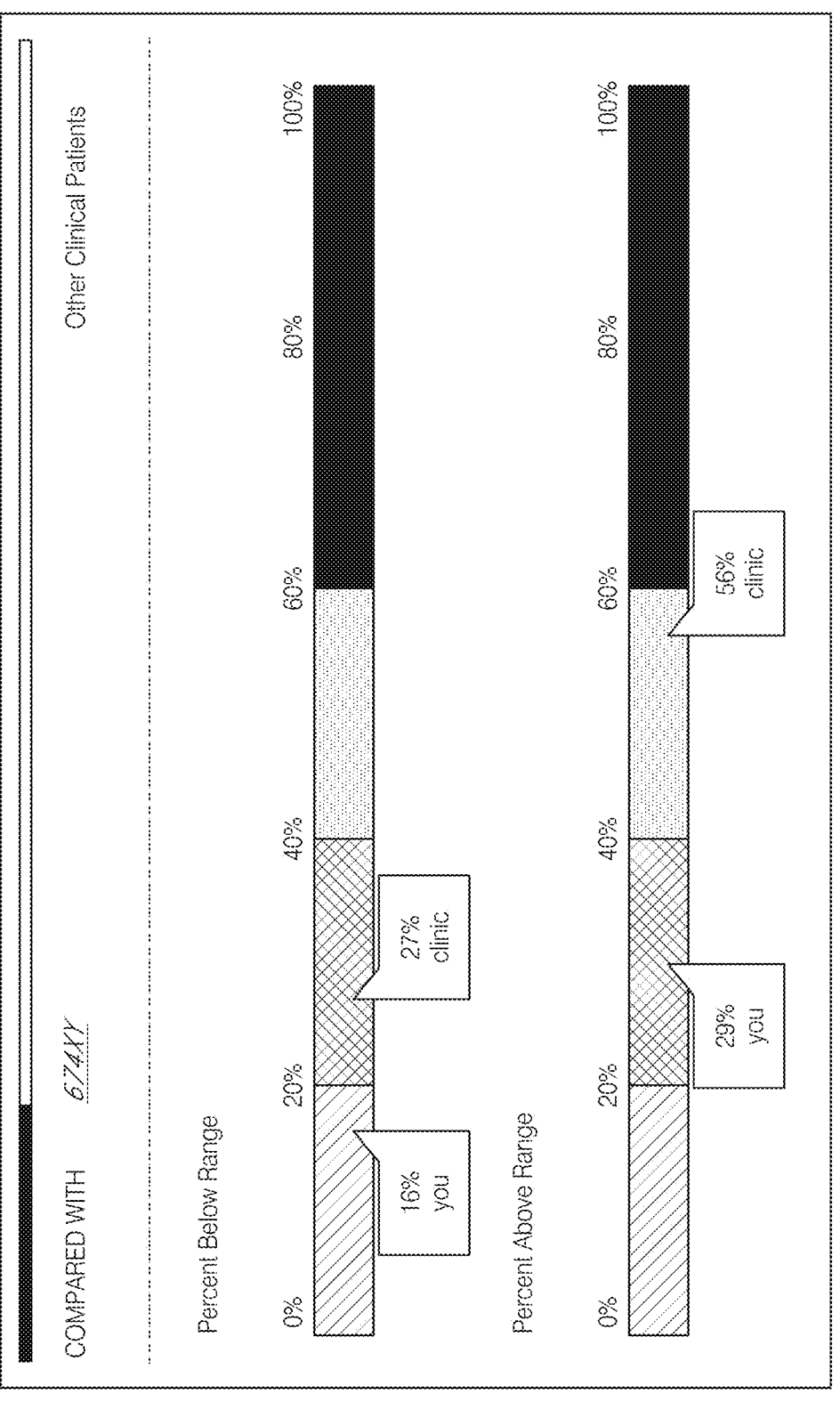
Figures 6, 6A, 7, 8, 9, 10, 11, 12, 13, 14:
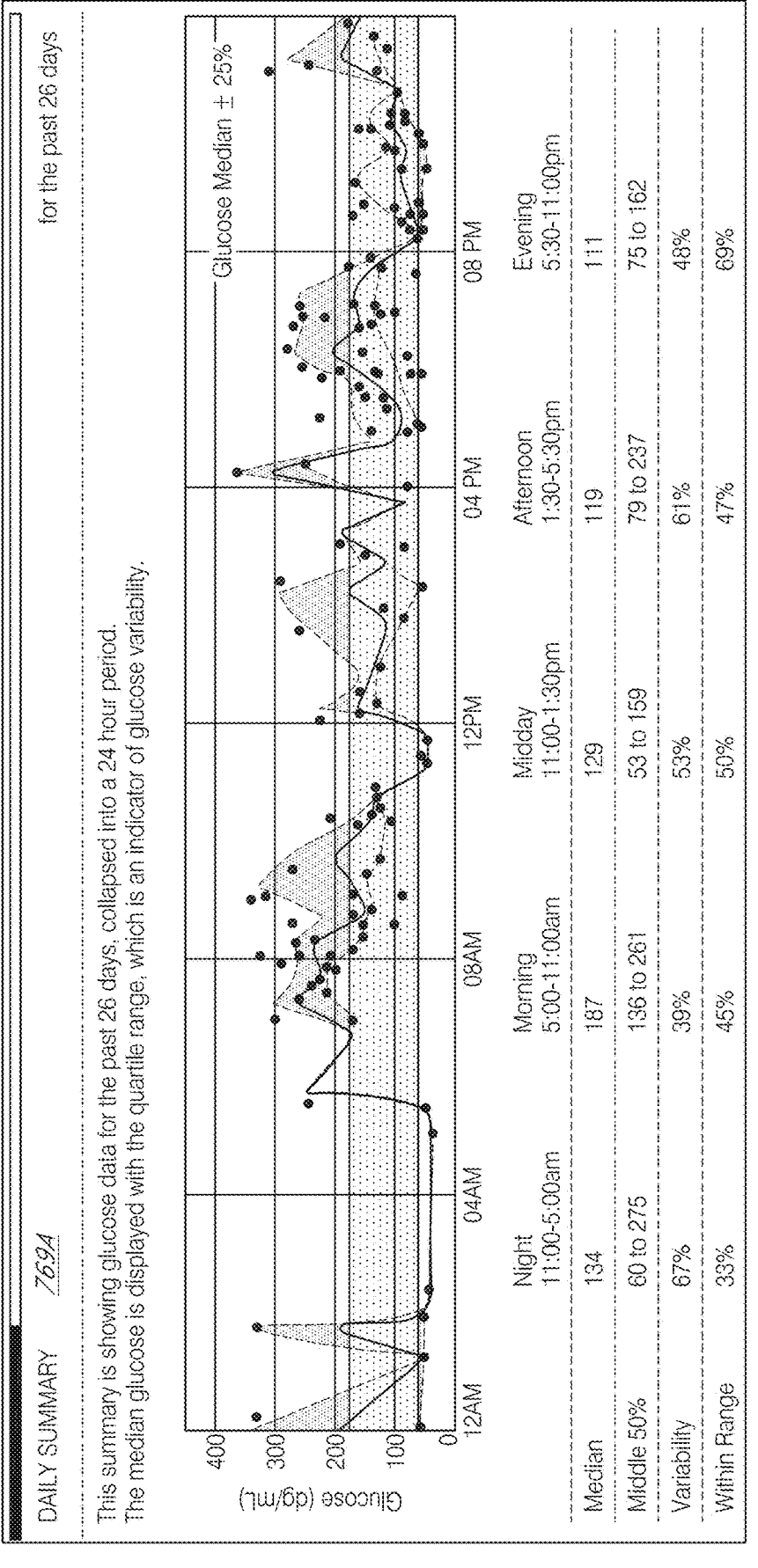
Figures 6, 6A, 7, 8, 9, 10, 11, 12, 13, 14, 15:
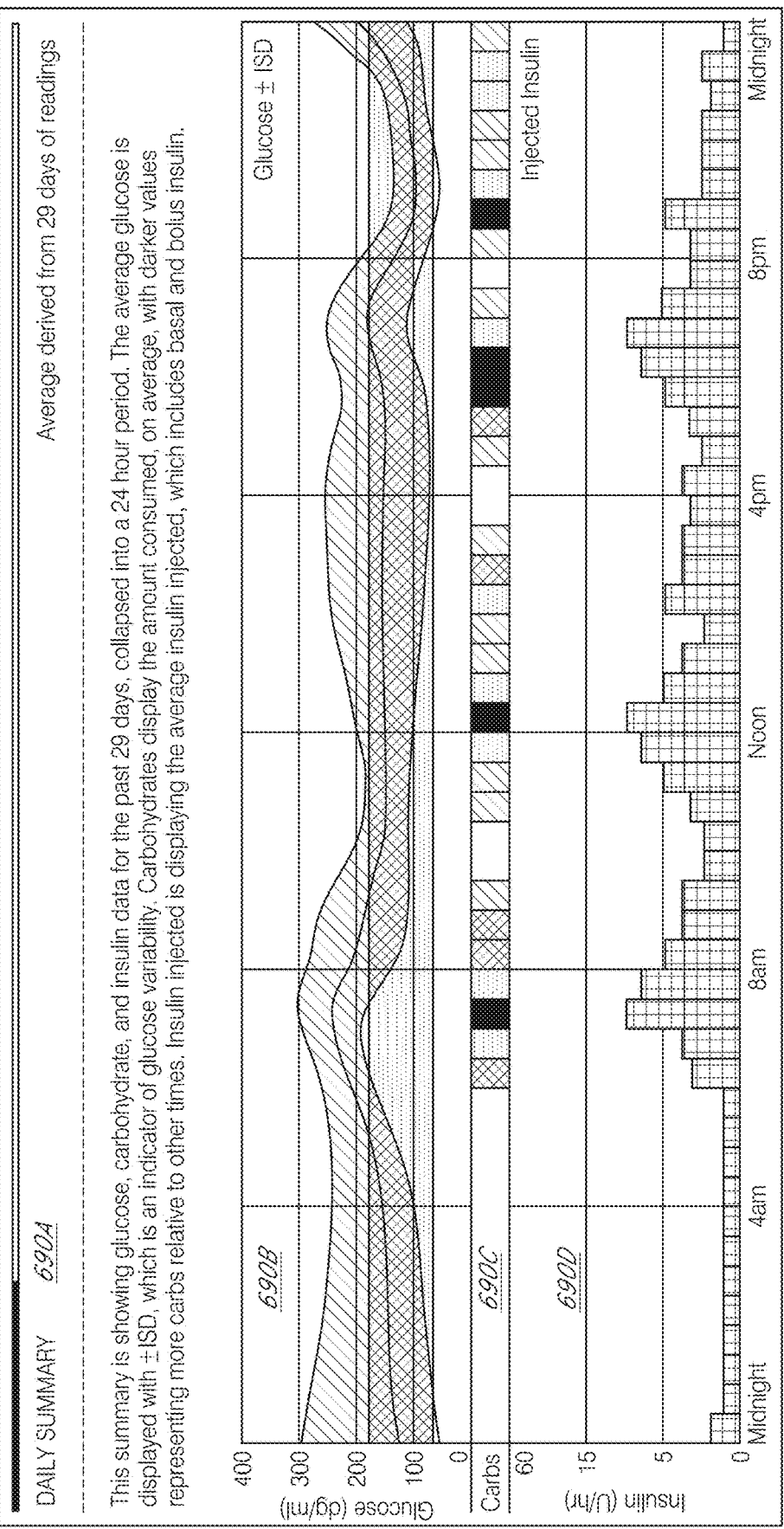
Figures 6, 6A, 7, 8, 9, 10, 11, 12, 13, 14, 15, 16:
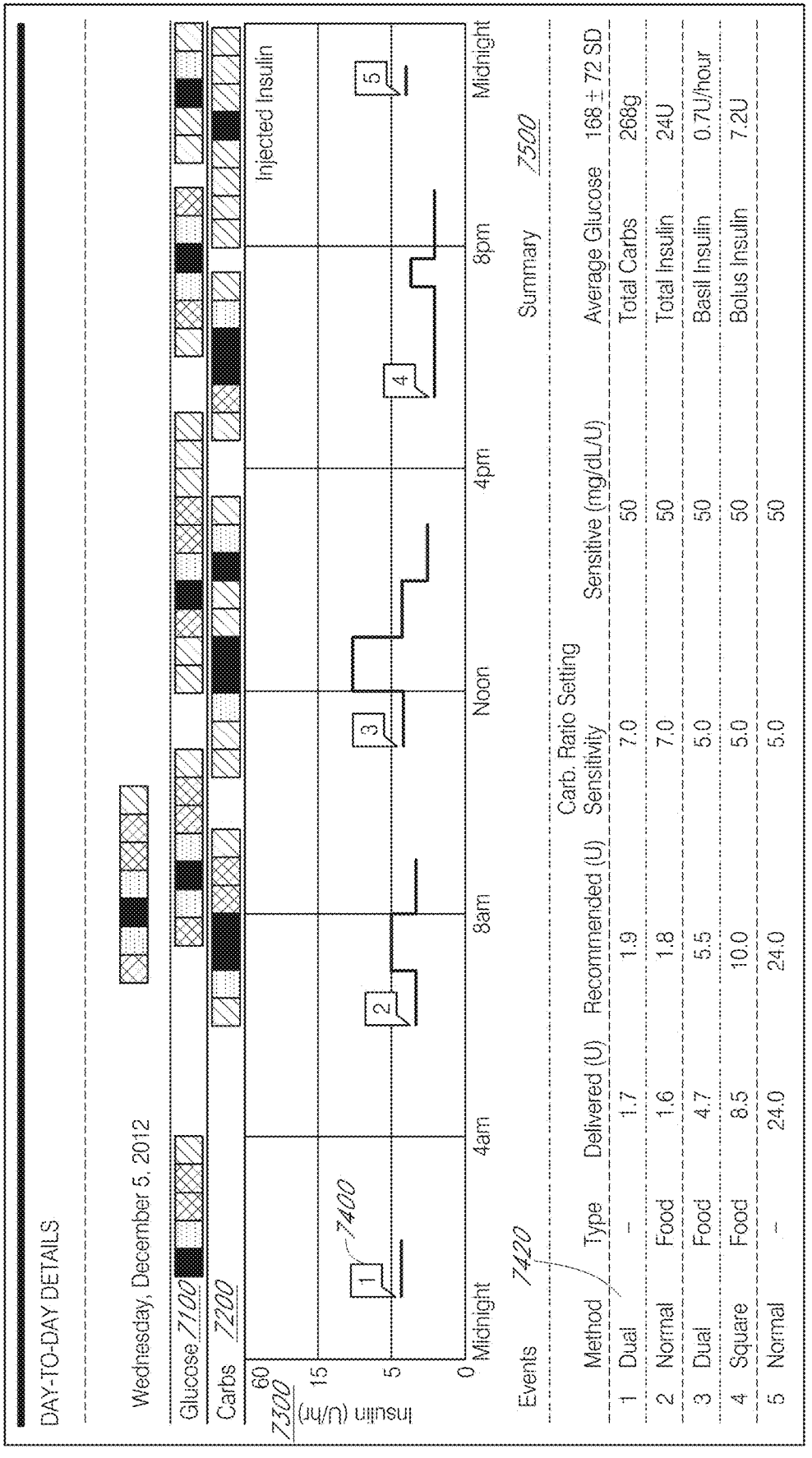
Figures 6, 6A, 7, 8, 9, 10, 11, 12, 13, 14, 15, 16, 17:
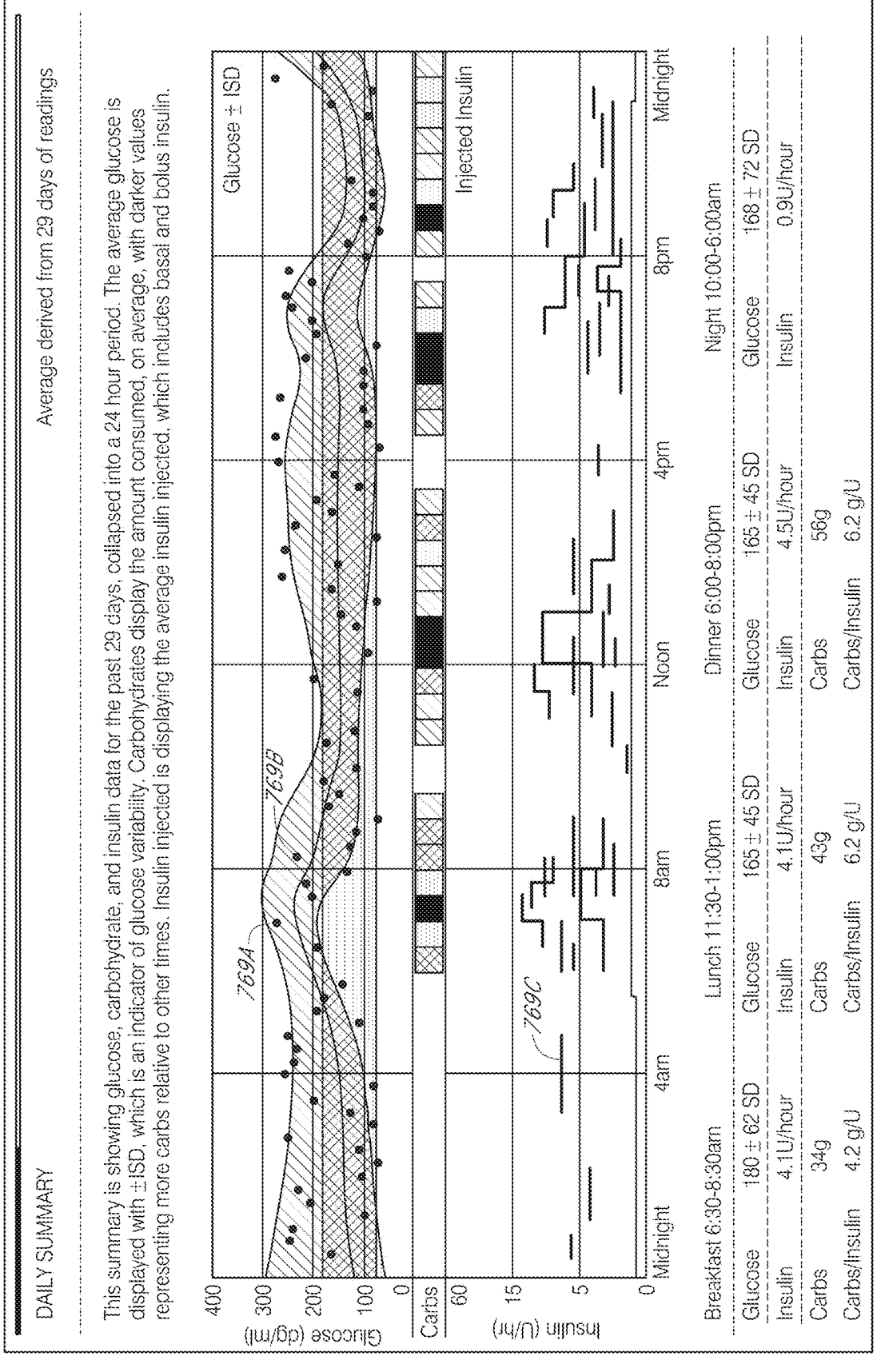
Figures 6, 6A, 7, 8, 9, 10, 11, 12, 13, 14, 15, 16, 17, 18:
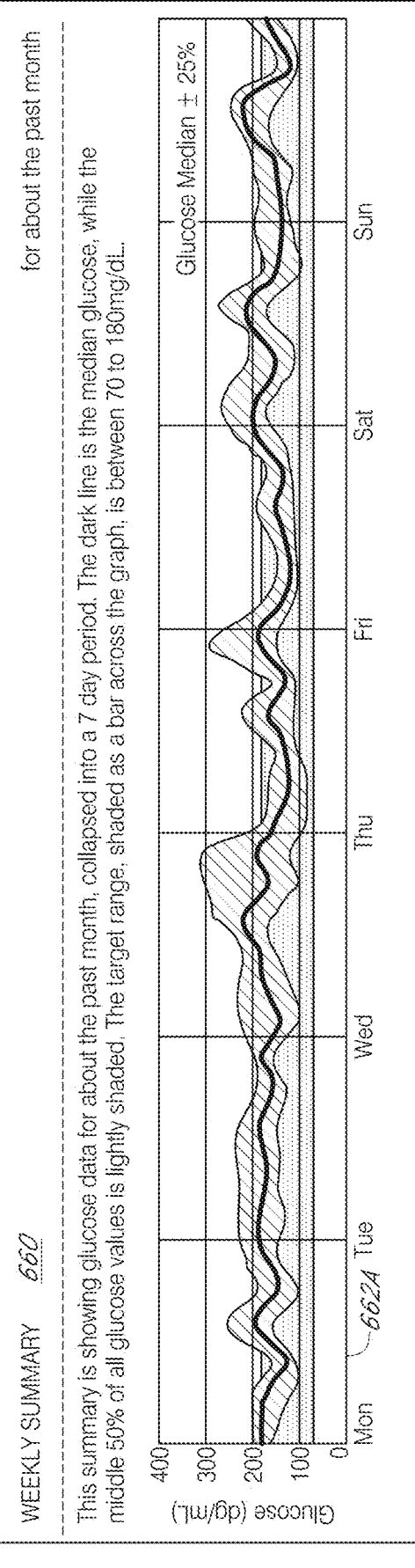
Figures 6, 6A, 7, 8, 9, 10, 11, 12, 13, 14, 15, 16, 17, 18, 19:
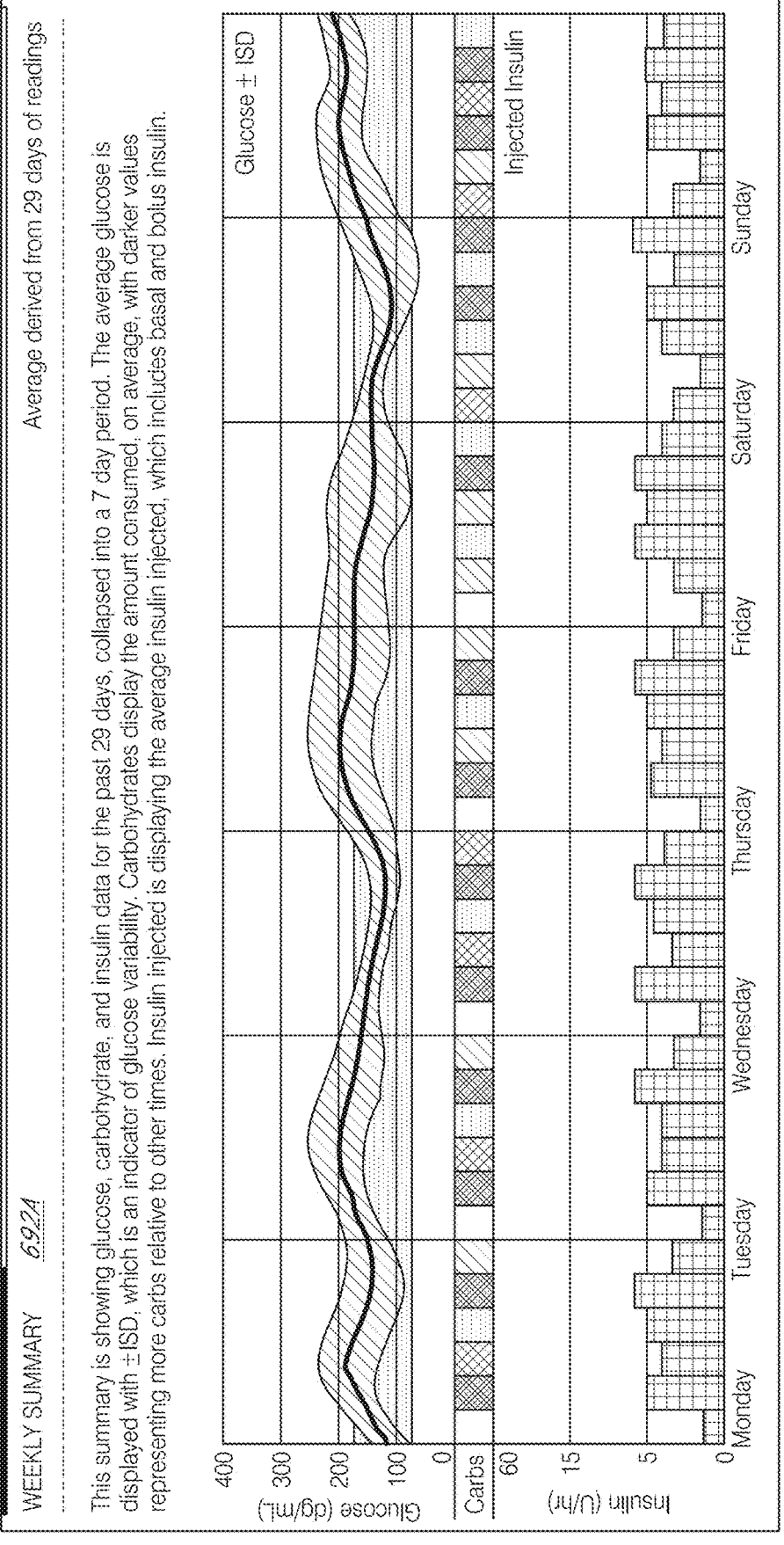
Figures 6, 6A, 7, 8, 9, 10, 11, 12, 13, 14, 15, 16, 17, 18, 19, 20:
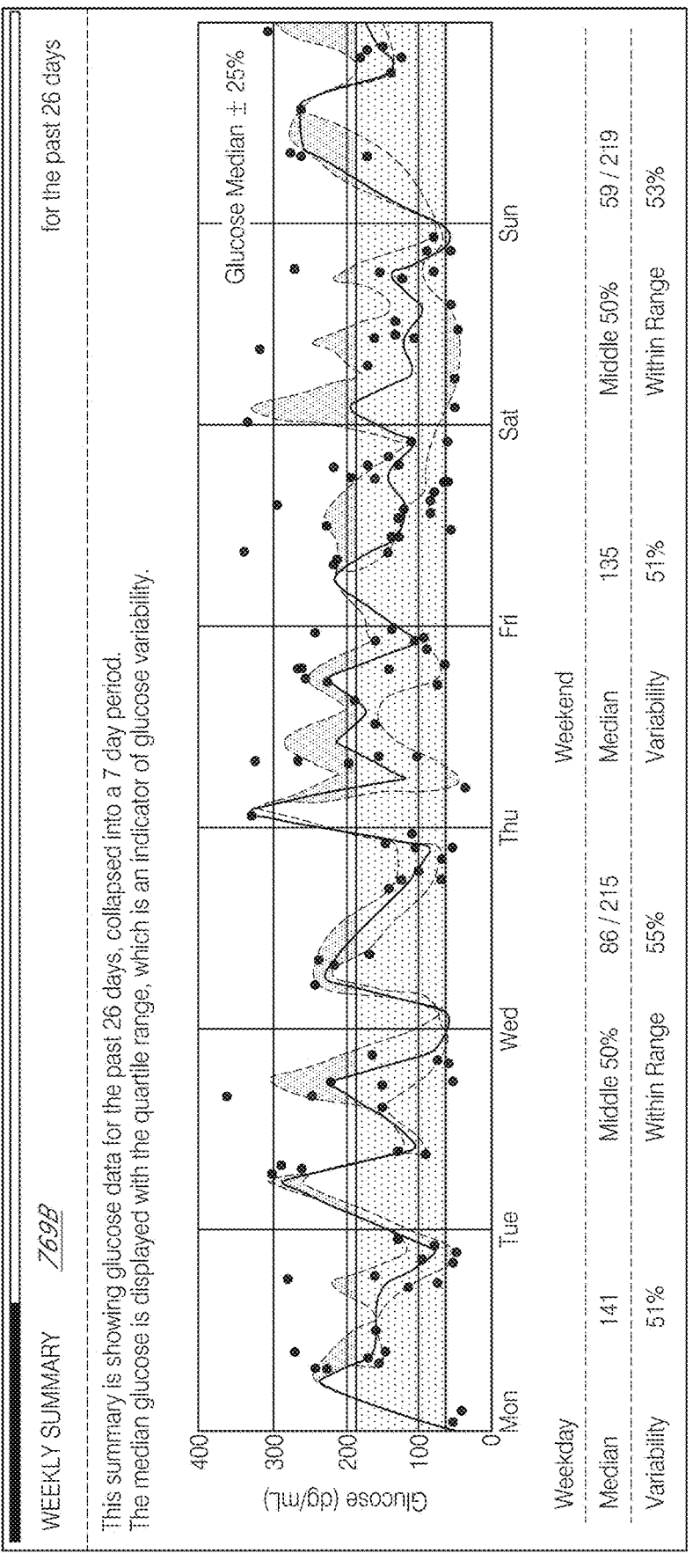
Figures 6, 6A, 7, 8, 9, 10, 11, 12, 13, 14, 15, 16, 17, 18, 19, 20, 21:
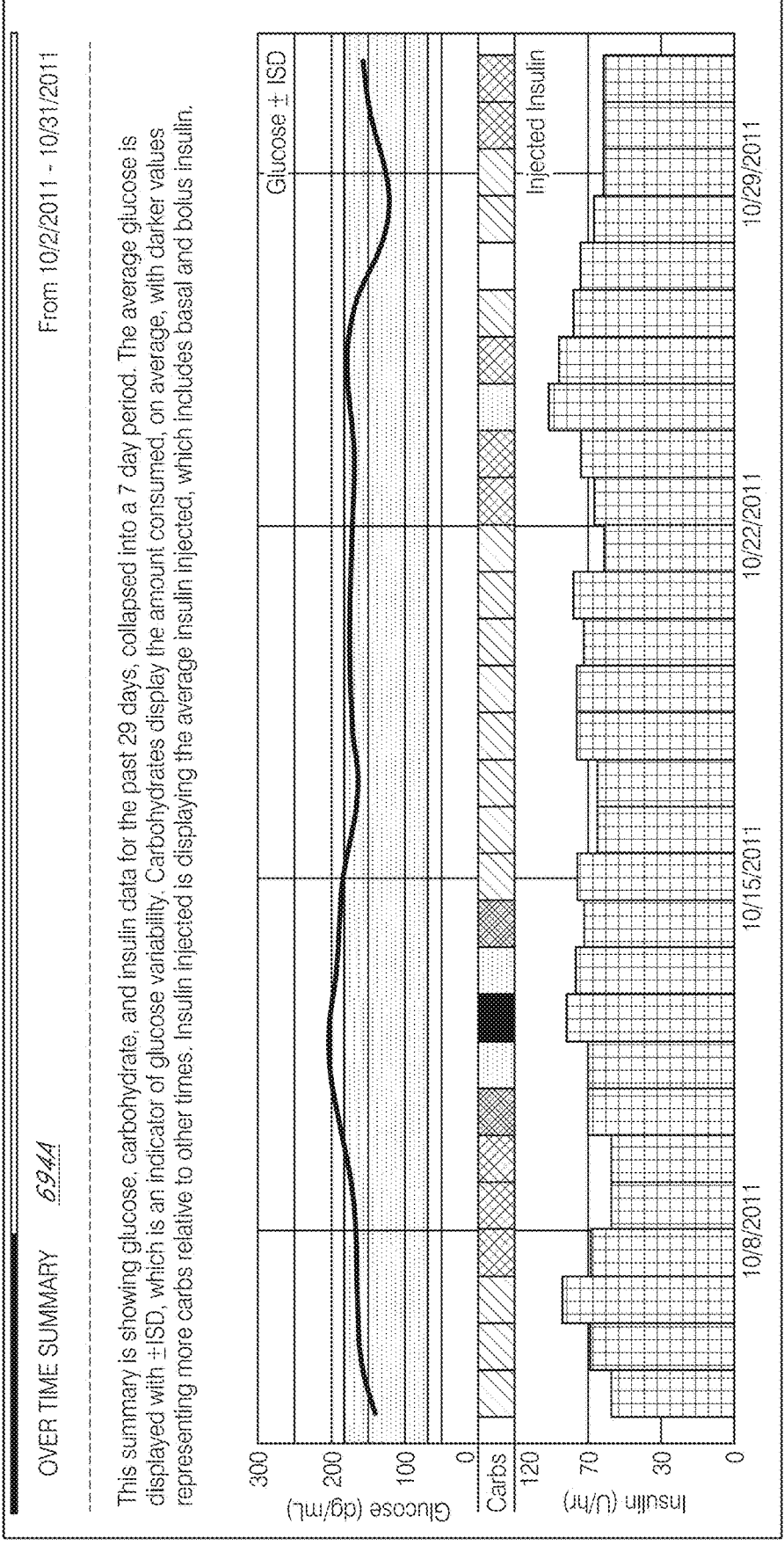
Figures 6, 6A, 7, 8, 9, 10, 11, 12, 13, 14, 15, 16, 17, 18, 19, 20, 21, 22:
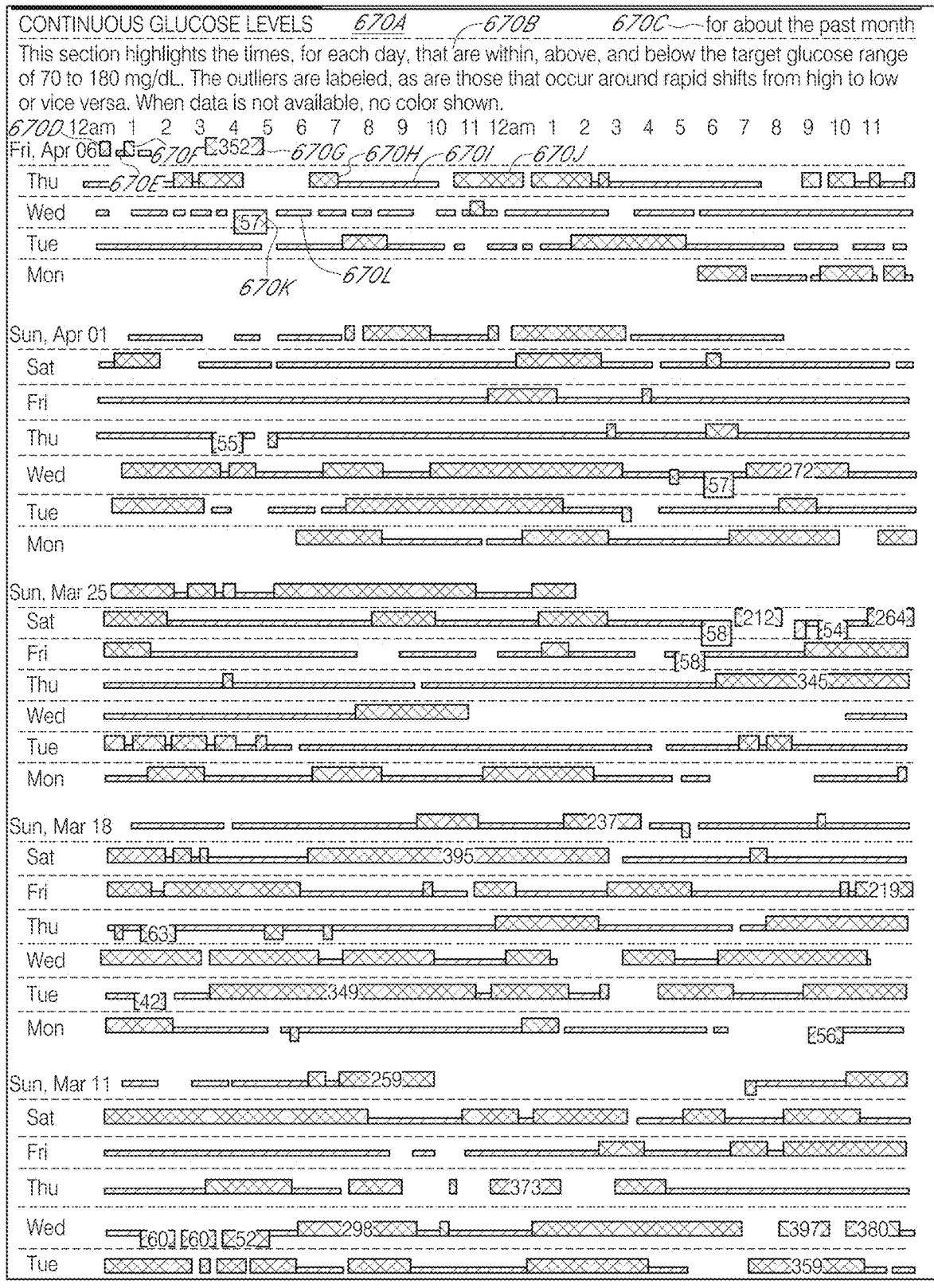
Figures 6, 6A, 7, 8, 9, 10, 11, 12, 13, 14, 15, 16, 17, 18, 19, 20, 21, 22, 23:
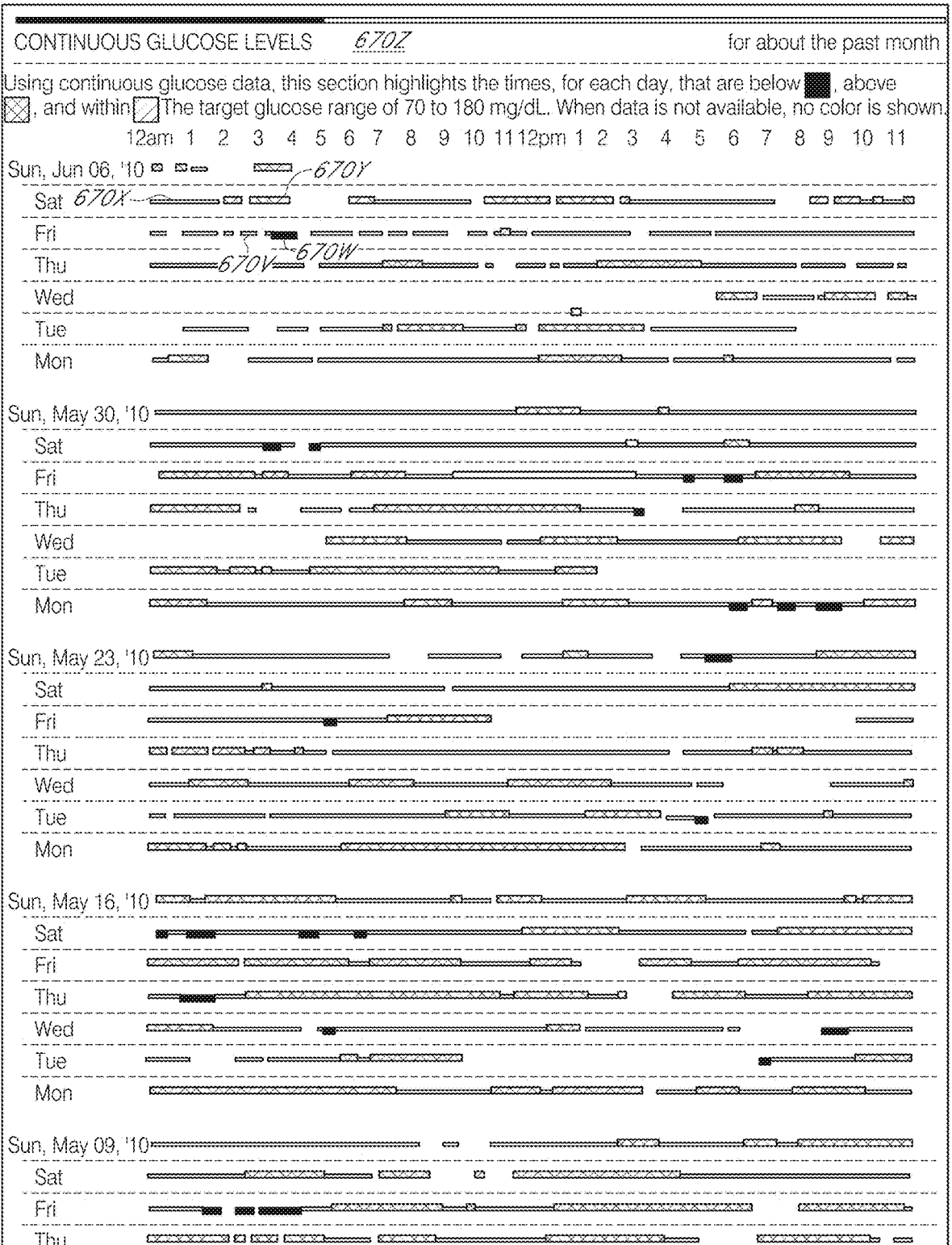
Figures 6, 6A, 7, 8, 9, 10, 11, 12, 13, 14, 15, 16, 17, 18, 19, 20, 21, 22, 23, 24:
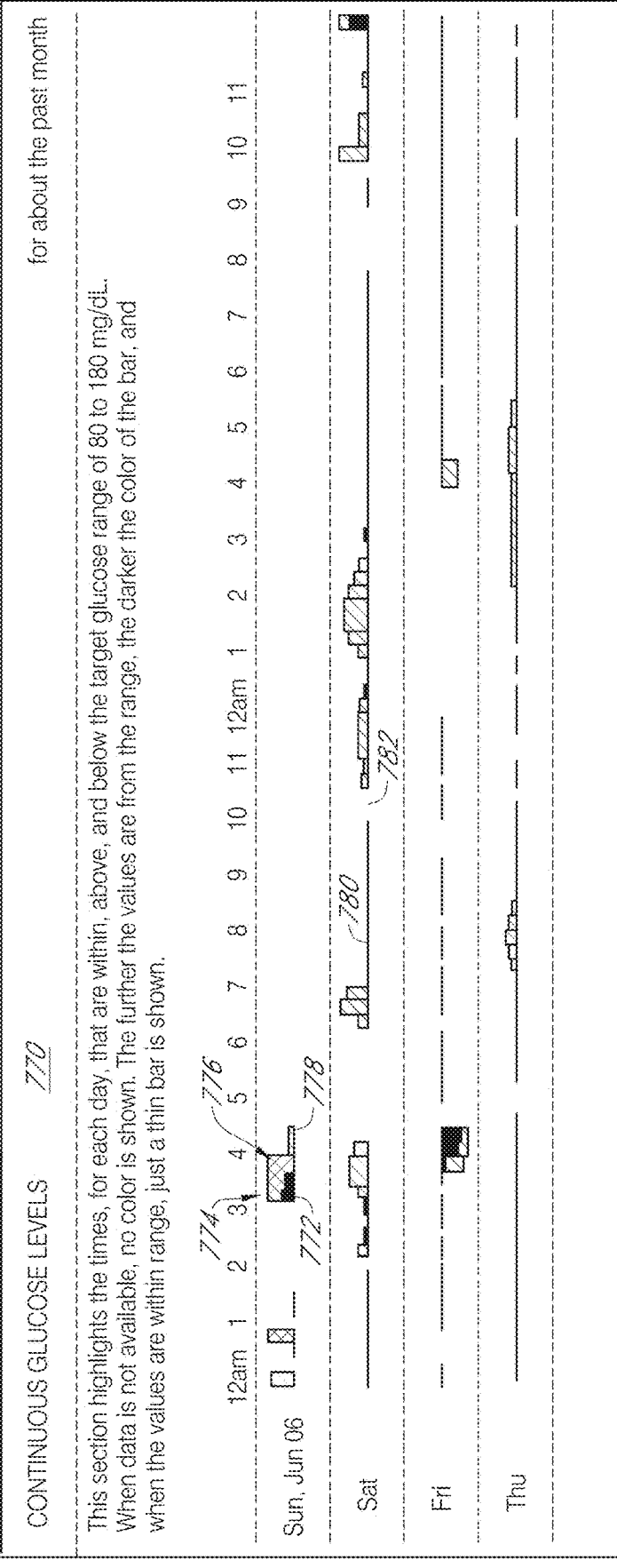
Figures 6, 6A, 7, 8, 9, 10, 11, 12, 13, 14, 15, 16, 17, 18, 19, 20, 21, 22, 23, 24, 25:
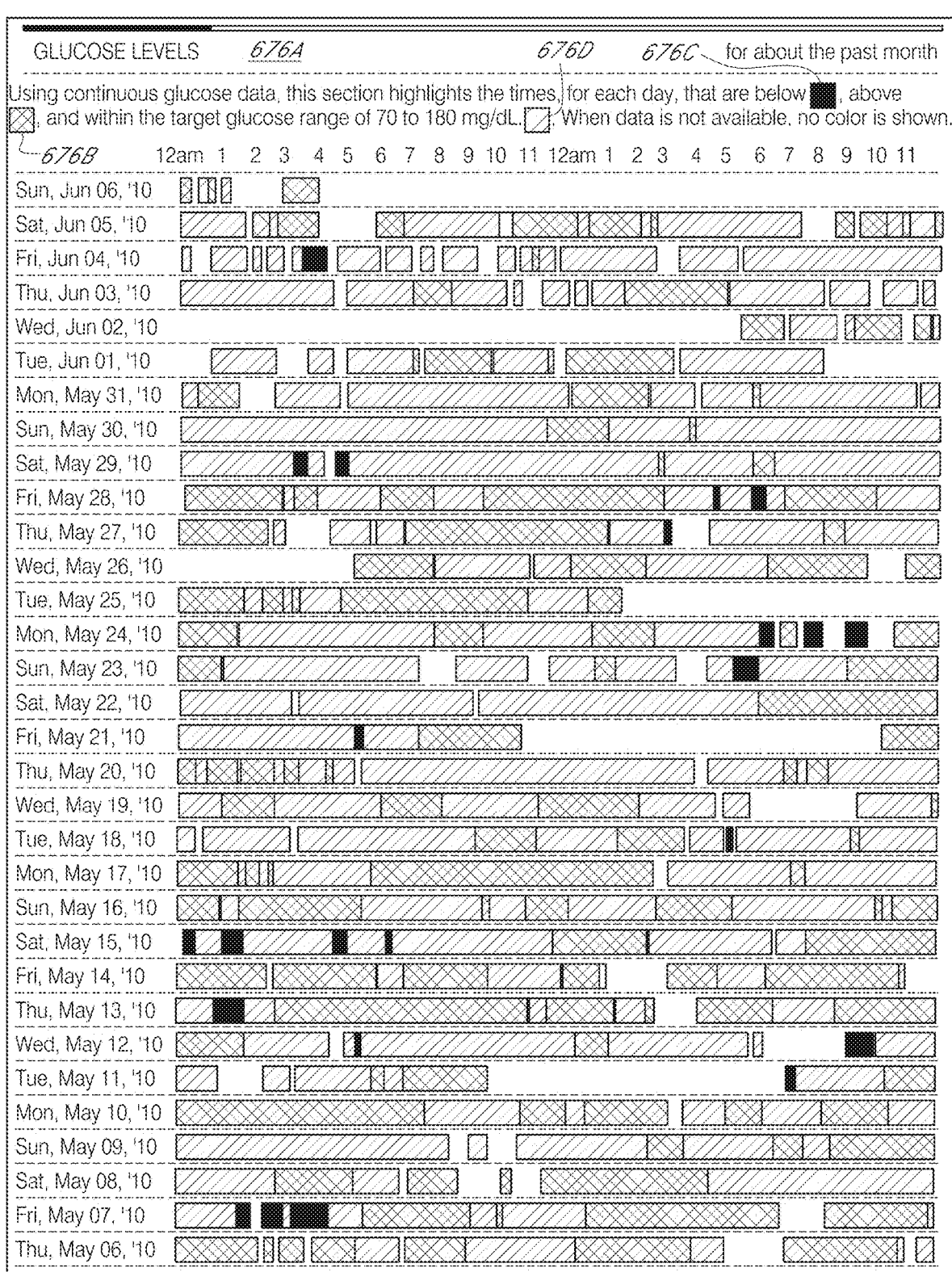
Figure 7:
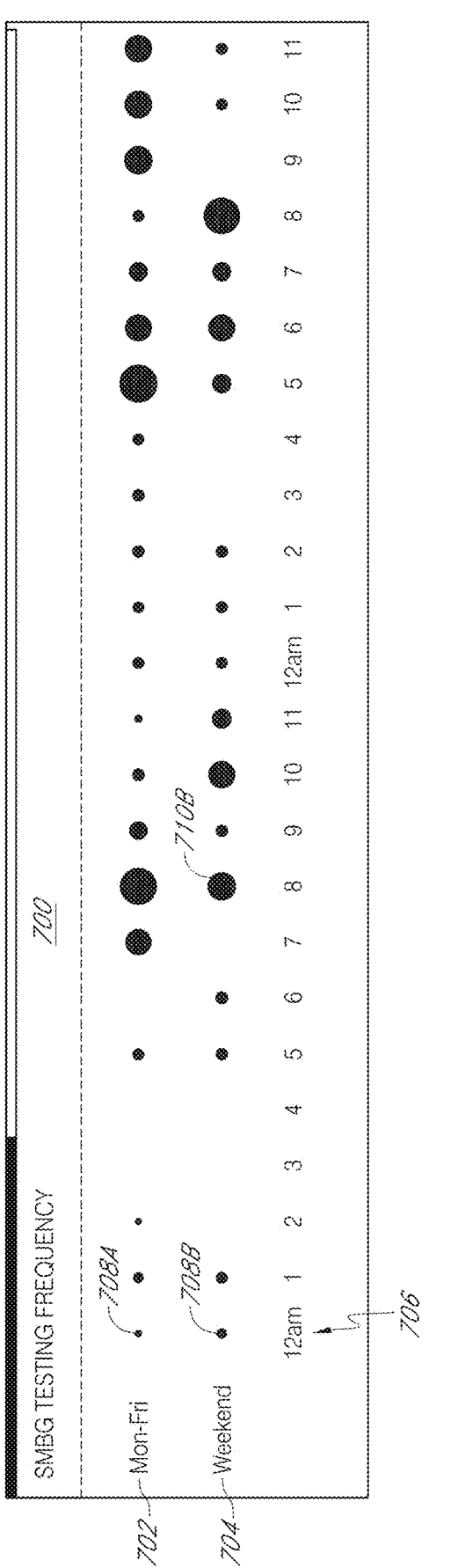
Figure 9:
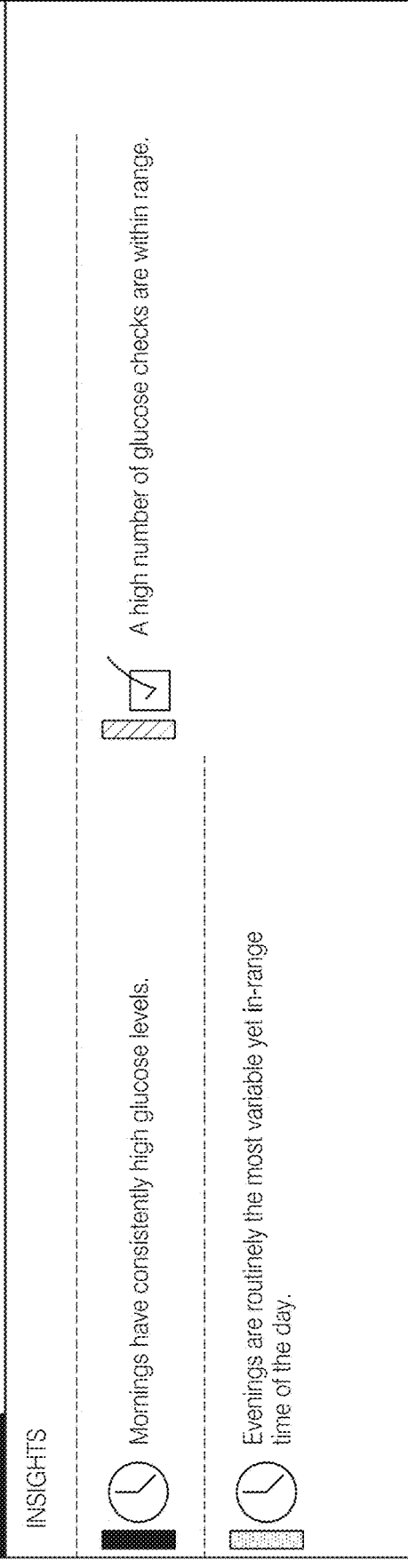
Figure 11:
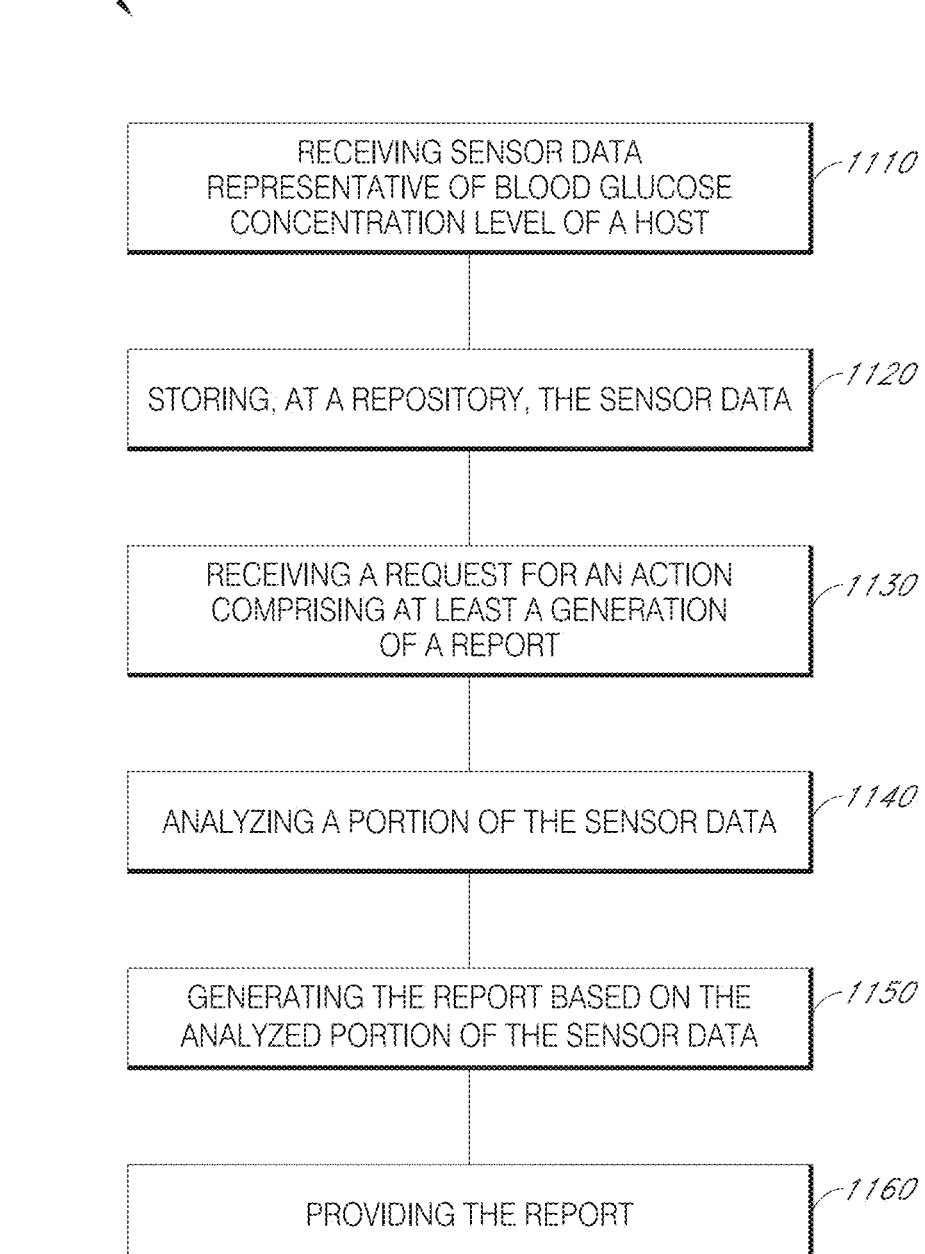

FIG. 10 depicts an example of a module providing "Days of Interest." The days of interest module provides a summary of information for a given time frame. For example, over a 30 day time period, the Days of Interest module may show the day of the week the patient's glucose values were most within range (e.g., Saturdays), the day of the week the patient's glucose values were most variable (e.g., Tuesdays), the day of the week the patient's glucose values are higher (e.g., Sundays) or lower (e.g., Thursdays) than the target range. This may allow a patient/host to determine whether there are any lifestyle issues on the identified days, which may be contributing to the variability, highs, and the like.

FIG. 11 depicts an example of a process 1100 for processing analyte data, in accordance with some exemplary implementations. The description of process 1100 may also refer to FIGS. 1, 4A, 4B, and 5.

At 1110, sensor data representative of an analyte measured in a host may be received, in accordance with some exemplary implementations. For example, analyte processor 490 may receive sensor data, such as values representative of blood glucose levels, from one or more devices, such as display devices 14, 16, 18, 20, sensor system 8, data retriever 465, user interfaces 410A-C, and the like. The analyte processor 490 may also receive (and/or determine) metadata associated with the analyte data, such as patient information, time of day associated with the measurement of the analyte data, and the like. Analyte processor 490 may process the received sensor data and/or metadata using one or more aspects of analyte processor 490 (e.g., authentication authorization 420, data parser 430B, calculation engine 420H, pattern detector 420I, report generator 420G, and the like as disclosed herein) and store the received sensor data and/or metadata in repository 475. Although the description of process 1100 refers to sensor data, analyte processor 490 may process other types of data as well.

At 1120, sensor data and/or metadata received at analyte processor 490 may be stored at repository 475 based on histograms and counts associated with the received sensor data and/or metadata, in accordance with some exemplary implementations. For example, the sensor data and/or metadata received at 1110 may be processed by calculation engine 420H to form counts, as noted above with respect to FIG. 5. In addition, the counts are then added to corresponding histograms (which may be stored at repository 475) based on metadata, such as a time of day associated with when measurement and the identity of the patient. In some exemplary implementations, the counts may be added to other histograms associated with cohorts. The repository 475 may store received sensor data, metadata, histograms, and/or counts for one or more patients (also referred to as hosts) for a time frame of 8 hours, 1 day, 2 days, 7 days, 30 days, or more to enable system 400 to analyze the stored data and generate the reports disclosed herein.

At 1130, the analyte processor 490 may receive a request to perform an action in accordance with some exemplary implementations. For example, analyte processor 490 may receive the request from a system, a processor, and/or a user interface, such as user interface 410A. The action may correspond to a request to generate a report for a certain patient, although other actions may be requested as well. The request may also indicate a time frame for the report, although the time frame may be determined programmatically by system 400 as well. The request may indicate other aspects of the request, such as types of modules to be included in the report. In some exemplary implementations, the request may undergo additional processing, such as authorization, authentication, parsing, and the like at analyte processor 490.

Moreover, the request may also correspond to other actions at analyte processor 490. Examples of actions include storing sensor data, metadata, and any other type of data at repository 475, retrieving sensor data, metadata, and any other type of data at repository 475, configuring reports and/or modules, customizing aspects of system 400 (e.g., adding devices, customizing reports, target glucose ranges, time frames for reports, and the like).

At 1140, analyte processor 490 and/or logic 420 may evaluate the time frame of the report, the patient's identity, and other metadata associated with the patient (e.g., number of devices, types of devices, and the like) and analyze a portion of the sensor data associated with the time frame. To illustrate further, logic 420 may determine that the time frame of a report is the past 30 days, the patient's identity 605A, and that the patient is associated with a single type of continuous blood glucose monitoring device. In this example, logic 420C may determine descriptive measurements (e.g., one or more statistics) for the past 30 days for the patient based on the data stored at repository 475 and/or request pattern generator 420I to detect patterns for the patient's data stored at repository 475 in the last 30 days. In some exemplary implementations, the time frame of the report and the corresponding data evaluated for the report is selected by a user (e.g., a patient, a clinician, and the like) or programmatically by system 400.

At 1150, logic 420 may initiate report generation at report generator 420G based on the analysis performed at 1140. For example, logic 420 may evaluate the time frame of the report, the patient's identity, and other metadata associated with the patient (e.g., number of devices, types of devices, and the like), and determine the type of modules to include in the report and the configuration of those modules. To illustrate further, logic 420 may determine that the time frame of the report is the past 30 days, the patient's identity 605A, and that the patient is associated with a single continuous glucose monitoring device. In this example, logic 420C may determine modules customized to present an analysis, such as statistics and patterns, for continuous blood glucose monitoring data, such as highlights module 607A, continuous glucose levels module 670A, and the like. In some example embodiments, the modules may be selected dynamically as described above with respect to FIG. 6A-2. The modules may be composed to form a report, such as report 700 at FIG. 6A-1, to cover the patient's data over the past 30 days, although other types of report and/or modules may be used as well. Although the previous example refers to the generated report as a graphical report, the report may be text based as well or may be generated as a machine-to-machine data exchange.

At 1160, the generated report may be provided to, for example, a user interface, such as user interface 410A-C, another machine, and the like.

Referring again to FIGS. 4A-B, in some exemplary implementations, the system 400 may store health data separately from personally identifiable information, which is encrypted. For example, system 400 may include a security layer below the logic layer so that encryption occurs when data is stored to repository 475. In some exemplary implementations, the encryption is based on multiple factors, such as the host, the storage location (e.g., row-column information), and the like. For example, an encryption algorithm, such as the advanced encryption algorithm and the like may be implemented. In some implementations, the encryption keys may be split and stored on separate portions of system 400 (e.g., on analyte processor 490, servers for the databases, and the like) with separate user credentials for authentication.

In some exemplary implementations, the repository 475 is distributed. For example, the repository 475 may comprise a plurality of persistent storage devices, which are distributed. Moreover, the persistent storage devices may include one or more of relational databases, non-relational document stores, non-relation key-value data stores, hierarchical file system-like stores (also referred to as data stores), and the like. Furthermore, the repository 475 may be replicated so that the storage devices are geographically dispersed.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. Other implementations may be within the scope of the following claims.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. Other implementations may be within the scope of the following claims.

Methods and devices that are suitable for use in conjunction with aspects of the preferred embodiments are disclosed in U.S. Pat. Nos. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206,297; 8,216,139; 8,229,534; 8,229,535; 8,229,536; 8,231,531; 8,233,958; 8,233,959; 8,249,684; 8,251,906; 8,255,030; 8,255,032; 8,255,033; 8,257,259; 8,260,393; 8,265,725; 8,275,437; 8,275,438; 8,277,713; 8,280,475; 8,282,549; 8,282,550; 8,285,354; 8,287,453; 8,290,559; 8,290,560; 8,290,561; 8,290,562; 8,292,810; 8,298,142; 8,311,749; 8,313,434; 8,321,149; 8,332,008; 8,346,338; 8,364,229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-

0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No.

2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; and U.S. Patent Publication No. 2005-0182451-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS"; U.S. application Ser. No. 13/779,607 filed on Feb. 27, 2013 and entitled "ZWITTERION SURFACE MODIFICATIONS FOR CONTINUOUS SENSORS"; U.S. application Ser. No. 13/780,808 filed on Feb. 28, 2013 and entitled "DEVICES, SYSTEMS, AND METHODS TO COMPENSATE FOR EFFECTS OF TEMPERATURE ON IMPLANTABLE SENSORS"; and U.S. application Ser. No. 13/784,523 filed on Mar. 4, 2013 and entitled "ANALYTE SENSOR WITH INCREASED REFERENCE CAPACITY".

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A system for reporting analyte data, the system comprising:
   a continuous analyte sensor system including an electronics module and an analyte sensor, the continuous analyte sensor system configured to generate analyte sensor data of a host, and wirelessly communicate data including the analyte sensor data;
   a computer, in wireless communication with the continuous analyte sensor system, the computer configured to:
   receive data pertaining to a host, the data including the analyte sensor data,
   receive a request for a report of the analyte sensor data over a period of time,
   analyze at least a portion of the data to determine one or more time in range values that indicate a relationship between the analyte sensor data and one or more predefined rules pertaining to a time in range,
   select one or more data presentation modules from a plurality of data presentation modules based on a mapping between the one or more data presentation modules and metadata associated with the analyte sensor, the host, a user, or the report, and
   generate a report including the one or more data presentation modules based on the one or more time in range values,
   wherein the one or more data presentation modules dynamically present the one or more time in range values; and
   a device, in communication with the computer via a network, the device configured to present the report on a display.

2. The system of claim 1, wherein the period of time includes 1 day, 2 days, 7 days, or 30 days.

3. The system of claim 1, wherein:
   the metadata associated with the analyte sensor includes at least one of an analyte sensor type, an analyte sensor quantity, or an analyte sensor device type;
   the metadata associated with the host includes at least one of a host state, a host age, a host weight, a host gender, a host address, a host health condition, accelerometer data from a device operated by the host, or location data from a device operated by the host,
   the metadata associated with the user includes at least one of a user preference, or a size of a display of a user device; and
   the metadata associated with the report includes a report length, report templates, or report rules associated with the data presentation modules.

4. The system of claim 3, wherein the computer is further configured to send the report to a device including a display configured to present the report, wherein the device includes a smartphone, a tablet, a laptop computer or a desktop computer.

5. The system of claim 4, wherein to generate the report includes to configure the one or more data presentation modules to be displayed on the device based on a size of the display.

6. The system of claim 4, wherein the computer is further configured to:
determine whether a user sending the request for the report is authorized to receive the report, including:
authenticate a security credential associated with the user sending the request;
if the security credential is authenticated, send the report to the user; and
if the security credential is not authenticated, do not send the report to the user.

7. The system of claim 1, wherein to generate the report includes to structure the one or more data presentation modules to present a visual representation of the analyte sensor data, the visual representation including at least one of:
a graph having distinct graphical elements representative of whether analyte levels over the period of time are at least one of at, above or below, or within a predetermined range;
a call out including a numeric value associated with at least one feature of the visual representation; or
a textual legend including a description of the visual representation.

8. The system of claim 1, wherein the computer is further configured to analyze the metadata and select one or more data presentation module templates, wherein to generate the report further includes to arrange the one or more data presentation modules in the one or more data presentation module templates.

9. The system of claim 8, wherein to analyze the metadata includes to identify one or more factors of the metadata, the one or more factors including one or more of an amount of available analyte sensor data during the period of time, a type of metadata available during the period of time, devices used by the host configured to use information associated with the analyte sensor data, user preference information, a size of a user interface available to present the one or more data presentation modules, or a quantity of analyte sensor data included in the one or more data presentation modules over the period of time.

10. The system of claim 8, wherein selection of the one or more data presentation module templates is based on a type of user from which the request for the report is received, the type of user including a patient, a caregiver, a specific type of medical professional, a businessperson, or a group of patients.

11. A computer-based method for reporting analyte data, the computer-based method comprising:
receiving data pertaining to a host, the data including analyte sensor data generated by an analyte sensor;
receiving a request for a report of the analyte sensor data over a period of time;
analyzing at least a portion of the data to determine one or more time in range values that indicate a relationship between the analyte sensor data and one or more predefined rules pertaining to a time in range;
selecting one or more data presentation modules from a plurality of data presentation modules based on a mapping between the one or more data presentation modules and metadata associated with the analyte sensor, the host, a user, or the report; and
generating a report including the one or more data presentation modules based on the one or more time in range values,
wherein the one or more data presentation modules dynamically present the one or more time in range values.

12. The computer-based method of claim 11, wherein the period of time includes 1 day, 2 days, 7 days, or 30 days.

13. The computer-based method of claim 11, wherein:
the metadata associated with the analyte sensor includes at least one of an analyte sensor type, an analyte sensor quantity, or an analyte sensor device type;
the metadata associated with the host includes at least one of a host state, a host age, a host weight, a host gender, a host address, a host health condition, accelerometer data from a device operated by the host, or location data from a device operated by the host,
the metadata associated with the user includes at least one of a user preference, or a size of a display of a user device; and
the metadata associated with the report includes a report length, report templates, or report rules associated with the data presentation modules.

14. The computer-based method of claim 13, further comprising sending the report to a device including a display configured to present the report, wherein the device includes a smartphone, a tablet, a laptop computer or a desktop computer.

15. The computer-based method of claim 14, wherein generating the report includes configuring the one or more data presentation modules to be displayable on the device based on a size of the display.

16. The computer-based method of claim 14, further comprising:
determining whether a user sending the request for the report is authorized to receive the report, including:
authenticating a security credential associated with the user sending the request;
if the security credential is authenticated, sending the report to the user; and
if the security credential is not authenticated, not sending the report to the user.

17. The computer-based method of claim 11, wherein generating the report includes structuring the one or more data presentation modules to present a visual representation of the analyte sensor data, the visual representation including at least one of:
a graph having distinct graphical elements representative of whether analyte levels over the period of time are at least one of at, above or below, or within a predetermined range;
a call out including a numeric value associated with at least one feature of the visual representation; or
a textual legend including a description of the visual representation.

18. The computer-based method of claim 11, further comprising analyzing the metadata to select one or more data presentation module templates, wherein generating the report further includes arranging the one or more data presentation modules in the one or more data presentation module templates.

19. The computer-based method of claim 18, wherein analyzing the metadata includes identifying one or more factors of the metadata, the one or more factors including one or more of an amount of available analyte sensor data during the period of time, type of metadata available during the period of time, devices used by the host operable to use information associated with the analyte sensor data, user preference information, size of a user interface available to present the one or more data presentation modules, or a quantity of analyte sensor data included in the one or more data presentation modules over the period of time.

20. The computer-based method of claim 18, wherein selection of the one or more data presentation module templates is based on a type of user from which the request for the report is received, the type of user including a patient, a caregiver, a specific type of medical professional, a businessperson, or a group of patients.

\* \* \* \* \*